US009677058B2

(12) United States Patent
Cramer et al.

(10) Patent No.: US 9,677,058 B2
(45) Date of Patent: Jun. 13, 2017

(54) POLYPEPTIDES HAVING GLUCOAMYLASE ACTIVITY AND METHOD OF PRODUCING THE SAME

(71) Applicant: DUPONT NUTRITION BIOSCIENCES APS, Copenhagen K (DK)

(72) Inventors: Jacob Flyvholm Cramer, Århus V (DK); Neville Marshall Fish, Stockport (GB); Peter Edvard Degn, Egå (DK); Igor Nikolaev, Noordwijk (NL); Paulien Kruithof, Zoetermeer (NL); Piet Van Solingen, Naaldwijk (NL); Sander Van Stigt Thans, Nieuwerkerk aan den IJssel (NL); Suzy Breneman, Orfordville, WI (US); Jayarama K. Shetty, Pleasanton, CA (US); Sung Ho Lee, North Liberty, IA (US)

(73) Assignee: DUPONT NUTRITION BIOSCIENCES APS, Copenhagen K (DK)

( * ) Notice: Subject to any disclaimer, the term of this patent is extended or adjusted under 35 U.S.C. 154(b) by 135 days.

(21) Appl. No.: 14/366,214

(22) PCT Filed: Dec. 20, 2012

(86) PCT No.: PCT/EP2012/076352
§ 371 (c)(1),
(2) Date: Jun. 17, 2014

(87) PCT Pub. No.: WO2013/092840
PCT Pub. Date: Jun. 27, 2013

(65) Prior Publication Data
US 2014/0356922 A1    Dec. 4, 2014

Related U.S. Application Data

(60) Provisional application No. 61/579,429, filed on Dec. 22, 2011.

(30) Foreign Application Priority Data

Jan. 16, 2012    (EP) ..................... 12151285

(51) Int. Cl.
| C12N 9/26 | (2006.01) |
| C12C 5/00 | (2006.01) |
| C12C 12/00 | (2006.01) |
| C12P 7/06 | (2006.01) |
| C12N 9/34 | (2006.01) |
| C12C 11/00 | (2006.01) |
| C12C 12/02 | (2006.01) |
| C12C 12/04 | (2006.01) |
| A23L 29/30 | (2016.01) |

(52) U.S. Cl.
CPC ............ *C12N 9/2408* (2013.01); *A23L 29/35* (2016.08); *C12C 5/006* (2013.01); *C12C 11/003* (2013.01); *C12C 12/00* (2013.01); *C12C 12/02* (2013.01); *C12C 12/04* (2013.01); *C12N 9/2428* (2013.01); *C12P 7/06* (2013.01); *C12Y 302/01003* (2013.01); *C12G 2200/15* (2013.01); *Y02E 50/17* (2013.01)

(58) Field of Classification Search
None
See application file for complete search history.

(56) References Cited

U.S. PATENT DOCUMENTS

| 4,318,989 | A | 3/1982 | Marshall |
| 4,514,496 | A | 4/1985 | Yoshizumi et al. |
| 4,617,273 | A | 10/1986 | Olsen et al. |
| 4,666,718 | A | 5/1987 | Lowery et al. |
| 4,870,014 | A | 9/1989 | Eratt et al. |
| 5,422,267 | A | 6/1995 | Yocum et al. |
| 6,254,914 | B1 | 7/2001 | Singh et al. |
| 6,582,914 | B1 | 6/2003 | Caldwell et al. |
| 6,613,365 | B1 | 9/2003 | Yamamoto |
| 6,899,910 | B2 | 5/2005 | Johnston et al. |
| 7,037,704 | B2 | 5/2006 | Dunn-Coleman et al. |
| 2004/0081663 | A1 | 4/2004 | Chang et al. |
| 2006/0154353 | A1 | 7/2006 | Duan et al. |

FOREIGN PATENT DOCUMENTS

| JP | 2007097462 | 4/2007 |
| WO | WO0075296 | 12/2000 |
| WO | WO03049550 | 6/2003 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Altschhul, Stephen, et al., "Basic Local Alignment Search Tool," J. Mol. Bio., 1990, p. 403-410, vol. 215, Academic Press Limited.
Altschhul, Stephen, et al., "[27] Local Alignment Statistics," Methods in Enzymology, 1996, p. 460-480, vol. 266.
Devereux, John, et al., "A comprehensive set of sequence analysis programs for the VAX," Nucleic Acids Research, 1984, p. 387-395, vol. 12, No. 1, IRL Press Limited.
Ensminger, Peter, "Beer Data: Alcohol, Calorie, and Attenuation Levels of Beer," Homebrew Digest, <http://hbd.org/ensmingr/>.
Feng, Da-Fei, et al., "Progressive Sequence Alignment as a Prerequisite to Correct Phylogenetic Trees," Journal of Molecular Evolution, 1987, p. 351-360, vol. 25, Springer-Verlag New York Inc.

(Continued)

*Primary Examiner* — Christian Fronda
(74) *Attorney, Agent, or Firm* — Nelson Mullins Riley & Scarborough LLP

(57) ABSTRACT

The present invention relates to polypeptides having glucoamylase activity with improved properties and to compositions comprising these polypeptides suitable for use in the production of a food, beverage (e.g. beer), feed, or biofuel. Also described is an improved and cost-effective process for isolating glucoamylases suitable for large scale protein purification procedures. Furthermore, different methods and uses related to glucoamylases according to the invention are disclosed, such as in a brewing process.

11 Claims, 18 Drawing Sheets

(56) References Cited

FOREIGN PATENT DOCUMENTS

| WO | WO2004080923 | 9/2004 |
| WO | WO2004081193 | 9/2004 |
| WO | WO2006043178 | 4/2006 |
| WO | WO2007101888 | 9/2007 |
| WO | WO2010141779 | 12/2010 |

OTHER PUBLICATIONS

Goto, Masatoshi, et al., "The Mechanism of Binding of Glucoamylase I from *Aspergillus awamori* var. kawachi to Cyclodextrins and Raw Starch," Biosci. Biotech. Biochem., 1994, p. 49-54, vol. 58, No. 1.

Hamilton, Lynn M., et al., "Review: cyclodextrins and their interaction with amylolytic enzymes," Enzyme and Microbial Technology, 2000, p. 561-567, vol. 26, Elsevier.

Higgins, Desmond G., et al., "Fast and sensitive multiple sequence alignments on a microcomputer," Cabios Communications, 1989, p. 151-153, vol. 5, No. 2, IRL Press.

Iizuka, Hiroshi, et al, "Studies on the Genus Monascus. I. Purification and Properties of Two forms of Glucoamylase from Monascus Kaoliang NOV. SP. F-1," J. Gen. Appl. Microbiol., 1977, p. 217-230, vol. 23.

Iizuka, Hiroshi, et al., "Studies on the Genus Monascus II. Substrate Specificity of Two Glucoamylases Obtained from Monascus Kaoliang F-1," J. Gen. Appl. Microbiol., 1978, p. 185-192, vol. 24.

International Search Report and Written Opinion dated Mar. 4, 2013, issued in International Application No. PCT/EP2012/076352, filed Dec. 20, 2012.

Karlin, Samuel, et al., "Applications and statistics for multiple high-scoring segments in molecular sequences," Proc. Natl. Acad. Sci. USA, 1993, p. 5873-5877, vol. 90.

Minshull, Jeremy, et al., "Engineered protein function by selective amino acid diversification," Methods, 2004, p. 416-427, vol. 32, Elsevier Inc.

Needleman, Saul B., et al., "A General Method Applicable to the Search for Similarities in the Amnico Acid Sequence of Two Proteins," J. Mol. Biol., 1970, p. 443-453, vol. 48.

Pearson, William R., et a., "Improved tools for biological sequence comparison," Proc. Natl. Acad. Sci. USA, 1988, p. 2444-2448, vol. 85.

Smith, Temple F., et al., "Comparison of Biosequences," Advances in Applied Mathematics, 1981, p. 482-489, vol. 2.

\* cited by examiner

SEQUENCE LISTING

```
<160> NUMBER OF SEQ ID NOS: 17

<210> SEQ ID NO 1
<211> LENGTH: 2175
<212> TYPE: DNA
<213> ORGANISM: Monascus kaoliang

<400> SEQUENCE: 1
atggtgaaga tcagcataaa tcccatcttg aaacggacat tccctctatc agtgctgctg      60
gcgccgctcc tcgcagcctg tcttggggct tcaaacctag ctcagatcgc tgttgccgct     120
gcaacatcgg cggagtcaag tgctgcgtct gattccttag attcatggct ggccagagag     180
actccatatg cccttgatgg aattttaaat aacatcggcc cagacggcgc gaaggctgtg     240
ggtgcagtct ctggcgtggt ggttgcgagt ccgagcaaga gtaatccgga ttgtgagtat     300
tctcgtattt ccagccccca acgtcaagtg catctatagc aaagaaagaa aaagctcatg     360
ctaatggatg tatctgtata tatttctaca cttggactcg tgacgctgct ctgactgtta     420
aatgtctgac cgacctcttc ctggtcaatg gtgacgtgaa tctgcagtcg cagatccaga     480
actacatcag ccgccaggca tatttgcaga ccgtatccaa tccatctggt gacctgtcga     540
ctgggggact tggtgagccc aaattcgagg ttgatggcgc tgcatttacc ggttcctggg     600
gccgtcctca acgagatggg cctgcgttga gggctacggc tctgattgct tatgccaatt     660
ggctcattgt aggtgtttgc atgttggatt ttcttttctt tctaatataa tcttctcttg     720
ttgttacttg ctaacttcca tctacagagc aatggacaga cctcgacggc ggagtccatt     780
gtttggccag ttgtccagaa tgacctttca tatgtgatgc agtattggaa ttcatctacc     840
tttggtttgt cgaggcctct aaaatgggac aagcattctc agctaacgta tggaaacttc     900
atgcagacct ctgggaggaa gtctacggct catcgttttt taccacggcc gtgcagcatc     960
gtgccctagt cgaaggtgcg gctttcgcca aaaagcttgg ccactcttgt cccgactgtc    1020
tctcccaggc atcgcagatc ctctgctttt tgcagtcgta ctggaccggt gcttacgtgc    1080
tctctaactt tggtggtggc cgctcaggga aggacgccaa ctcgatcctc ggagttctgc    1140
atactttcga ccccgatgca gactgcgatg ataccacttt ccagccttgt tctgcccggg    1200
cgcttgcgaa ccataaagta gttacggact cttttccggtc catctactct ctcaactcgg    1260
gtattgccca gggtcaagcc gtggctgtgg gacggtatcc cgaggacgtc taccagggag    1320
gcaatccatg gtatctctgt actttggctg cggcggagca gctctacgac gcgctgtatc    1380
aatgggatcg aatcgggtcc ttgtctataa cggacgtcag tctgggattc ttccaggacc    1440
tgtacccgtc cgctgcagta ggtgactatg cgtcttccac ggagacatac agagatatca    1500
tggcagctgt gaaggcctat gcgaatggat atatggatat tgctgtaagg agagctcctt    1560
tccatctttt ccttgtccca tgctgaaata gtgctacaga gaaagtacac acctgccaac    1620
```

-continued

```
ggcgctctag cagagcagtt ttctagagac gatggttccc cagtctcagc ggtcgatctg    1680
acctggtcgt atgcctctct tctcacggca gcagccagac gaggctccca gatgccgcca    1740
tcgtggaacg aatcttcttc caacaagcct ccatcgactt gctcagcatc ctctgcgacg    1800
ggggcctatg cctcggctac caacaccgtc tggcccacag cgtcgtgtgc ggcgacgccg    1860
acagccgtgc ctgtgcgttt caacgaactg gtcacgactt cagtcgggga taaggtagcc    1920
ctcgtggggt ccaccctgc tctggggtca tggaatgtct ctgcggccgt cgcactgagt    1980
gcagacgaat acagcagcgt cacgccccta tggcacggga cggtgagtct cccgaccaaa    2040
acgagcttcg agtataagta tgtggtgcag aaggagtctg gggaagtgga ctgggagggc    2100
ggagagaatc ggtcgtacac agtgccagag ggatgcgagg gctcttcagt gaccgtcaac    2160
gacagctgga agtag                                                     2175
```

<210> SEQ ID NO 2
<211> LENGTH: 1890
<212> TYPE: DNA
<213> ORGANISM: Monascus kaoliang

<400> SEQUENCE: 2

```
atggtgaaga tcagcataaa tcccatcttg aaacggacat ccctctatc agtgctgctg      60 gcgccgctcc tcgcagcctg tcttggggct caaacctag ctcagatcgc tgttgccgct     120
gcaacatcgg cggagtcaag tgctgcgtct gattccttag attcatggct ggccagagag     180
actccatatg cccttgatgg aatttttaaat aacatcggcc cagacggcgc gaaggctgtg    240
ggtgcagtct ctggcgtggt ggttgcgagt ccgagcaaga gtaatccgga ttatttctac    300
acttggactc gtgacgctgc tctgactgtt aaatgtctga ccgacctctt cctggtcaat    360
ggtgacgtga atctgcagtc gcagatccag aactacatca gccgccaggc atatttgcag    420
accgtatcca atccatctgg tgacctgtcg actgggggac ttggtgagcc caaattcgag    480
gttgatggcg ctgcatttac cggttcctgg ggccgtcctc aacgagatgg gcctgcgttg    540
agggctacgg ctctgattgc ttatgccaat tggctcatta gcaatggaca gacctcgacg    600
gcggagtcca ttgtttggcc agttgtccag aatgaccttt catatgtgat gcagtattgg    660
aattcatcta cctttgacct ctgggaggaa gtctacggct catcgttttt taccacggcc    720
gtgcagcatc gtgccctagt cgaaggtgcg gctttcgcca aaaagcttgg ccactcttgt    780
cccgactgtc tctcccaggc atcgcagatc ctctgctttt tgcagtcgta ctggaccggt    840
gcttacgtgc tctctaactt tggtggtggc cgctcaggga aggacgccaa ctcgatcctc    900
ggagttctgc atactttcga ccccgatgca gactgcgatg ataccacttt ccagccttgt    960
tctgcccggg cgcttgcgaa ccataaagta gttacggact cttttccggtc catctactct    1020 ctcaactcgg gtattgccca gggtcaagcc gtggctgtgg acggtatcc gaggacgtc     1080 taccagggag gcaatccatg gtatctctgt actttggctg cggcggagca gctctacgac    1140
gcgctgtatc aatgggatcg aatcgggtcc ttgtctataa cggacgtcag tctgggattc    1200
ttccaggacc tgtacccgtc cgctgcagta ggtgactatg cgtcttccac ggagacatac    1260
agagatatca tggcagctgt gaaggccgat gcgaatggat atatgggat tgctagaaag    1320 tacacacctg ccaacggcgc tctagcagag cagttttcta gagacgatgg ttccccagtc    1380
tcagcggtcg atctgacctg gtcgtatgcc tctcttctca cggcagcagc cagacgaggc    1440
tcccagatgc cgccatcgtg gaacgaatct tcttccaaca agcctccatc gacttgctca    1500
```

-continued

```
gcatcctctg cgacggggc ctatgcctcg gctaccaaca ccgtctggcc cacagcgtcg      1560
tgtgcggcga cgccgacagc cgtgcctgtg cgtttcaacg aactggtcac gacttcagtc      1620
ggggataagg tagccctcgt ggggtccacc cctgctctgg ggtcatggaa tgtctttgcg      1680
gccgtcgcac tgagtgcaga cgaatacagc agcgtcacgc ccctatggca cgggacggtg      1740
agtctcccga ccaaaacgag cttcgagtat aagtatgtgg tgcagaagga gtctggggaa      1800
gtggactggg agggcggaga gaatcggtcg tacacagtgc cagagggatg cgagggcttt      1860
tcagtgaccg tcaacgacag ctggaagtag                                       1890
```

```
<210> SEQ ID NO 3
<211> LENGTH: 581
<212> TYPE: PRT
<213> ORGANISM: Monascus kaoliang

<400> SEQUENCE: 3

Ala Ser Asp Ser Leu Asp Ser Trp Leu Ala Arg Glu Thr Pro Tyr Ala
1               5                   10                  15

Leu Asp Gly Ile Leu Asn Asn Ile Gly Pro Asp Gly Ala Lys Ala Val
            20                  25                  30

Gly Ala Val Ser Gly Val Val Ala Ser Pro Ser Lys Ser Asn Pro
        35                  40                  45

Asp Tyr Phe Tyr Thr Trp Thr Arg Asp Ala Ala Leu Thr Val Lys Cys
    50                  55                  60

Leu Thr Asp Leu Phe Leu Val Asn Gly Asp Val Asn Leu Gln Ser Gln
65                  70                  75                  80

Ile Gln Asn Tyr Ile Ser Arg Gln Ala Tyr Leu Gln Thr Val Ser Asn
                85                  90                  95

Pro Ser Gly Asp Leu Ser Thr Gly Gly Leu Gly Glu Pro Lys Phe Glu
            100                 105                 110

Val Asp Gly Ala Ala Phe Thr Gly Ser Trp Gly Arg Pro Gln Arg Asp
        115                 120                 125

Gly Pro Ala Leu Arg Ala Thr Ala Leu Ile Ala Tyr Ala Asn Trp Leu
    130                 135                 140

Ile Ser Asn Gly Gln Thr Ser Thr Ala Glu Ser Ile Val Trp Pro Val
145                 150                 155                 160

Val Gln Asn Asp Leu Ser Tyr Val Met Gln Tyr Trp Asn Ser Ser Thr
                165                 170                 175

Phe Asp Leu Trp Glu Glu Val Tyr Gly Ser Ser Phe Phe Thr Thr Ala
            180                 185                 190

Val Gln His Arg Ala Leu Val Glu Gly Ala Ala Phe Ala Lys Lys Leu
        195                 200                 205

Gly His Ser Cys Pro Asp Cys Leu Ser Gln Ala Ser Gln Ile Leu Cys
    210                 215                 220

Phe Leu Gln Ser Tyr Trp Thr Gly Ala Tyr Val Leu Ser Asn Phe Gly
225                 230                 235                 240

Gly Gly Arg Ser Gly Lys Asp Ala Asn Ser Ile Leu Gly Val Leu His
                245                 250                 255

Thr Phe Asp Pro Asp Ala Asp Cys Asp Asp Thr Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ser Leu Asn Ser Gly Ile Ala Gln Gly Gln Ala Val Ala
    290                 295                 300
```

```
Val Gly Arg Tyr Pro Glu Asp Val Tyr Gln Gly Gly Asn Pro Trp Tyr
305                 310                 315                 320

Leu Cys Thr Leu Ala Ala Glu Gln Leu Tyr Asp Ala Leu Tyr Gln
            325                 330                 335

Trp Asp Arg Ile Gly Ser Leu Ser Ile Thr Asp Val Ser Leu Gly Phe
                340                 345                 350

Phe Gln Asp Leu Tyr Pro Ser Ala Ala Val Gly Asp Tyr Ala Ser Ser
                355                 360                 365

Thr Glu Thr Tyr Arg Asp Ile Met Ala Ala Val Lys Ala Tyr Ala Asn
370                 375                 380

Gly Tyr Met Asp Ile Ala Arg Lys Tyr Thr Pro Ala Asn Gly Ala Leu
385                 390                 395                 400

Ala Glu Gln Phe Ser Arg Asp Asp Gly Ser Pro Val Ser Ala Val Asp
                405                 410                 415

Leu Thr Trp Ser Tyr Ala Ser Leu Leu Thr Ala Ala Ala Arg Arg Gly
                420                 425                 430

Ser Gln Met Pro Pro Ser Trp Asn Glu Ser Ser Ser Asn Lys Pro Pro
            435                 440                 445

Ser Thr Cys Ser Ala Ser Ser Ala Thr Gly Ala Tyr Ala Ser Ala Thr
450                 455                 460

Asn Thr Val Trp Pro Thr Ala Ser Cys Ala Ala Thr Pro Thr Ala Val
465                 470                 475                 480

Pro Val Arg Phe Asn Glu Leu Val Thr Thr Ser Val Gly Asp Lys Val
                485                 490                 495

Ala Leu Val Gly Ser Thr Pro Ala Leu Gly Ser Trp Asn Val Ser Ala
            500                 505                 510

Ala Val Ala Leu Ser Ala Asp Glu Tyr Ser Ser Val Thr Pro Leu Trp
515                 520                 525

His Gly Thr Val Ser Leu Pro Thr Lys Thr Ser Phe Glu Tyr Lys Tyr
    530                 535                 540

Val Val Gln Lys Glu Ser Gly Glu Val Asp Trp Glu Gly Gly Glu Asn
545                 550                 555                 560

Arg Ser Tyr Thr Val Pro Glu Gly Cys Glu Gly Ser Ser Val Thr Val
                565                 570                 575

Asn Asp Ser Trp Lys
            580

<210> SEQ ID NO 4
<211> LENGTH: 2021
<212> TYPE: DNA
<213> ORGANISM: Monascus kaoliang

<400> SEQUENCE: 4
atggtgaaga tcagcataaa tcccatcttg aaacggacat tccctctatc agtgctgctg      60
gcgccgctcc tcgcagcctg tcttggggct tcaaacctag ctcagatcgc tgttgccgct     120
gcaacatcgg cggagtcaag tgctgcgtct gattccttag attcatggct ggccagagag     180
actccatatg cccttgatgg aattttaaat aacatcggcc agacggcgc gaaggctgtg      240 ggtgcagtct ctggcgtggt ggttgcgagt ccgagcaaga gtaatccgga ttgtgagtat     300
tctcgtattt ccagccccca acgtcaagtg catctatagc aaagaaagaa aaagctcatg     360
ctaatggatg tatctgtata tatttctaca cttggactcg tgacgctgct ctgactgtta     420
aatgtctgac cgacctcttc ctggtcaatg gtgacgtgaa tctgcagtcg cagatccaga     480
actacatcag ccgccaggca tatttgcaga ccgtatccaa tccatctggt gacctgtcga     540
```

```
ctgggggact tggtgagccc aaattcgagg ttgatggcgc tgcatttacc ggttcctggg      600
gccgtcctca acgagatggg cctgcgttga gggctacggc tctgattgct tatgccaatt      660
ggctcattgt aggtgtttgc atgttggatt ttcttttctt tctaatataa tcttctcttg      720
ttgttacttg ctaacttcca tctacagagc aatggacaga cctcgacggc ggagtccatt      780
gtttggccag ttgtccagaa tgacctttca tatgtgatgc agtattggaa ttcatctacc      840
tttggtttgt cgaggcctct aaaatgggac aagcattctc agctaacgta tggaaacttc      900
atgcagacct ctgggaggaa gtctacggct catcgttttt taccacggcc gtgcagcatc      960
gtgccctagt cgaaggtgcg gctttcgcca aaaagcttgg ccactcttgt cccgactgtc     1020
tctcccaggc atcgcagatc ctctgctttt tgcagtcgta ctggaccggt gcttacgtgc     1080
tctctaactt tggtggtggc cgctcaggga aggacgccaa ctcgatcctc ggagttctgc     1140
atactttcga ccccgatgca gactgcgatg ataccacttt ccagccttgt tctgcccggg     1200
cgcttgcgaa ccataaagta gttacggact cttccggtc catctactct ctcaactcgg     1260
gtattgccca gggtcaagcc gtggctgtgg acggtatcc cgaggacgtc taccagggag     1320
gcaatccatg gtatctctgt actttggctg cggcggagca gctctacgac gcgctgtatc     1380
aatgggatcg aatcgggtcc ttgtctataa cggacgtcag tctgggattc ttccaggacc     1440
tgtacccgtc cgctgcagta ggtgactatg cgtcttccac ggagacatac agagatatca     1500
tggcagctgt gaaggcctat gcgaatggat atatggatat tgctgtaagg agagctcctt     1560
tccatctttt ccttgtccca tgctgaaata gtgctacaga gaaagtacac acctgccaac     1620
ggcgctctag cagagcagtt tctagagac gatggttccc cagtctcagc ggtcgatctg     1680
acctggtcgt atgcctctct tctcacggca gcagccagac gaggctccca gatgccgcca     1740
tcgtggaacg aatcttcttc caacaagcct ccatcgactt gctcagcatc tctgcgacg     1800 gggcccatg cctcggctac caacaccgtc tggcccacag cgtcgtcacg ccctatggc     1860 acgggacggt gagtctcccg accaaaacga gcttcgagta taagtatgtg gtgcagaagg     1920
agtctgggga gtggactgg gagggcggag agaatcggtc gtacacagtg ccagagggat     1980
gcgagggctc ttcagtgacc gtcaacgaca gctggaagta g                        2021
```

```
<210> SEQ ID NO 5
<211> LENGTH: 1587
<212> TYPE: DNA
<213> ORGANISM: Monascus kaoliang

<400> SEQUENCE: 5
```

```
atggtgaaga tcagcataaa tcccatcttg aaacggacat tccctctatc agtgctgctg       60
gcgccgctcc tcgcagcctg tcttgggct tcaaacctag ctcagatcgc tgttgccgct      120
gcaacatcgg cggagtcaag tgctgcgtct gattccttag attcatggct ggccagagag      180
actccatatg cccttgatgg aattttaaat aacatcggcc cagacggcgc gaaggctgtg      240
ggtgcagtct ctggcgtggt ggttgcgagt ccgagcaaga gtaatccgga ttatttctac      300
acttggactc gtgacgctgc tctgactgtt aaatgtctga ccgacctctt cctggtcaat      360
ggtgacgtga atctgcagtc gcagatccag aactacatca gccgccaggc atatttgcag      420
accgtatcca atccatctgg tgacctgtcg actgggggac ttggtgagcc aaattcgag      480 gttgatggcg ctgcatttac cggttcctgg ggccgtcctc aacgagatgg gcctgcgttg      540
agggctacgg ctctgattgc ttatgccaat tggctcatta gcaatggaca gacctcgacg      600
```

```
gcggagtcca ttgtttggcc agttgtccag aatgaccttt catatgtgat gcagtattgg    660
aattcatcta cctttgacct ctgggaggaa gtctacggct catcgttttt taccacggcc    720
gtgcagcatc gtgccctagt cgaaggtgcg gctttcgcca aaaagcttgg ccactcttgt    780
cccgactgtc tctcccaggc atcgcagatc tctgctttt tgcagtcgta ctggaccggt    840
gcttacgtgc tctctaactt tggtggtggc cgctcaggga aggacgccaa ctcgatcctc    900
ggagttctgc atactttcga ccccgatgca gactgcgatg ataccacttt ccagccttgt    960
tctgcccggg cgcttgcgaa ccataaagta gttacggact ctttccggtc catctactct   1020
ctcaactcgg gtattgccca gggtcaagcc gtggctgtgg acggtatcc cgaggacgtc    1080
taccagggag gcaatccatg gtatctctgt actttggctg cggcggagca gctctacgac   1140
gcgctgtatc aatgggatcg aatcgggtcc ttgtctataa cggacgtcag tctgggattc   1200
ttccaggacc tgtacccgtc cgctgcagta ggtgactatg cgtcttccac ggagacatac   1260
agagatatca tggcagctgt gaaggcctat gcgaatggat atatggatat tgctagaaag   1320
tacacacctg ccaacggcgc tctagcagag cagtttttcta gagacgatgg ttccccagtc   1380
tcagcggtcg atctgacctg gtcgtatgcc tctcttctca cggcagcagc cagacgaggc   1440
tcccagatgc cgccatcgtg gaacgaatct tcttccaaca agcctccatc gacttgctca   1500
gcatcctctg cgacggggcc ctatgcctcg gctaccaaca ccgtctggcc cacagcgtcg   1560
tcacgcccct atggcacggg acggtga                                        1587
```

<210> SEQ ID NO 6
<211> LENGTH: 480
<212> TYPE: PRT
<213> ORGANISM: Monascus kaoliang

<400> SEQUENCE: 6

```
Ala Ser Asp Ser Leu Asp Ser Trp Leu Ala Arg Glu Thr Pro Tyr Ala
1               5                   10                  15

Leu Asp Gly Ile Leu Asn Asn Ile Gly Pro Asp Gly Ala Lys Ala Val
            20                  25                  30

Gly Ala Val Ser Gly Val Val Val Ala Ser Pro Ser Lys Ser Asn Pro
        35                  40                  45

Asp Tyr Phe Tyr Thr Trp Thr Arg Asp Ala Ala Leu Thr Val Lys Cys
    50                  55                  60

Leu Thr Asp Leu Phe Leu Val Asn Gly Asp Val Asn Leu Gln Ser Gln
65                  70                  75                  80

Ile Gln Asn Tyr Ile Ser Arg Gln Ala Tyr Leu Gln Thr Val Ser Asn
                85                  90                  95

Pro Ser Gly Asp Leu Ser Thr Gly Gly Leu Gly Glu Pro Lys Phe Glu
            100                 105                 110

Val Asp Gly Ala Ala Phe Thr Gly Ser Trp Gly Arg Pro Gln Arg Asp
        115                 120                 125

Gly Pro Ala Leu Arg Ala Thr Ala Leu Ile Ala Tyr Ala Asn Trp Leu
    130                 135                 140

Ile Ser Asn Gly Gln Thr Ser Thr Ala Glu Ser Ile Val Trp Pro Val
145                 150                 155                 160

Val Gln Asn Asp Leu Ser Tyr Val Met Gln Tyr Trp Asn Ser Ser Thr
                165                 170                 175

Phe Asp Leu Trp Glu Glu Val Tyr Gly Ser Ser Phe Phe Thr Thr Ala
            180                 185                 190

Val Gln His Arg Ala Leu Val Glu Gly Ala Ala Phe Ala Lys Lys Leu
```

```
                195                 200                 205
Gly His Ser Cys Pro Asp Cys Leu Ser Gln Ala Ser Gln Ile Leu Cys
    210                 215                 220

Phe Leu Gln Ser Tyr Trp Thr Gly Ala Tyr Val Leu Ser Asn Phe Gly
225                 230                 235                 240

Gly Gly Arg Ser Gly Lys Asp Ala Asn Ser Ile Leu Gly Val Leu His
                245                 250                 255

Thr Phe Asp Pro Asp Ala Asp Cys Asp Asp Thr Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ser Leu Asn Ser Gly Ile Ala Gln Gly Gln Ala Val Ala
    290                 295                 300

Val Gly Arg Tyr Pro Glu Asp Val Tyr Gln Gly Gly Asn Pro Trp Tyr
305                 310                 315                 320

Leu Cys Thr Leu Ala Ala Ala Glu Gln Leu Tyr Asp Ala Leu Tyr Gln
                325                 330                 335

Trp Asp Arg Ile Gly Ser Leu Ser Ile Thr Asp Val Ser Leu Gly Phe
            340                 345                 350

Phe Gln Asp Leu Tyr Pro Ser Ala Val Gly Asp Tyr Ala Ser Ser
        355                 360                 365

Thr Glu Thr Tyr Arg Asp Ile Met Ala Ala Val Lys Ala Tyr Ala Asn
    370                 375                 380

Gly Tyr Met Asp Ile Ala Arg Lys Tyr Thr Pro Ala Asn Gly Ala Leu
385                 390                 395                 400

Ala Glu Gln Phe Ser Arg Asp Asp Gly Ser Pro Val Ser Ala Val Asp
                405                 410                 415

Leu Thr Trp Ser Tyr Ala Ser Leu Leu Thr Ala Ala Arg Arg Gly
            420                 425                 430

Ser Gln Met Pro Pro Ser Trp Asn Glu Ser Ser Ser Asn Lys Pro Pro
        435                 440                 445

Ser Thr Cys Ser Ala Ser Ser Ala Thr Gly Pro Tyr Ala Ser Ala Thr
    450                 455                 460

Asn Thr Val Trp Pro Thr Ala Ser Ser Arg Pro Tyr Gly Thr Gly Arg
465                 470                 475                 480

<210> SEQ ID NO 7
<211> LENGTH: 18
<212> TYPE: PRT
<213> ORGANISM: Monascus kaoliang

<400> SEQUENCE: 7

Gly Ala Tyr Thr Ala Tyr Thr Thr Tyr Thr Ala Tyr Ala Cys Asn Thr
1               5                   10                  15

Gly Gly

<210> SEQ ID NO 8
<211> LENGTH: 18
<212> TYPE: PRT
<213> ORGANISM: Monascus kaoliang

<400> SEQUENCE: 8

Tyr Thr Gly Arg Thr Ala Asn Ala Cys Arg Thr Cys Asp Thr Cys Asn
1               5                   10                  15

Gly Gly
```

<210> SEQ ID NO 9
<211> LENGTH: 22
<212> TYPE: DNA
<213> ORGANISM: Artificial Sequence
<220> FEATURE:
<223> OTHER INFORMATION: DNA primer

<400> SEQUENCE: 9
ctggtcaatg gtgacgtgaa tc                                          22

<210> SEQ ID NO 10
<211> LENGTH: 24
<212> TYPE: DNA
<213> ORGANISM: Artificial Sequence
<220> FEATURE:
<223> OTHER INFORMATION: DNA primer

<400> SEQUENCE: 10
gcaatacccg agttgagaga gtag                                        24

<210> SEQ ID NO 11
<211> LENGTH: 32
<212> TYPE: DNA
<213> ORGANISM: Artificial Sequence
<220> FEATURE:
<223> OTHER INFORMATION: DNA primer

<400> SEQUENCE: 11
atgattgaca caaaaccgac tgatatcgtc tc                               32

<210> SEQ ID NO 12
<211> LENGTH: 27
<212> TYPE: DNA
<213> ORGANISM: Artificial Sequence
<220> FEATURE:
<223> OTHER INFORMATION: DNA primer

<400> SEQUENCE: 12
ctacttccag ctgtcgttga cggtcac                                     27

<210> SEQ ID NO 13
<211> LENGTH: 59
<212> TYPE: DNA
<213> ORGANISM: Artificial Sequence
<220> FEATURE:
<223> OTHER INFORMATION: DNA primer

<400> SEQUENCE: 13
gggacaagtt tgtacaaaaa agcaggctca ccatggtgaa gatcagcata aatcccatc  59

<210> SEQ ID NO 14
<211> LENGTH: 50
<212> TYPE: DNA
<213> ORGANISM: Artificial Sequence
<220> FEATURE:
<223> OTHER INFORMATION: DNA primer

<400> SEQUENCE: 14
accactttgt acaagaaagc tgggtctact tccagctgtc gttgacggtc            50

<210> SEQ ID NO 15
<211> LENGTH: 51
<212> TYPE: DNA
<213> ORGANISM: Artificial Sequence
<220> FEATURE:
<223> OTHER INFORMATION: DNA primer

<400> SEQUENCE: 15
accactttgt acaagaaagc tgggttcacc gtcccgtgcc ataggggcgt g         51

<210> SEQ ID NO 16
<211> LENGTH: 60
<212> TYPE: DNA
<213> ORGANISM: Artificial Sequence
<220> FEATURE:
<223> OTHER INFORMATION: DNA primer

<400> SEQUENCE: 16
gggacaagtt tgtacaaaaa agcaggctat gattgacaca aaaccgactg atatcgtctc    60

<210> SEQ ID NO 17
<211> LENGTH: 2057
<212> TYPE: DNA
<213> ORGANISM: Monascus kaoliang

<400> SEQUENCE: 17
atgattgaca caaaaccgac tgatatcgtc tcgaaaatgg tgaagatcag cataaatccc    60
atcttgaaac ggacattccc tctatcagtg ctgctggcgc cgctcctcgc agcctgtctt    120
ggggcttcaa acctagctca gatcgctgtt gccgctgcaa catcggcgga gtcaagtgct    180
gcgtctgatt ccttagattc atggctggcc agagagactc catatgccct tgatggaatt    240
ttaaataaca tcggcccaga cggcgcgaag gctgtgggtg cagtctctgg cgtggtggtt    300
gcgagtccga gcaagagtaa tccggattgt gagtattctc gtatttccag cccccaacgt    360
caagtgcatc tatagcaaag aaagaaaaag ctcatgctaa tggatgtatc tgtatatatt    420
tctacacttg gactcgtgac gctgctctga ctgttaaatg tctgaccgac ctcttcctgg    480
tcaatggtga cgtgaatctg cagtcgcaga tccagaacta catcagccgc caggcatatt    540
tgcagaccgt atccaatcca tctggtgacc tgtcgactgg gggacttggt gagcccaaat    600
tcgaggttga tggcgctgca tttaccggtt cctggggccg tcctcaacga gatgggcctg    660
cgttgagggc tacggctctg attgcttatg ccaattggct cattgtaggt gtttgcatgt    720 tggatttttct tttctttcta atataatctt ctcttgttgt tacttgctaa cttccatcta    780
cagagcaatg gacagacctc gacggcggag tccattgttt ggccagttgt ccagaatgac    840 cttcatatg tgatgcagta ttggaattca tctacctttg gtttgtcgag gcctctaaaa    900
tgggacaagc attctcagct aacgtatgga aacttcatgc agacctctgg gaggaagtct    960
acggctcatc gtttttacc acggccgtgc agcatcgtgc cctagtcgaa ggtgcggctt    1020
tcgccaaaaa gcttggccac tcttgtcccg actgtctctc ccaggcatcg cagatcctct    1080 gcttttgca gtcgtactgg accggtgctt acgtgctctc taactttggt ggtggccgct    1140
cagggaagga cgccaactcg atcctcggag ttctgcatac tttcgacccc gatgcagact    1200
gcgatgatac cactttccag ccttgttctg cccgggcgct tgcgaaccat aaagtagtta    1260
cggactcttt ccggtccatc tactctctca actcgggtat tgcccagggt caagccgtgg    1320
ctgtgggacg gtatcccgag gacgtctacc agggaggcaa tccatggtat ctctgtactt    1380
tggctgcggc ggagcagctc tacgacgcgc tgtatcaatg ggatcgaatc gggtccttgt    1440
ctataacgga cgtcagtctg ggattcttcc aggacctgta cccgtccgct gcagtaggtg    1500
actatgcgtc ttccacggag acatacgag atatcatggc agctgtgaag gcctatgcga    1560
atggatatat ggatattgct gtaaggagag ctcctttcca tcttttcctt gtcccatgct    1620

```
-continued gaaatagtgc tacagagaaa gtacacacct gccaacggcg ctctagcaga gcagttttct    1680
agagacgatg gttccccagt ctcagcggtc gatctgacct ggtcgtatgc ctctcttctc    1740
acggcagcag ccagacgagg ctcccagatg ccgccatcgt ggaacgaatc ttcttccaac    1800
aagcctccat cgacttgctc agcatcctct gcgacggggc cctatgcctc ggctaccaac    1860
accgtctggc ccacagcgtc gtcacgcccc tatggcacgg gacggtgagt ctcccgacca    1920
aaacgagctt cgagtataag tatgtggtgc agaaggagtc tggggaagtg gactgggagg    1980
gcggagagaa tcggtcgtac acagtgccag agggatgcga gggctcttca gtgaccgtca    2040
acgacagctg gaagtag                                                  2057
```

POLYPEPTIDES HAVING GLUCOAMYLASE ACTIVITY AND METHOD OF PRODUCING THE SAME

REFERENCE TO A SEQUENCE LISTING

Attached is a sequence listing comprising SEQ ID NOs: 1-17, which are herein incorporated by reference in their entirety.

FIELD OF THE INVENTION

The present invention relates to polypeptides having glucoamylase activity with improved properties and to compositions comprising these polypeptides suitable for use in the production of a food, beverage (e.g. beer), feed, or biofuel. Also described is an improved and cost-effective process for isolating glucoamylases suitable for large scale protein purification procedures. Furthermore, different methods and uses related to glucoamylases according to the invention are disclosed, such as in a brewing process.

BACKGROUND

Glucoamylases (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin).

Glucoamylases are produced by numerous strains of bacteria, fungi, and plants. Certain fungal glucoamylases are produced and secreted, such as from strains of *Aspergillus*.

Other fungi, such as *Monascus*, have a long tradition in the preparation of fermented foods. For example, *Monascus* strains have been used for the fabrication of tofu in China and Japan. Historically, the fungus has been used primarily as a food additive. The organism is typically grown on rice, dried and milled, and added as 'RotReis' to meat products. Various food ingredients are also produced by species of *Monascus*. For example, pigments used in the household and in industry are produced from *Monascus purpureus*.

*Monascus* is also used as an alternative medicine. For example, red yeast rice, which is rice infected with *Monascus purpureus*, is a natural food product that is understood to lower blood cholesterol. The active component, an HMG-CoA reductase inhibitor, lowers overall blood cholesterol as well as blood LDL cholesterol levels and may even reverse coronary artery disease. The product produced by *Monascus purpureus* has been called Monacolin K, or Cholestin (Pharmanex).

*Monascus* fermentation extract has also been claimed to act as an anti-cancer drug, as disclosed in U.S. Patent Application Publication No. 2004/0081663 A1. As disclosed in U.S. Pat. No. 6,613,365, use of *Monascus kaoliang* in animal feed is described.

JP2007097462 describes the cultivation of *Monascus purpureus* to produce liquid koji (for use in making a fermented food/beverage), which comprises detectable glucoamylase activity.

U.S. Pat. No. 4,870,014 describes the cloning of thermolabile glucoamylase from *S. diastaticus* and its expression in *S. cerevisiae* for use during the fermentation step of brewing. U.S. Pat. No. 4,318,989 describes methods for producing glucoamylase (glucoamylaseS and exo-pullulanase) from *Cladosporium resinae* for use during the fermentation step of brewing.

It is well acknowledged that glucoamylases are very important commercial enzymes, and have been used in a wide variety of applications that require the hydrolysis of starch (e.g., for producing glucose and other monosaccharides from starch). However, the bulk of commercial glucoamylase is produced by fungal strains of *Aspergillus niger*.

A significant portion of the secreted protein product from these fungal sources is alpha amylase, which is an undesirable product when the goal is the isolation of glucoamylase. The presence of these unwanted enzymes and other background proteinaceous products slow down the process of isolating the desired glucoamylase, and inevitably decreases the overall yield per batch. Therefore, a need still exists for producing and isolating a high quality yield of glucoamylase while reducing unwanted products in the production process.

The purification and properties of two forms of glucoamylase from *Monascus kaoling* were disclosed ((Iizuka et al., (1977), *J. Gen. Appl. Microbiol.*, 23(5): 217-230; Iizuka et al., (1978), *J. Gen. Appl. Microbiol.*, 24: 185-192). Both glucoamylases were stated to be stable at up to 50° C., but at temperature around 60° C.-70° C. glucoamylase activities dropped sharply. The sequences of the two forms of glucoamylases were not disclosed in this article or in later publications.

The use of glucoamylases in the hydrolysis of starch derived carbohydrate has increasing importance in the brewing industry, particularly for the production of highly attenuated (sometimes referred to as low calorie) beers. For reasons relating to product stability and legislation it is important that the added enzymatic activity is removed/inactivated in the final beer. Unfortunately this requirement is difficult to fulfill due to the thermostability of the enzymes, when the glucoamylase is derived from the usual source *Aspergillus* spp., such as *A. niger* and *A. awamori*; *Humicola* spp.; *Talaromyces* spp., such as *T. emersonii*; *Athelia* spp., such as *A. rolfsii*; *Penicillium* spp., such as *P. chrysogenum*, for example, and the enzyme is added into the fermenting vessel (FV) in the brewing process.

Although the addition of glucoamylase to the mashing vessel, or at any stage prior to wort boiling, may avoid this problem, this introduces other practical difficulties. U.S. Pat. No. 4,666,718 describes a brewing process employing a reactor comprising the brewing enzyme glucoamylase immobilised on a solid support, whereby the enzyme can be recovered from the product. U.S. Pat. No. 5,422,267A describes a brewing process employing genetically engineered yeast expressing a recombinant glucoamylase, but where the enzyme is secreted by the yeast.

Therefore, a need still exists for polypeptides for example in the form of a composition having glucoamylase activity that can be added to any stage of a conventional process for preparing a fermented beverage such as beer using conventional equipment and whose activity can safely be removed from the final product.

It would be especially efficient to add polypeptides having glucoamylase activity for example in the form of a composition into a fermentation vessel (FV) used in preparing a fermented beverage. The benefits are for example lower enzyme doses, increased starch conversion to fermentable carbohydrate (for example through low isomaltose production) and reduced yeast stress. The reason why this approach is not commonly used is that active enzymes then may be present in the final product, which is undesirable as described above. The commercially available glucoamylases are in general thermostable and the energy applied during pasteurisation of a fermented beverage is not sufficient to inactivate the enzymes. Thus, a further need exist for a thermolabile glucoamylase that may be inactivated by pasteurisation after fermentation.

SUMMARY

The present invention relates to an isolated polypeptide having glucoamylase activity selected from the group consisting of:
a) a polypeptide comprising an amino acid sequence having at least 75%, 76%, 77%, 78%, 79%, 80%, 81%, 82%, 83%, 84%, 85%, 90%, 95%, 96%, 97%, 98%, 99%, or 100% sequence identity to an amino acid sequence selected from the group consisting of the mature polypeptide of SEQ ID NO: 3 and 6;
b) a polypeptide encoded by i) the nucleic acid sequence comprised in SEQ ID NO:1 or SEQ ID NO:4, or ii) the cDNA sequence of i), or iii) the sequence of SEQ ID NO:2 or SEQ ID NO:5; or iv) by a polynucleotide that hybridizes under at least low stringency conditions with the complementary strand of i), ii), or iii);
c) a polypeptide comprising a conservative substitution, deletion and/or insertion of one or more amino acids of an amino acid sequence selected from the group consisting of the mature polypeptide of SEQ ID NO: 3 and 6;
d) a polypeptide encoded by a polynucleotide comprising a nucleotide sequence having at least 75%, 76%, 77%, 78%, 79%, 80%, 81%, 82%, 83%, 84%, 85%, 90%, 95%, 96%, 97%, 98%, 99%, or 100% identity to the mature polypeptide coding sequence of SEQ ID NO: 3 or 6; and
e) a fragment of a polypeptide of a), b) c) or d) that has glucoamylase activity.

The present invention also relates to isolated polynucleotides comprising a nucleotide sequence capable of encoding a polypeptide of the present invention.

The present invention also relates to a nucleic acid capable of expressing a polypeptide of the present invention. The present invention further relates to an expression vector such as a recombinant expression vector and host cell such as an recombinant host cell comprising the nucleic acid or capable of expressing a polypeptide of the present invention. The present invention also relates to a host cell having heterologous expression of a polypeptide of the present invention. The present invention further relates to methods of isolating, producing and/or expressing a polypeptide of the present invention.

The present invention also relates to a composition comprising one or more polypeptide(s) of the present invention.

The present invention also relates to the use of a polypeptide or a composition of the present invention in a fermentation, wherein said polypeptide or composition is added before or during a fermentation step.

The present invention also relates to the use of a thermolabile polypeptide of the present invention to enhance the production of fermentable sugars in the fermentation step of a brewing process.

The present invention also relates to method which comprises adding a polypeptide or a composition of the invention before or during a fermentation step.

The present invention also relates to a fermented beverage wherein the fermented beverage is produced by a method of the present invention.

The present invention also relates to a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a polypeptide or a composition of the present invention.

The present invention also relates to a kit comprising a polypeptide, or a composition of the present invention; and instructions for use of said polypeptide or composition.

DETAILED DESCRIPTION

Figure 1:
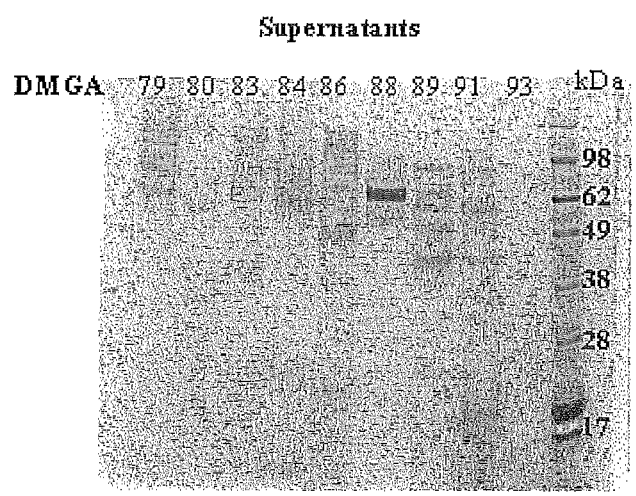
FIG. 1 depicts an SDS-PAGE analysis of the fermentation broth of various wild type fungal strains, including *Monascus kaoliang*.

Glucoamylases are commercially important enzymes in a wide variety of applications that require the hydrolysis of starch. Disclosed herein is polypeptides having glucoamylase activity based on characterization of *Monascus kaoliang* derived glucoamylase MkGA I and MkGA II, including the amino acid sequences and DNA sequences encoding glucoamylase MkGA I and MkGA II, purified from *Monascus kaoliang*. Also described is an improved and cost-effective process for isolating the herein disclosed glucoamylases, or variants thereof, suitable for large scale protein purification procedures.

Furthermore, it is described herein that especially one of the two glucoamylases from *Monascus kaoliang*, MkGA I, and variants thereof are very useful for addition into a fermentation vessel during for example beer fermentation because of the suitable thermolability of the enzyme which makes inactivation by pasteurisation possible.

Pasteurisation experiments have been performed on beer in lab-, pilot- and full-scale to assess the ability to inactivate the polypeptides described herein in the brewing process. Lab-scale pasteurisations were validated on bottled beer with glucoamylases in a full-scale tunnel pasteuriser (data not shown). MkGA I has shown to be significant more thermolabile than several other tested glucoamylases and may as the only tested glucoamylase be completely inactivated with less than 50 units (PU), which is the average upper limit for pasteurisation of a regular beer. Thermostability of MkGA I and MKGA II has previously been studied in buffer (Iizuka et al., (1977), *J. Gen. Appl. Microbiol.*, 23(5): 217-230; Iizuka et al., (1978), *J. Gen. Appl. Microbiol.*, 24: 185-192), however, it was observed that the stability of MkGA I is lower in beer compared to a buffered solution. MkGA I is significantly less thermostable in various kinds of degassed beers (pH 4.3-4.6) compared to the previously used 0.1M Na-Acetate buffer (pH 4.7) (Iizuka et al., (1977), *J. Gen. Appl. Microbiol.*, 23(5): 217-230; Iizuka et al., (1978), *J. Gen. Appl. Microbiol.*, 24: 185-192) resulting in complete inactivation of MkGA I in the beer but not in the acetate buffer with less than 50 PU. The present inventors have thus surprisingly found that MkGA I is sufficiently thermolabile in beer to be completely inactivated by pasteurisation and at the same time maintain high performance throughout the beer fermentation.

However, the low expression of MkGA I in *Monascus kaoliang* makes it commercially unattractive. The present inventors have thus further identified the genomic DNA sequence of MkGA I including the specific signal peptide sequence that together enables heterologous expression of for example MkGA I and MkGA II, such as expression in *Trichoderma reesei*.

1. DEFINITIONS

Unless defined otherwise, all technical and scientific terms used herein have the same meaning as commonly understood by one of ordinary skill in the art to which this disclosure belongs. Singleton et al., Dictionary of Microbiology And Molecular Biology, 2$^{nd}$ ed., John Wiley and Sons, New York (1994), and Hale & Markham, The Harper Collins Dictionary Of Biology, Harper Perennial, N.Y. (1991) provide one of skill with the general meaning of many of the terms used herein. Still, certain terms are defined below for the sake of clarity and ease of reference.

As used herein, the term "glucoamylase" (EC 3.2.1.3) refers to an enzyme that catalyzes the release of D-glucose from the non-reducing ends of starch and related oligo- and polysaccharides.

As used herein, the term "MkGA" refers to the mixture of both glucoamylase variants MkGA I and MkGA II produced from the fermentation of *Monascus kaoliang*.

As used herein, the term "MkGA I" refers to a smaller glucoamylase variant from *Monascus kaoliang* without a starch binding domain (SBD).

As used herein, the term "MkGA II" refers to a glucoamylase variant from *Monascus kaoliang* which has a starch binding domain (SBD).

As used herein, a "homologous sequence" and "sequence identity" with regard to a nucleic acid or polypeptide sequence means having about at least 100%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to a nucleic acid sequence or polypeptide sequence when optimally aligned for comparison, wherein the function of the candidate nucleic acid sequence or polypeptide sequence is essentially the same as the nucleic acid sequence or polypeptide sequence the candidate homologous sequence is being compared with. In some embodiments, homologous sequences have between at least about 85% and 100% sequence identity, while in other embodiments there is between about 90% and 100% sequence identity, and in other embodiments, there is at least about 95% and 100% sequence identity.

Homology is determined using standard techniques known in the art (see e.g., Smith and Waterman, *Adv. Appl. Math.* 2: 482 (1981); Needleman and Wunsch, J. Mol. Biol. 48: 443 (1970); Pearson and Lipman, *Proc. Natl. Acad. Sci. USA* 85: 2444 (1988); programs such as GAP, BESTHT, FASTA, and TFASTA in the Wisconsin Genetics Software Package (Genetics Computer Group, Madison, Wis.); and Devereux el al., *Nucleic Acid Res.*, 12: 387-395 (1984)).

The "percent (%) nucleic acid sequence identity" or "percent (%) amino acid sequence identity" is defined as the percentage of nucleotide residues or amino acid residues in a candidate sequence that is identical with the nucleotide residues or amino acid residues of the starting sequence. The sequence identity can be measured over the entire length of the starting sequence Homologous sequences are determined by known methods of sequence alignment. A commonly used alignment method is BLAST described by Altschul et al., (Altschul et al., *J. Mol. Biol.* 215: 403-410 (1990); and Karlin et al, *Proc. Natl. Acad. Sci. USA* 90: 5873-5787 (1993)). A particularly useful BLAST program is the WU-BLAST-2 program (see Altschul et al, *Meth. Enzymol.* 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Other methods find use in aligning sequences. One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, *J. Mol. Evol.* 35: 351-360 (1987)). The method is similar to that described by Higgins and Sharp (Higgins and Sharp, *CABIOS* 5: 151-153 (1989)). Useful PILEUP parameters including a default gap weight of 3.00, a default gap length weight of 0.10, and weighted end gaps.

In another aspect, the percentage of identity of one amino acid sequence with, or to, another amino acid sequence is determined by the use of the protein-protein Blast search (http://blast.ncbi.nlm.nih.gov) with default settings: score matrix: blosum62, non-redundant protein sequences database and the blast algorithm

| Settings | Expect threshold | 10 |
|---|---|---|
| | Max matches in a query range | 0 |
| | Gap opening penalty | 11 |
| | Gap extension penalty | 1 |
| | Compositional adjustment: Conditional compositional score matrix adjustment | |
| | Mask and filters | No |

The term "optimal alignment" refers to the alignment giving the highest percent identity score.

As used herein, the terms "glucoamylase variant" or "variant" are used in reference to glucoamylases that are similar to a glucoamylase sequence (e.g., the *Monascus kaoliang* glucoamylase I and II sequences) but have at least one substitution, deletion, or insertion in their amino acid sequence that makes them different in sequence from glucoamylase I and/or II. In some cases, they have been manipulated and/or engineered to include at least one substitution, deletion, or insertion in their amino acid sequence that makes them different in sequence from glucoamylase I and/or II.

As used herein the term "catalytic domain" refers to a structural region of a polypeptide, which contains the active site for the catalysis of substrate hydrolysis.

The term "linker" refers to a short amino acid sequence generally having between 3 and 40 amino acids residues that covalently bind an amino acid sequence comprising a starch binding domain with an amino acid sequence comprising a catalytic domain.

The term "starch binding domain" (SBD) refers to an amino acid sequence that binds preferentially to a starch substrate. It is well known for a person skilled in the art how to identify a SBD—the SBD is an example of a carbohydrate-binding modules (CBM) and CBMs have been classified into the CBM families using a sequence-based classification system (http://www.cazy.orci/Carbohydrate-Binding-Modules.html). In addition, it is well known for a person skilled in the art to isolate materials containing for example an SBD using raw starch or beta-cyclodextrin affinity chromatography (Hamilton et al. (2000) Enzyme and Microbial Technology 26 p 561-567). In one aspect, the domain definition of SBD is adopted from the Pfam database (http://pfam.sancier.ac.uk/ or www.sanqer.ac.uk/resources/databases/pfam.html) which database of protein domain families are generated from sequence similarity. Thus, in one aspect the SBD is as defined by the Carbohydrate binding module 20 family in the Pfam database As used herein, the term "fragment" is defined as a polypeptide having one or more (several) amino acids deleted from the amino and/or carboxyl terminus for example of the polypeptide of SEQ ID NO:3 or 6; wherein the fragment has glucoamylase activity. In one aspect, the fragment has one or more (several) amino acids deleted from the amino terminus of SEQ ID NO:3. In one aspect, the polypeptide contains fewer residues in the N- or C-terminus compared to wildtype and in the case of MkGA I also compared to MkGA II.

In one aspect, a polypeptide as described herein has at the most 480, 481, 482, 483, 484, 485, 486, 487, 488, 489, 490, 495, 500, 505, 507, 515, 525, 535, 545, 555, 565 or 573 amino acid residues.

As used herein the term "truncated" refers to a polypeptide that compared to a wild type protein (or another variant) does not achieve its full translated length and is therefore missing some of the amino acids present in the wild type protein. Truncation is normally brought about by a premature termination mutation, but could be caused by another mechanism—such as a post-translational modification.

As used herein, the terms "mutant sequence" and "mutant gene" are used interchangeably and refer to a polynucleotide sequence that has an alteration in at least one codon occurring in a host cell's parent sequence. The expression product of the mutant sequence is a variant protein with an altered amino acid sequence relative to glucoamylase I and/or II. The expression product may have an altered functional capacity (e.g., enhanced enzymatic activity or greater thermostability).

The term "property" or grammatical equivalents thereof in the context of a polypeptide, as used herein, refers to any characteristic or attribute of a polypeptide that can be selected or detected. These properties include, but are not limited to, oxidative stability, substrate specificity, catalytic activity, thermal stability, pH activity profile, resistance to proteolytic degradation, $K_M$, $K_{CAT}$, $K_{CAT}/K_M$ ratio, protein folding, ability to bind a substrate and ability to be secreted.

The term "property" of grammatical equivalent thereof in the context of a nucleic acid, as used herein, refers to any characteristic or attribute of a nucleic acid that can be selected or detected. These properties include, but are not limited to, a property affecting gene transcription (e.g., promoter strength or promoter recognition), a property affecting RNA processing (e.g., RNA splicing and RNA stability), a property affecting translation (e.g., regulation, binding of mRNA to ribosomal proteins).

The terms "thermally stable" and "thermostable" refer to glucoamylase variants of the present disclosure that retain a specified amount of enzymatic activity after exposure to a temperature over a given period of time under conditions prevailing during the hydrolysis of starch substrates, for example, while exposed to altered temperatures.

The term "enhanced stability" in the context of a property such as thermostability refers to a higher retained catalytic activity, or starch hydrolytic activity however measured, over time as compared to glucoamylase I and/or II.

The term "thermolabile glucoamylase" refers to a glucoamylase of the present disclosure that loses detectable hydrolytic enzymatic activity after exposure to a temperature over a given period of time under conditions prevailing during pasteurisation of the product of a brewing process. The precise conditions of pasteurization (e.g. Pasteurization Units) will depend on the type of beer produced by the brewing process. Loss of detectable hydrolytic activity of the thermolabile glucoamylase in a pasteurized beer may be detected using a glucoamylase enzyme assay as described herein and defined by loss of activity measured by that assay. An example of a thermolabile glucoamylase is a glucoamylase having SEQ ID NO: 6.

The term "specific activity" is defined as the activity per mg of glucoamylase protein. In some embodiments, the activity for glucoamylase is determined by an ethanol assay and expressed as the amount of glucose that is produced from the starch substrate. In some embodiments, the protein concentration can be determined using the Caliper assay.

The terms "active" and "biologically active" refer to a biological activity associated with a particular protein. It follows that the biological activity of a given protein refers to any biological activity typically attributed to that protein by those skilled in the art. For example, an enzymatic activity associated with a glucoamylase is hydrolytic and, thus an active glucoamylase has hydrolytic activity.

As used herein, the term "glucoamylase activity" refers to the activity of an enzyme that catalyzes the release of D-glucose from the non-reducing ends of starch and related oligo- and polysaccharides. In particular, glucoamylase activity may be assayed by the 3,5-dinitrosalicylic acid (DNS) method (see Goto et al., *Biosci. Biotechnol. Biochem.* 58:49-54 (1994)).

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA, or recombinant expression cassette can be incorporated into a plasmid, chromosome, mitochondrial DNA, plastid DNA, virus, or nucleic acid fragment. Typically, the recombinant expression cassette portion of an expression vector, DNA construct, or transforming DNA includes, among other sequences, a nucleic acid sequence to be transcribed, and a promoter. In some embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes, and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction.

As used herein, the terms "transformed" and "stably transformed" refers to a cell that has a non-native (heterologous) polynucleotide sequence integrated into its genome or as an episomal plasmid that is maintained for at least two generations.

As used herein, the terms "selectable marker" and "selective marker" refer to a nucleic acid (e.g., a gene) capable of expression in host cells that allows for ease of selection of those hosts containing the vector. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "promoter" refers to a nucleic acid sequence that functions to direct transcription of a downstream gene. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), can be operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein the term "gene" refers to a polynucleotide (e.g., a DNA segment), that encodes a polypeptide and includes regions preceding and following the coding regions, as well as intervening sequences (introns) between individual coding segments (exons).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm–5° C. (5° C. below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5× SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denaturated sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous or homologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

In one embodiment, mutated DNA sequences are generated with site saturation mutagenesis in at least one codon and/or nucleotide. In another embodiment, site saturation mutagenesis is performed for two or more codons. In a further embodiment, mutant DNA sequences have more than about 50%, more than 55%, more than 60%, more than 65%, more than 70%, more than 75%, more than 80%, more than 85%, more than 90%, more than 95%, or more than 98% identity with the glucoamylase I and/or II DNA sequence. In alternative embodiments, mutant DNA can be generated in vivo using any known mutagenic procedure such as, for example, radiation, nitrosoguanidine, and the like. The desired DNA sequence can then be isolated and used in the methods provided herein.

As used herein, "heterologous protein" refers to a protein or polypeptide that does not naturally occur in the host cell.

An enzyme is "over-expressed" in a host cell if the enzyme is expressed in the cell at a higher level than the level at which it is expressed in a corresponding wild-type cell.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the disclosure are described by the following nomenclature: [original amino acid residue/position/substituted amino acid residue]. For example, the substitution of leucine for arginine at position 76 is represented as R76L. When a position suitable for substitution is identified herein without a specific amino acid suggested, it is to be understood that any amino acid residue may be substituted for the amino acid residue present in the position.

A "prosequence" is an amino acid sequence between the signal sequence and mature protein that is necessary for the secretion of the protein. Cleavage of the pro sequence will result in a mature active protein.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Host strain" or "host cell" refers to a suitable host for an expression vector comprising DNA according to the present disclosure.

The terms "derived from" and "obtained from" refer to not only a glucoamylase produced or producible by a strain of the organism in question, but also a glucoamylase encoded by a DNA sequence isolated from such strain and produced in a host organism containing such DNA sequence. Additionally, the term refers to a glucoamylase that is encoded by a DNA sequence of synthetic and/or cDNA origin and that has the identifying characteristics of the glucoamylase in question.

A "derivative" within the scope of this definition generally retains the characteristic hydrolyzing activity observed in glucoamylase I and/or II to the extent that the derivative is useful for similar purposes as the wild-type, native or parent form. Functional derivatives of glucoamylases encompass naturally occurring, synthetically or recombinantly produced peptides or peptide fragments that have the general characteristics of the glucoamylases of the present disclosure.

The term "isolated" refers to a material that is removed from the natural environment if it is naturally occurring. A "purified" protein refers to a protein that is at least partially purified to homogeneity. In some embodiments, a purified protein can be more than about 10% pure, optionally more than about 20% pure, and optionally more than about 30% pure, as determined by SDS-PAGE. Further aspects of the disclosure encompass the protein in a highly purified form (i.e., more than about 40% pure, more than about 60% pure, more than about 80% pure, more than about 90% pure, more than about 95% pure, more than about 97% pure, and even more than about 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations that were not members of the predefined set of mutations. In some embodiments, the methods include those set forth in U.S. Pat. No. 6,582,914, hereby incorporated by reference. In alternative embodiments, combinatorial mutagenesis methods encompass commercially available kits (e.g., QuikChange® Multisite, Stratagene, San Diego, Calif.).

As used herein the term "composition" relates to a preparation in the form of for example a beverage, food or feed ingredient prepared according to the present invention, and may be in the form of a solution or as a solid—depending on the use and/or the mode of application and/or the mode of administration. The solid form can be either as a dried enzyme powder or as a granulated enzyme. The composition may comprise a polypeptide according to the invention, an enzyme carrier and optionally a stabilizer and/or a preservative. The enzyme carrier may be selected from the group consisting of glycerol or water. The preparation may comprise a stabilizer. The stabilizer may be selected from the group consisting of inorganic salts, polyols, sugars and combinations thereof. Further, the stabilizer may be an inorganic salt such as potassium chloride. In another aspect, the polyol is glycerol, propylene glycol, or sorbitol. The sugar is a small-molecule carbohydrate, in particular any of several sweet-tasting ones such as glucose, fructose and saccharose. In yet at further aspect, the preparation may comprise a preservative. In one aspect, the preservative is methyl paraben, propyl paraben, benzoate, sorbate or other food approved preservatives or a mixture thereof.

In the present context, the term "fermentation" refers to providing a composition such as a fermented beverage and/or substance by growing microorganisms in a culture. In the context of enzyme (e.g. glucoamylase) production, the term "fermentation" refers to a process involving the production of the enzyme in a microbial culture process. In the context of brewing, the term "fermentation" refers to transformation of sugars in a wort, by enzymes in the brewing yeast, into ethanol and carbon dioxide with the formation of other fermentation by-products.

As used herein, the "process for production of a fermented beverage" such as beer comprises in general a step of preparing a mash such as based on a grist, filtering the mash to obtain a wort and spent grain, and fermenting the wort to obtain a fermented beverage.

As used herein the term "starch and/or sugar containing plant material" refers to starch and/or sugar containing plant material derivable from any plant and plant part, including tubers, roots, stems, leaves and seeds. "Starch and/or sugar comprising plant material" can e.g. be one or more cereal, such as barley, wheat, maize, rye, sorghum, millet, or rice, and any combination thereof. The starch- and/or sugar comprising plant material can be processed, e.g. milled, malted, partially malted or unmalted. Unmalted cereal is also called "raw grain". Examples of non-cereal starch-containing plant material comprise e.g. tubers, As used herein, the term "grist" refers to any processed starch and/or sugar containing plant material suitable for mashing. The grist, as contemplated herein, may comprise any starch and/or sugar containing plant material derivable from any plant and plant part, including tubers, roots, stems, leaves and seeds. Examples of processing comprise milling and/or grinding, usually providing a material that is more coarse than flour. In the present context grist may comprise processed material from grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain. In some embodiments the grist may comprise the starch and/or sugar containing plant material obtained from cassava [*Manihot esculenta*] roots. The grist may comprise malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain.

As used herein the term "malt" is understood as any malted cereal grain, such as malted barley or wheat.

In one aspect, when using malt produced principally from selected varieties of barley in connection with production of beer, the malt has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides enzymatic activities during mashing, optionally complemented by addition of exogenous enzymes. Fifth, the malt spent grains provide a filtration medium for the separation of the wort after mashing—typically by lautering or mash filtration.

As used herein the term "adjunct" refers to any starch and/or sugar containing plant material which is not barley malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch. The starch will eventually be converted into dextrins and fermentable sugars. In one aspect, "adjunct" includes the starch and/or sugar containing plant material obtained from cassava [*Manihot esculenta*] roots.

As used herein, the term "mash" refers to an aqueous slurry of any starch and/or sugar containing plant material such as grist, e.g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

As used herein, the term "spent grains" refers to the drained solids remaining when the grist has been extracted and the wort is separated from the mash. "Spent grains" can be used e.g. as feed.

As used herein, the term "extract recovery" in the wort refers to the sum of soluble substances extracted from the grist (malt and/or adjuncts) expressed in percentage based on dry matter.

As used herein, the term "hops" refers to its use in contributing significantly to beer quality, including flavoring. In particular, hops (or hops constituents) add desirable bittering substances to the beer. In addition, the hops may act as protein precipitant, establish preservative agents and aid in foam formation and stabilization.

As used herein, the terms "beverage(s)" and "beverage(s) product" includes beers such as full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like. The term "beverage(s)" or "beverages product" also includes alternative cereal and malt beverages such as fruit flavoured malt beverages, e.g., citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like. In a further aspect, the beverage or beverage product is an alcoholic or non-alcoholic beverage, such as a cereal- or malt-based beverage like beer or whiskey, such as wine, cider, vinegar, rice wine, soya sauce, or juice.

As used herein, the term "malt beverage" includes such malt beverages as full malted beer, ale, IPA, lager, bitter, Happoshu (second beer), third beer, dry beer, near beer, light beer, low alcohol beer, low calorie beer, porter, bock beer, stout, malt liquor, non-alcoholic malt liquor and the like. The term "malt beverages" also includes alternative malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

In the context of the present invention, the term "beer" is meant to comprise any fermented wort, produced by fermentation/brewing of a starch-containing plant material, thus in particular also beer produced exclusively from malt or adjunct, or any combination of malt and adjunct.

Beer can be made from a variety of starch and/or sugar containing plant material, often cereal grains and/or malt by essentially the same process. Grain starches are believed to be glucose homopolymers in which the glucose residues are linked by either alpha-1,4- or alpha-1,6-bonds, with the former predominating.

As used herein, the term "Pilsner beer" refers to a pale bottom-fermented lager (made from Pilsner malt) usually with a more pronounced hop character than normal (e.g. helles) pale lagers.

As used herein, the term "light beers, reduced calorie beers or low calorie beers", refers to the recent, widespread popularization of brewed beverages, particularly in the U.S. market. As defined in the U.S., these highly attenuated beers have approximately 30% fewer calories than a manufacturer's "normal" beer."

As used herein, the term "non-alcoholic beer" or "low-alcohol beer" refers to a beer containing a maximum of 0.1%, 0.2%, 0.3%, 0.4%, 0.5% alcohol by volume. Non-alcoholic beer may be brewed by special methods (stopped fermentation), with special non-alcohol producing "yeasts" or by traditional methods, but during the finishing stages of the brewing process the alcohol is removed e.g. by vacuum evaporation, by taking advantage of the different boiling points of water and alcohol.

As used herein, the term "low-calorie beer" or "beer with a low carbohydrate content" is defined as a beer with a carbohydrate content of 0.75 g/100 g or less and with fermentation degree of around 90-92%.

As used herein, the term "pasteurisation" means the killing of micro-organisms in aqueous solution by heating. Implementation of pasteurisation in the brewing process is typically through the use of a flash pasteuriser or tunnel pasteuriser. As used herein, the term "pasteurisation units or PU" refers to a quantitative measure of pasteurisation. One pasteurisation unit (1 PU) for beer is defined as a heat retention of one minute at 60 degrees Celsius. One calculates that:

$PU = t \times 1.393^{(T-60)}$, where:

t=time, in minutes, at the pasteurisation temperature in the pasteuriser
T=temperature, in degrees Celsius, in the pasteuriser
[^(T-60) represents the exponent of (T-60)]

Different minimum PU may be used depending on beer type, raw materials and microbial contamination, brewer and perceived effect on beer flavour. Typically, for beer pasteurisation, 14-15 PU are required. Depending on the pasteurising equipment, pasteurisation temperatures are typically in the range of 64-72 degrees Celsius with a pasteurisation time calculated accordingly. Further information may be found in "Technology Brewing and Malting" by Wolfgang Kunze of the Research and Teaching Institute of Brewing, Berlin (VLB), 3rd completely updated edition, 2004, ISBN 3-921690-49-8.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Before the exemplary embodiments are described in more detail, it is to be understood that this disclosure is not limited to particular embodiments described, as such may, of course, vary. Although any methods and materials similar or equivalent to those described herein can be used in the practice or testing of the present disclosure, exemplary methods, and materials are now described.

As used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior invention.

2. ABBREVIATIONS

GA glucoamylase
GAU glucoamylase unit
wt weight percent
° C. degrees Centigrade
rpm revolutions per minute
aa or AA amino acid
bp base pair
kb kilobase pair
kD kilodaltons
g or gm grams μg micrograms
mg milligrams
μl and μL microliters
ml and mL milliliters
mm millimeters
micrometer
M molar
mM millimolar
μM micromolar
U units
V volts
MW molecular weight
sec(s) or s(s) second/seconds
min(s) or m(s) minute/minutes
hr(s) or h(s) hour/hours
DO dissolved oxygen
ABS Absorbance
EtOH ethanol
PSS physiological salt solution
m/v mass/volume
MTP microtiter plate
N Normal
DP1 monosaccharides
DP2 disaccharides
DP>3 oligosaccharides, sugars having a degree of polymerization greater than 3
ppm parts per million
SBD starch binding domain
CD catalytic domain
PCR polymerase chain reaction
WT wild-type
RDF Real Degree of Attenuation
SG Specific gravity
PU Pasteurisation Units
MkGA I *Monascus kaoliang* glucoamylase I
MkGA II *Monascus kaoliang* glucoamylase II
*H. jecorina Hypocrea jecorina*
*T. reesei Trichoderma reesei*
AnGA *Aspergillus Niger*

3. *MONASCUS KAOLIANG* DERIVED GLUCOAMYLASE

In one embodiment the invention relates to an isolated polypeptide having glucoamylase activity selected from the group consisting of:
a) a polypeptide comprising an amino acid sequence having at least 75%, 76%, 77%, 78%, 79%, 80%, 81%, 82%, 83%, 84%, 85%, 90%, 95%, 96%, 97%, 98%, 99%, or 100% sequence identity to an amino acid sequence selected from the group consisting of the mature polypeptide of SEQ ID NO: 3 and 6;
b) a polypeptide encoded by i) the nucleic acid sequence comprised in SEQ ID NO:1 or SEQ ID NO:4, or ii) the cDNA sequence of i), or iii) the sequence of SEQ ID NO:2 or SEQ ID NO:5; or iv) by a polynucleotide that hybridizes under at least low stringency conditions with the complementary strand of i), ii), or iii);
c) a polypeptide comprising a conservative substitution, deletion and/or insertion of one or more amino acids of an amino acid sequence selected from the group consisting of the mature polypeptide of SEQ ID NO: 3 and 6;
d) a polypeptide encoded by a polynucleotide comprising a nucleotide sequence having at least 75%, 76%, 77%, 78%, 79%, 80%, 81%, 82%, 83%, 84%, 85%, 90%, 95%, 96%, 97%, 98%, 99%, or 100% identity to the mature polypeptide coding sequence of SEQ ID NO: 3 or 6; and
e) a fragment of a polypeptide of a), b), c) or d) that has glucoamylase activity.

In one aspect, the polypeptide as contemplated herein is obtained by recombinant expression in a host cell. In a further aspect, the polypeptide as contemplated herein does not have a starch binding domain.

Another aspect is directed to the characterization of glucoamylase(s) from *Monascus kaoliang*. Glucoamylases consist of as many as three distinct structural domains, including a catalytic domain of approximately 450 residues that is structurally conserved, which is generally followed by a linker region consisting of between 30 and 80 residues, that are in turn connected to a starch binding domain of approximately 100 residues. *Monascus kaoliang* has been found to produce two forms of glucoamylase, denoted herein as glucoamylase I and II (Iizuka et al., (1977), *J. Gen. Appl. Microbiol.*, 23(5): 217-230; Iizuka et al., (1978), *J. Gen. Appl. Microbiol.*, 24: 185-192). As characterized herein, glucoamylase I (MkGA I) has the amino acid sequence appended hereto as SEQ ID NO:6, the related genomic DNA sequence encoding glucoamylase I (including the identified signal peptide sequence), appended hereto as SEQ ID NO:4, and the related cDNA sequence encoding glucoamylase I, appended hereto as SEQ ID NO:5. Additionally, glucoamylase II (MkGA II) is characterized as having the amino acid sequence appended hereto as SEQ ID NO:3, the related genomic DNA sequence encoding glucoamylase II (including the identified signal peptide sequence), appended hereto as SEQ ID NO:1, and the related cDNA sequence encoding glucoamylase II, appended hereto as SEQ ID NO:2. Results of a sequence analysis of these glucoamylase cDNA fragments demonstrated that there were two different variants of glucoamylase. A first, longer variant, referred to herein as glucoamylase II, codes for glucoamylase with a Starch Binding Domain (SBD), and a second, shorter variant, referred to herein as glucoamylase I, codes for a glucoamylase without a SBD. The difference between the two variants is a gap of 162 base pairs at the end of the linker region that separates the catalytic core and the SBD. The mature MkGA I protein contain 480 residues (SEQ ID NO:6) compared to the mature MkGA II protein having 581 residues (SEQ ID NO:3). The two proteins are highly similar and in an ungapped alignment they differ at the following 8 positions: 459, 473, 474, 475, 476, 477, 479, and 480. At these positions the amino acids composition are as follows: MkGA I: A459, C473, A474, A475, T476, P477, A479 and V480, and MkGA II: P459, S473, R474, P475, Y476, G477, G479 and R480. In a further aspect, the invention relates to a polypeptide as described here wherein the amino acid sequence comprises at least one or more amino acid residue(s) selected from the following groups: an amino acid residue selected from the group consisting of A and P at a position corresponding to position 459 in SEQ ID NO: 3 or 6, an amino acid residue selected from the group consisting of C and S at a position corresponding to position 473 in SEQ ID NO: 3 or 6, an amino acid residue selected from the group consisting of A and R at a position corresponding to position 474 in SEQ ID NO: 3 or 6, an amino acid residue selected from the group consisting of A and P at a position corresponding to position 475 in SEQ ID NO: 3 or 6, an amino acid residue selected from the group consisting of T and Y at a position corresponding to position 476 in SEQ ID NO: 3 or 6, an amino acid residue selected from the group consisting of P and G at a position corresponding to position 477 in SEQ ID NO: 3 or 6, an amino acid residue selected from the group consisting of A and G at a position corresponding to position 479 in SEQ ID NO: 6 and/or an amino acid residue selected from the group consisting of V and R at a position corresponding to position 480 in SEQ ID NO: 3 or 6.

In one aspect, the polypeptide described herein is a polypeptide, wherein the amino acid sequence has at least 75%, 76%, 77%, 78%, 79%, 80%, 81%, 82%, 83%, 84%, 85%, 90%, 95%, 96%, 97%, 98%, 99%, or 100% sequence identity to the amino acid sequence of SEQ ID NO: 6. In a further aspect, the polypeptide described herein comprises or consist of the amino acid sequence of SEQ ID NO: 3 or 6, or a fragment thereof having glucoamylase activity.

In one aspect, the polypeptide described herein has a glucoamylase activity (GAU) of at least 0.05 GAU/mg, 0.1 GAU/mg, 0.2 GAU/mg, 0.3 GAU/mg, 0.4 GAU/mg, 0.5 GAU/mg, 0.6 GAU/mg, 0.7 GAU/mg, 0.8 GAU/mg, 0.9 GAU/mg, 1 GAU/mg, 2 GAU/mg, 3 GAU/mg, 5 GAU/mg, or 10 GAU/mg.

In another aspect, the polypeptide described herein has a glucoamylase activity (GAU) of 0.05-10 GAU/mg, such as 0.1-5 GAU/mg, such as 0.5-4 GAU/mg, such as 0.7-3 GAU/mg, or such as 1-3 GAU/mg.

In yet a further aspect, the polypeptide described herein comprises or consist of the mature polypeptide of SEQ ID NO:3 or 6.

In one embodiment, essentially purified glucoamylase I or II can be produced from wild type, natural, or otherwise unmodified strains of *Monascus kaoliang*, which may provide for a non-GMO produced glucoamylase.

A further aspect relates to isolated polynucleotides encoding *Monascus kaoliang* glucoamylase I or II, or any variants thereof, such that nucleotide substitutions, deletions or insertions encode an alternative form of glucoamylase that maintains the biochemical characteristics of glucoamylase I or II, or other host glucoamylase. The polynucleotides may be prepared by established techniques known in the art. The polynucleotides may be prepared synthetically, such as by an automatic DNA synthesizer. The DNA sequence may be of mixed genomic (or cDNA) and synthetic origin prepared by ligating fragments together. The polynucleotides may also be prepared by polymerase chain reaction (PCR) using specific primers. In general, reference to such techniques is made to Minshull J. et al., *Methods* 32(4):416-427 (2004). DNA may also be synthesized by a number of commercial companies such as Geneart AG, Regensburg, Germany.

Another embodiment provides isolated polynucleotides comprising a nucleotide sequence (i) having at least 50% identity to SEQ ID NOS: 1, 2, 4 or 5, including at least 60%, at least 70%, at least 80%, at least 90%, at least 95%, and at least 99%, or (ii) being capable of hybridizing to a probe derived from the nucleotide sequence set forth in SEQ ID NOS: 1, 2, 4 or 5, under conditions of intermediate to high stringency, or (iii) being complementary to a nucleotide sequence having at least 90% sequence identity to the sequence set forth in SEQ ID NOS: 1, 2, 4 or 5. Probes useful according to the disclosure may include at least 50, 100, 150, 200, 250, 300 or more contiguous nucleotides of SEQ ID NOS: 1, 2, 4 or 5.

These isolated polynucleotides may encode the glucoamylases as contemplated herein that comprise an amino acid sequence comprising at least 50%, at least 60%, at least 70%, at least 80%, at least 90%, at least 93%, at least 95%, at least 97%, at least 98%, or at least 99% amino acid sequence identity to SEQ ID NOS: 3 or 6. Expression vectors are provided which can comprise any of the polynucleotides described herein. Also disclosed are fragments (i.e., portions) of the DNA encoding the variant glucoamylases provided herein. These fragments find use in obtaining partial length DNA fragments capable of being used to isolate or identify polynucleotides encoding mature glucoamylase enzymes as described hereinthroughout.

In yet another embodiment, a glucoamylase variant can be inserted into the organism, such as a variant having altered thermostability, such as higher thermostability and/or improved specific activity.

The conservation of structure in the glucoamylase molecule correlates with the conservation of activity and a conserved mechanism of action for all glucoamylases. Given this high homology, site specific variants of glucoamylases as contemplated herein may result in altered function, and are expected to have similar structural and therefore functional consequences in other glucoamylase variants.

Glucoamylase variants, as contemplated herein, may have amino acid substitutions at positions that are "equivalent" to the particular identified residues in *Monascus kaoliang* glucoamylase I or II (SEQ ID NOS: 6 AND 3, respectively).

"Structural identity" determines whether the amino acid residues are equivalent. Structural identity is a one-to-one topological equivalent when the two structures (three dimensional and amino acid structures) are aligned. A residue (amino acid) position of a glucoamylase is "equivalent" to a residue of *Monascus kaoliang* glucoamylase if it is either homologous (i.e., corresponding in position in either primary or tertiary structure) or analogous to a specific residue or portion of that residue in *Monascus kaoliang* glucoamylase (having the same or similar functional capacity to combine, react, or interact chemically).

To establish identity to the primary structure, the amino acid sequence of a particular glucoamylase can be compared directly to *Monascus kaoliang* glucoamylase I or II sequence, and particularly to a set of residues known to be invariant in glucoamylases for which sequence is known. After aligning the conserved residues, allowing for necessary insertions and deletions in order to maintain alignment (i.e. avoiding the elimination of conserved residues through arbitrary deletion and insertion), the residues equivalent to particular amino acids in the primary sequence of *Monascus kaoliang* glucoamylase are defined. Equivalent residues may be defined by 100% conservation with *Monascus kaoliang* glucoamylase I or II. However, alignment of greater than 75% or as little as 50% of conserved residues can be also adequate to define equivalent residues, particularly when alignment based on structural identity is included.

Structural identity involves the identification of equivalent residues between the two structures. "Equivalent residues" can be defined by determining homology at the level of tertiary structure (structural identity) for an enzyme whose tertiary structure has been determined by X-ray crystallography. Equivalent residues are defined as those for which the atomic coordinates of two or more of the main chain atoms of a particular amino acid residue of the *Monascus kaoliang* glucoamylase (N on N, CA on CA, C on C and O on O) are within 0.13 nm and optionally 0.1 nm after alignment. Alignment is achieved after the best model has been oriented and positioned to give the maximum overlap of atomic coordinates of non-hydrogen protein atoms of the glucoamylase in question to *Monascus kaoliang* glucoamylase I or II. The best model is the crystallographic model giving the lowest R factor for experimental diffraction data at the highest resolution available.

$$R \text{ factor} = \frac{\sum_{h} ||Fo(h)| - |Fc(h)||}{\sum_{h} |Fo(h)|}$$

Equivalent residues that are functionally analogous to a specific residue of *Monascus kaoliang* glucoamylase I or II are defined as those amino acids of the enzyme that may adopt a conformation such that they either alter, modify or contribute to protein structure, substrate binding or catalysis in a manner defined and attributed to a specific residue of *Monascus kaoliang* glucoamylase I or II. Further, they are those residues of the enzyme (for which a tertiary structure may be obtained by X-ray crystallography) that occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Monascus kaoliang* glucoamylase I or II. In some embodiments, variant glucoamylases as contemplated herein may have at least 50% sequence identity, at least 60% sequence identity, at least 70% sequence identity, at least 80% sequence identity, at least 85% sequence identity, at least 88% sequence identity, at least 90% sequence identity, at least 93% sequence identity, at least 95% sequence identity, at least 96% sequence identity, at least 97% sequence identity, at least 98% sequence identity and also at least 99% sequence identity with the *Monascus kaoliang* glucoamylase amino acid sequences of either SEQ ID NOS: 3 or 6.

In some embodiments, a glucoamylase variant will have more than one amino acid substitution. For example, the variant may have 1, 2, 3, 4, 5, 6, 7, 8, 9, 10, 15, 20, or 25 amino acid substitutions, deletions, or insertions as compared to *Monascus kaoliang* glucoamylase I or II. In some embodiments, a glucoamylase variant comprises a substitution, deletion, or insertion in at least one amino acid position in a position corresponding to the regions of non-conserved amino acids. As contemplated herein, the glucoamylase variants can have substitutions, deletions, or insertions in any position in the mature protein sequence.

As contemplated herein, a DNA sequence encoding glucoamylase or a glucoamylase variant can be expressed, in enzyme form, using an expression vector which typically includes control sequences encoding a promoter, operator, ribosome binding site, translation initiation signal, and, optionally, a repressor gene or various activator genes. The recombinant expression vector carrying the DNA sequence encoding a glucoamylase as contemplated herein may be any vector which may conveniently be subjected to recombinant DNA procedures. The vector may be one which, when introduced into *Monascus kaoliang*, is integrated into the genome and replicated together with the chromosome(s) into which it has been integrated. For example, the fungal cell may be transformed with the DNA construct encoding the glucoamylase, and integrating the DNA construct, in one or more copies, in the host chromosome(s). This integration is generally considered to be an advantage, as the DNA sequence is more likely to be stably maintained. Integration of the DNA constructs into the host chromosome may be performed according to conventional methods, such as by homologous or heterologous recombination.

In an embodiment incorporating use of a vector, the DNA sequence should be operably connected to a suitable promoter sequence. The promoter may be any DNA sequence which shows transcriptional activity in *Monascus kaoliang* and may be derived from genes encoding proteins either homologous or heterologous to *Monascus kaoliang*. Examples of suitable promoters for directing the transcription of the DNA sequence encoding a glucoamylase variant are, by non-limiting example only, those derived from the gene encoding *A. oryzae* TAKA amylase, the *T. reesei* cellobiohydrolase I, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, or *A. nidulans* glyceraldehyde-3-phosphate dehydrogenase A. Any expression vector as contemplated may also comprise a suitable transcription terminator and polyadenylation sequences operably connected to the DNA sequence encoding the glucoamylase or variant. Termination and polyadenylation sequences may suitably be derived from the same sources as the promoter. The vector may further comprise any DNA sequence enabling or effectuating the vector to replicate in the fungal host. The vector may also comprise additional genes, the product of which may complement a defect in the fungal host. For example, selectable markers may be incorporated to provide drug resistance. As contemplated herein, all procedures used to ligate DNA constructs encoding a glucoamylase, the promoter, terminator and other elements, respectively, and to insert them into suitable vectors containing the information necessary for replication, are those as may be understood by persons skilled in the art.

In one aspect the invention relates to a host cell having heterologous expression of a polypeptide as described herein such as a fungal cell for example of the genus *Trichoderma* such as *Trichoderma reesei*. In another aspect, the fungal cell is of the species *Hypocrea jecorina*.

In one aspect, the host cell comprises, or is preferably transformed with, a plasmid or an expression vector and is therefore capable of expressing a polypeptide as contemplated herein. In one aspect, the expression vector comprises a nucleic acid and the expression vector or plasmid as contemplated herein may comprise a promoter derived from *Trichoderma* such as a *T. reesei* cbhI-derived promoter and/or the a terminator derived from *Trichoderma* such as a *T. reesei* cbhI-derived terminator and/or one or more selective markers such as *Aspergillus nidulans* amdS and pyrG and/or one or more telomere regions allowing for a non-chromosomal plasmid maintenance in a host cell.

In one aspect, the invention relates to a method of isolating a polypeptide as described herein, the method comprising the steps of inducing synthesis of the polypeptide in a host cell having heterologous expression of said polypeptide, recovering extracellular protein secreted by said host cell, and optionally purifying the polypeptide. In another embodiment, glucoamylases can be produced from genetically modified *Monascus kaoliang*. For example, *Monascus kaoliang* may be genetically modified so as to produce enriched or overexpressed glucoamylases. Extraction methods may include those as described in the experimental examples provided below, or by any other means for extracting glucoamylases from a culture as would be understood by those skilled in the art. In one embodiment, glucoamylase may be overproduced from a genetically modified *Monascus kaoliang* strain having multiple copies of the glucoamylase gene. In another embodiment, the fungal strain may be genetically modified to inactivate other secreted enzymes. In a further embodiment, one or more copies of the glucoamylase genes may be operably linked to a different promoter, such as a highly efficient promoter region from another gene. In yet another embodiment, the fungal strain may be protease deficient or a protease minus strain.

A further aspect is directed to an improved and cost-effective process for isolating glucoamylase I and II suitable for large scale protein purification procedures. In one embodiment, the method includes the steps of growing a culture of *Monascus kaoliang*, and inducing synthesis of a glucoamylase. The DNA sequence encoding glucoamylase may be the natural or unmodified sequence, or it may be a modified sequence. *Monascus kaoliang* may be transformed by processes involving protoplast formation and transformation of the protoplasts followed by regeneration of the cell wall, according to standard methods and procedures as understood by those skilled in the art. Any standard method of transforming *Monascus kaoliang* may also be used. The medium used to cultivate *Monascus kaoliang* may be any conventional medium suitable for growing the fungal host and inducing expression of the glucoamylase or variant thereof. Suitable media are available from commercial suppliers or may be prepared according to published formulae. Glucoamylase or variants thereof secreted from *Monascus kaoliang* may conveniently be recovered from the culture medium by standard procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like. Because glucoamylase is the only dominant enzyme secreted by *Monascus kaoliang*, any additional separation steps to remove unwanted enzymes, such as alpha amylases, are either minimized or unnecessary. By removing the need to isolate the glucoamylase from other unwanted proteinaceous components, a significant efficiency and cost saving procedure is created. Additionally, the *Monascus kaoliang* host provides at least a similar yield of glucoamylase as other glucoamylase host cells, and in another embodiment, the use of *Monascus kaoliang* as a host provides a greater yield of glucoamylase or variant thereof, as compared to historical glucoamylase host cells.

In one aspect, the invention relates to a method of isolating a polypeptide as described herein, the method comprising the steps of inducing synthesis of the polypeptide in a host cell having heterologous expression of said polypeptide, recovering extracellular protein secreted by said host cell, and optionally purifying the polypeptide.

The activity and/or specific activity of any glucoamylase as contemplated herein is determined by standard methods as would be understood by those skilled in the art.

4. COMPOSITIONS AND USES

The glucoamylases as contemplated herein may be used in compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions, for example. Further, these glucoamylases may be used in baking applications, such as bread and cake production, brewing, healthcare, textile, environmental waste conversion processes, biopulp processing, and biomass conversion applications.

In some embodiments, a composition comprising a glucoamylase as contemplated herein will be optionally used in combination with any one or in any combination with the following enzymes—alpha amylases, beta-amylases, peptidases (proteases, proteinases, endopeptidases, exopeptidases), pullulanases, isoamylases, cellulases, hemicellulases, endo-glucanases and related beta-glucan hydrolytic accessory enzymes, xylanases and xylanase accessory enzymes, acetolactate decarboxylases, cyclodextrin glycotransferases, lipases, phytases, laccases, oxidases, esterases, cutinases, granular starch hydrolyzing enzymes and other glucoamylases.

In some embodiments, the composition will include the one or more further enzyme(s). In some embodiments, the composition will include the one or more further enzyme(s) selected among alpha-amylase, beta-amylase, peptidase (such as protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof.

In another embodiment, the polypeptide(s) contemplated herein and/or one or more further enzyme(s) is inactivated by pasteurisation, such as by using less than 50, 45, 40, 35, 30, 25, 24, 23, 22, 21 or 20 pasteurisation units (PU) in beer, such as Pilsner beer.

In some embodiments, the composition will include an alpha amylase such as fungal alpha amylases (e.g., *Aspergillus* sp.) or bacterial alpha amylases (e.g., *Bacillus* sp. such as *B. stearothermophilus*, (*Geobacillus stearothermophilus*), *B. amyloliquefaciens*, and *B. licheniformis*) and variants and hybrids thereof. In some embodiments, the alpha amylase is an acid stable alpha amylase. In some embodiments, the alpha amylase is *Aspergillus kawachi* alpha amylase (AkAA), see U.S. Pat. No. 7,037,704. Commercially available alpha amylases contemplated for use in the compositions of the disclosure are known and include GZYME® G-997, SPEZYME® FRED, SPEZYME® XTRA (Danisco US, Inc, Genencor Division), TERMAMYL 120-L and SUPRA (Novozymes, Biotech.).

In some embodiments, the composition will include an acid fungal protease. In a further embodiment, the composition will include the endo-protease (EC 3.4.21.26) sourced from a variant of the microorganism *Aspergillus niger* that hydrolyses peptides at the carboxyl site of proline residues disclosed in WO 2007/101888 published 13 Sep. 2007. In a further embodiment, the acid fungal protease is derived from a *Trichoderma* sp and may be any one of the proteases disclosed in US 2006/0154353, published Jul. 13, 2006, incorporated herein by reference. In a further embodiment, the composition will include a phytase from *Buttiauxiella* spp. (e.g., BP-17, see also variants disclosed in PCT patent publication WO 2006/043178). In a further embodiment, the composition will include an acetolactate decarboxylase (ALDC) EC 4.1.1.5, for example from *Bacillus licheniformis* or from the ALDC gene of *Bacillus brevis* expressed in a modified strain of *Bacillus subtilis* as disclosed in U.S. Pat. No. 4,617,273 published Oct. 14, 1986.

In other embodiments, the glucoamylases as contemplated herein may be combined with other such glucoamylases. In some embodiments, such glucoamylases will be combined with one or more glucoamylases derived from other various strains or variants of *Monascus kaoliang*, or of *Aspergillus* or variants thereof, such as *A. oryzae, A. niger, A. kawachi*, and *A. awamori*; glucoamylases derived from strains of *Humicola* or variants thereof; glucoamylases derived from strains of *Talaromyces* or variants thereof, such as *T. emersonii*; glucoamylases derived from strains of

*Athelia*, such as *A. rolfsii*; or glucoamylases derived from strains of *Penicillium*, such as *P. chrysogenum*, for example.

In particular, glucoamylases as contemplated herein may be used for starch conversion processes, and particularly in the production of dextrose for fructose syrups, specialty sugars and in alcohol and other end-product (e.g., organic acid, ascorbic acid, and amino acids) production from fermentation of starch containing substrates (G. M. A. van Beynum et al., Eds. (1985) STARCH CONVERSION TECHNOLOGY, Marcel Dekker Inc. NY). Dextrins produced using variant glucoamylase compositions of the disclosure may result in glucose yields of at least 80%, at least 85%, at least 90% and at least 95%. Production of alcohol from the fermentation of starch substrates using glucoamylases as contemplated herein may include the production of fuel alcohol or potable alcohol. In some embodiments, the production of alcohol will be greater when variant glucoamylases are used under the same conditions as wild-type glucoamylase. In some embodiments, the production of alcohol will be between about 0.5% and 2.5% better, including but not limited to 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, and 2.4% more alcohol than the wild-type glucoamylase.

In some embodiments, the glucoamylases as contemplated herein will find use in the hydrolysis of starch from various plant-based substrates, usually starch and/or sugar containing plant material, which are used for alcohol production. In some embodiments, the plant-based substrates will include corn, wheat, barley, rye, milo, rice, sugar cane, potatoes, cassava and combinations thereof. In some embodiments, the plant-based substrate will be fractionated plant material, for example a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, 3rd Ed., Eds K. A. Jacques et al., 1999, Nottingham University Press, UK. In certain embodiments, the alcohol will be ethanol. In particular, alcohol fermentation production processes are characterized as wet milling or dry milling processes. In some embodiments, the glucoamylase will be used in a wet milling fermentation process and in other embodiments the glucoamylase will find use in a dry milling process.

Dry grain milling involves a number of basic steps, which generally include: grinding, cooking, liquefaction, saccharification, fermentation, and separation of liquid and solids to produce alcohol and other co-products. Plant material and particularly whole cereal grains, such as corn, wheat, or rye are ground. In some cases the grain may be first fractionated into component parts. The ground plant material may be milled to obtain a coarse or fine particle. The ground plant material can be mixed with liquid (e.g., water and/or thin stillage) in a slurry tank. The slurry is subjected to high temperatures (e.g., 90° C. to 105° C. or higher) in a jet cooker along with liquefying enzymes (e.g., alpha amylases) to solublize and hydrolyze the starch in the grain to dextrins. The mixture can be cooled down and further treated with saccharifying enzymes, such as glucoamylases encompassed by the instant disclosure, to produce glucose. The mash containing glucose may then be fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, these glucoamylases may be used in a process for starch hydrolysis wherein the temperature of the process is between 30° C. and 75° C., in some embodiments, between 40° C. and 65° C. In some embodiments, the glucoamylase can be used in a process for starch hydrolysis at a pH of between pH 3.0 and pH 6.5. The fermentation processes in some embodiments include milling of a cereal grain or fractionated grain and combining the ground cereal grain with liquid to form a slurry that can then be mixed in a single vessel with a glucoamylase according to the disclosure and optionally other enzymes such as, but not limited to, alpha amylases, other glucoamylases, phytases, proteases, pullulanases, isoamylases or other enzymes having granular starch hydrolyzing activity and yeast to produce ethanol and other co-products (see e.g., U.S. Pat. No. 4,514,496, WO 04/081193, and WO 04/080923).

In some embodiments, the disclosure pertains to a method of saccharifying a liquid starch solution, which comprises an enzymatic saccharification step using one or more glucoamylases as contemplated herein.

In some embodiments, the disclosure pertains to a method of hydrolyzing and saccharifying gelatinised and liquefied (typically) grist starch to be used in brewing, whereby a composition comprising one or more glucoamylases as contemplated herein, is used to enhance the amount of brewers' yeast fermentable sugars obtained from the starch. A brewing process is used to produce the potable product, beer, where fermentable sugars are converted to ethanol and $CO_2$ by fermentation with brewers' yeast. The fermentable sugars are traditionally derived from starch in cereal grains, optionally supplemented with fermentable sugar sources such as glucose and maltose syrups and cane sugar. Briefly, beer production, well-known in the art, typically includes the steps of malting, mashing, and fermentation.

Historically the first step in beer production is malting—steeping, germination and drying of cereal grain (e.g. barley). During malting enzymes are produced in the germinating cereal (e.g. barley) kernel and there are certain changes in its chemical constituents (known as modification) including some degradation of starch, proteins and beta-glucans.

The malted cereal is milled to give a grist which may be mixed with a milled adjunct (e.g. non-germinated cereal grain) to give a mixed grist. The grist can also consist predominantly, or uniquely of adjunct. The grist is mixed with water and subjected to mashing; a previously cooked (gelatinised and liquefied) adjunct (the result of "adjunct cooking") may be added to the mash. The mashing process is conducted over a period of time at various temperatures in order to hydrolyse cereal proteins, degrade beta-glucans and solubilise and hydrolyse the starch. The hydrolysis of the grist starch in the malt and adjunct in traditional mashing is believed to be catalysed by two main enzymes endogenous to malted barley. Alpha-amylase, randomly cleaves alpha-1,4 bonds in the interior of the starch molecule fragmenting them into smaller dextrins. Beta-amylase sequentially cleaves alpha-1,4 bonds from the non-reducing end of the these dextrins producing mainly maltose. Both alpha- and beta-amylase are unable to hydrolyse the alpha-1,6 bonds which forms the branching points of the starch chains in the starch molecule, which results in the accumulation of limit dextrins in the mash. Malt does contain an enzyme, limit dextrinase, which catalyses the hydrolysis of alpha-1,6 bonds but it only shows weak activity at mashing temperatures due to its thermolability. After mashing, the liquid extract (wort) is separated from the spent grain solids (i.e. the insoluble grain and husk material forming part of grist). The objectives of wort separation include: • to obtain good extract recovery, • to obtain good filterability, and • to produce clear wort. Extract recovery and filterability of the wort are important in the economics of the brewing process.

The composition of the wort depends on the raw materials, mashing process and profiles and other variables. A typical wort comprises 65-80% fermentable sugars (glucose, maltose and maltotriose, and 20-35% non-fermentable limit dextrins (sugars with a higher degree of polymerization than maltotriose). An insufficiency of starch hydrolytic enzymes during mashing can arise when brewing with high levels of adjunct unmalted cereal grists. A source of exogenous enzymes, capable of producing fermentable sugars during the mashing process is thus needed. Furthermore, such exogenous enzymes are also needed to reduce the level of non-fermentable sugars in the wort, with a corresponding increase in fermentable sugars, in order to brew highly attenuated beers with a low carbohydrate content. Herein disclosed is a enzyme composition for hydrolysis of starch comprising at least one glucoamylase as contemplated herein, which can be added to the mash or used in the mashing step of a brewing process, in order to cleave alpha-1,4 bonds and/or alpha-1,6 bonds in starch grist and thereby increase the fermentable sugar content of the wort and reduce the residue of non-fermentable sugars in the finished beer. In addition, the wort, so produced may be dried (by for example spray drying) or concentrated (e.g. boiling and evaporation) to provide a syrup or powder.

The grist, as contemplated herein, may comprise any starch and/or sugar containing plant material derivable from any plant and plant part, including e.g. tubers, roots, stems, leaves and seeds as described previously. Preferably the grist comprises grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain. Most preferably the grist comprises malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain. Preferably the grist comprises adjunct, such as non-malted grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from non-malted grain or other adjunct. Adjunct comprising readily fermentable carbohydrates such as sugars or syrups may be added to the malt mash before, during or after the mashing process of the invention but is preferably added after the mashing process. A part of the adjunct may be treated with an alpha-amylase, and/or endopeptidase (protease) and/or a endoglucanase, and/or heat treated before being added to the mash. The enzyme composition for hydrolysis of starch, as contemplated herein, may include additional enzyme(s), preferably an enzyme selected from among an alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof. During the mashing process, starch extracted from the grist is gradually hydrolyzed into fermentable sugars and smaller dextrins. Preferably the mash is starch negative to iodine testing, before wort separation.

After mashing, the wort (liquid extract wort) is separated from the spent grain solids by the process of lautering or mash filtration. The objectives of wort separation include: good extract recovery; good filterability, and a clear wort (further information may be found in "Technology Brewing and Malting" by Wolfgang Kunze of the Research and Teaching Institute of Brewing, Berlin (VLB), 3rd completely updated edition, 2004, ISBN 3-921690-49-8).

Prior to the third step of the brewing process, fermentation, the wort is typically transferred to a brew kettle and boiled vigorously for 50-60 minutes. A number of important processes occur during wort boiling (further information may be found in "Technology Brewing and Malting" by Wolfgang Kunze of the Research and Teaching Institute of Brewing, Berlin (VLB), 3rd completely updated edition, 2004, ISBN 3-921690-49-8) including inactivation of the endogenous malt enzymes and any exogenous enzyme added to the mash or adjunct. The boiled wort is then cooled, pitched with brewers' yeast and fermented at temperatures ranged from 8-16° C. to convert the fermentable sugars to ethanol. A low-alcohol beer can be produced from the final beer, by a process of vacuum evaporation that serves to selectively remove alcohol. Furthermore, hops may be added to the wort.

In one aspect, the invention relates to the use of a polypeptide or a composition as contemplated herein in a fermentation, wherein said polypeptide or composition is added before or during a fermentation step. In a further aspect, said fermentation step is followed by a pasteurisation step. In one aspect, said fermented beverage is selected from the group consisting of beer such as low alcohol beer or low calorie beer. In another aspect, said polypeptide or said composition is added in combination with one or more further enzyme(s), such as selected among alpha-amylase, protease, pullulanase, isoamylase, cellulase, endoglucanase, xylanase, arabinofuranosidase, ferulic acid esterase, xylan acetyl esterase and glucoamylase, including any combination(s) thereof. In yet a further aspect, the polypeptide and/or the one or more further enzyme(s) is inactivated in the pasteurisation step.

In one aspect, the polypeptide(s) contemplated herein is added in an amount of for example 1-1000 mg pr. kg grist, such as 20-500 mg pr. kg grist, such as 30-400 mg pr. kg grist such as 40-300 mg pr. kg grist, such as 50-200 mg pr. kg grist.

In one aspect, the polypeptide(s) contemplated herein is added in an amount of for example at least 1, 50, 100, 150, 200, 300, 400, 500, 600, 700, 800, 900 or 1000 mg pr. kg. grist.

In an alternative embodiment, the invention relates to a method, such as in a method wherein a fermentation is comprised in a process for making a fermented beverage, which method comprises adding a polypeptide or a composition as described herein before or during a fermentation step, such as in a method comprising a pasteurisation step after the fermentation step or optional beer filtration step.

In one aspect, the invention relates to a method for production of a fermented beverage which comprises the following steps:
a) preparing a mash, such as obtained from a grist, where said grist for example comprises one or more of malted and/or unmalted grain, or starch-based material from another crop, and wherein the this step optionally further comprises contacting said mash with one or more further enzyme(s),
b) filtering the mash to obtain a wort, and
c) fermenting the wort to obtain a fermented beverage, and optionally a pasteurisation step (d)
wherein a polypeptide or a composition as described herein is added to:
  i. the mash of step (a) and/or
  ii. the wort of step (b) and/or
  iii. the wort of step (c).

In one aspect the one or more enzymes optionally added in step a may be selected among a starch debranching enzyme, R-enzyme, limit dextrinase, alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof. In another aspect, one or more enzymes may also be added by contacting the wort of step (b) or (c) with one or more further enzyme(s), wherein the enzyme is selected among a starch debranching enzyme, isoamylase and limit dextrinase, including any combinations thereof.

In an alternative embodiment, the disclosure pertains to a method of enhancing the amount of fermentable sugars in the wort, using a composition comprising one or more glucoamylases as contemplated herein (e.g. thermolabile glucoamylase), whereby the composition is added to the wort after it has been boiled, such that the one or more glucoamylases are active during the fermentation step. The composition can be added to the boiled wort either before, simultaneously, or after the wort is pitched with the brewers' yeast. At the end of the fermentation and maturation step the beer, which may optionally be subjected to vacuum evaporation to produce a low-alcohol beer, is then optionally filtered and/or pasteurised. An inherent advantage of this method lies in the duration of the fermentation process, which is about 6-15 days (depending on pitching rate, fermentation, temperature, etc), which allows more time for the enzymatic cleavage of non-fermentable sugars, as compared to the short mashing step (2-4 h duration). A further advantage of this method lies in the amount of the composition needed to achieve the desired decrease in non-fermentable sugars (and increase in fermentable sugars), which corresponds to a significantly lower number of units of enzymatic activity (e.g. units of glucoamylase activity) than would need to be added to the mash to achieve a similar decrease in non-fermentable sugars. In addition, it removes the difficulties often seen during wort separation, especially by lautering, when high dose rates of glucoamylase are added in the mash. In contrast to alternative sources of glucoamylase enzyme, it has surprisingly been found that the glucoamylases as contemplated herein, are sufficiently temperature sensitive, that the final heat-treatment step of the finished beer (standard pasteurisation conditions) is sufficient for its catalytic activity to be inactivated. Hence an important advantage of the composition comprising one or more glucoamylases as contemplated herein, is that it can be used to reduce the amount of non-fermentable sugars in the wort during the fermentation step of brewing in order to brew highly attenuated beers with a low carbohydrate content, and where the catalytic activity of the composition is susceptible to inactivation by the heat treatment during beer pasteurisation thereby avoiding the expense of immobilized enzyme reactors or the use of genetically engineered brewer's yeast.

The present disclosure also provides a method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a polypeptide or a composition as described herein. In another aspect, the invention also relates to a kit comprising a polypeptide, or a composition as contemplated herein; and instructions for use of said polypeptide or composition. The invention also relates to a fermented beverage produced by a method as described herein.

The present disclosure also provides an animal feed composition or formulation comprising at least one glucoamylase as contemplated herein. Methods of using a glucoamylase enzyme in the production of feeds comprising starch are provided in for example WO 03/049550 (herein incorporated by reference in its entirety). Briefly, the glucoamylase is admixed with a feed comprising starch. The glucoamylase is capable of degrading resistant starch for use by the animal.

Other objects and advantages of the present disclosure are apparent from the present specification.

5. FURTHER EMBODIMENTS ACCORDING TO THE INVENTION

Embodiment 1

An isolated polypeptide having glucoamylase activity selected from the group consisting of:
a) a polypeptide comprising an amino acid sequence having at least 75%, 76%, 77%, 78%, 79%, 80%, 81%, 82%, 83%, 84%, 85%, 90%, 95%, 96%, 97%, 98%, 99%, or 100% sequence identity to an amino acid sequence selected from the group consisting of the mature polypeptide of SEQ ID NO: 3 and 6;
b) a polypeptide encoded by i) the nucleic acid sequence comprised in SEQ ID NO:1 or SEQ ID NO:4, or ii) the cDNA sequence of i), or iii) the sequence of SEQ ID NO:2 or SEQ ID NO:5; or iv) by a polynucleotide that hybridizes under at least low stringency conditions with the complementary strand of i), ii), or iii);
c) a polypeptide comprising a conservative substitution, deletion and/or insertion of one or more amino acids of an amino acid sequence selected from the group consisting of the mature polypeptide of SEQ ID NO: 3 and 6;
d) a polypeptide encoded by a polynucleotide comprising a nucleotide sequence sequence having at least 75%, 76%, 77%, 78%, 79%, 80%, 81%, 82%, 83%, 84%, 85%, 90%, 95%, 96%, 97%, 98%, 99%, or 100% identity to the mature polypeptide coding sequence of SEQ ID NO: 3 or 6; and e) a fragment of a polypeptide of a), b), c) or d) that has glucoamylase activity.

Embodiment 2

An isolated polypeptide having glucoamylase activity comprising an amino acid sequence having at least 75%, 76%, 77%, 78%, 79%, 80%, 81%, 82%, 83%, 84%, 85%, 90%, 95%, 96%, 97%, 98%, 99%, or 100% sequence identity to an amino acid sequence selected from the group consisting of the mature polypeptide of SEQ ID NO: 3 and 6.

Embodiment 3

An isolated polypeptide having glucoamylase activity encoded by i) the nucleic acid sequence comprised in SEQ ID NO:1 or SEQ ID NO:4, or ii) the cDNA sequence of i), or iii) the sequence of SEQ ID NO:2 or SEQ ID NO:5; or iv) by a polynucleotide that hybridizes under at least low stringency conditions with the complementary strand of i), ii), or iii).

Embodiment 4

An isolated polypeptide having glucoamylase activity comprising a conservative substitution, deletion and/or insertion of one or more amino acids of an amino acid sequence selected from the group consisting of the mature polypeptide of SEQ ID NO: 3 and 6.

Embodiment 5

An isolated polypeptide having glucoamylase activity encoded by a polynucleotide comprising a nucleotide sequence having at least 75%, 76%, 77%, 78%, 79%, 80%, 81%, 82%, 83%, 84%, 85%, 90%, 95%, 96%, 97%, 98%, 99%, or 100% identity to the mature polypeptide coding sequence of SEQ ID NO: 3 or 6.

Embodiment 6

An isolated polypeptide having glucoamylase activity which polypeptide is a fragment of a polypeptide according to any one of embodiments 1-5.

Embodiment 7

The polypeptide according to any one of embodiments 1-6, wherein the amino acid sequence comprises at least one or more amino acid residue(s) selected from the following groups:
  a. an amino acid residue selected from the group consisting of A and P at a position corresponding to position 459 in SEQ ID NO: 3 or 6,
  b. an amino acid residue selected from the group consisting of C and S at a position corresponding to position 473 in SEQ ID NO: 3 or 6,
  c. an amino acid residue selected from the group consisting of A and R at a position corresponding to position 474 in SEQ ID NO: 3 or 6,
  d. an amino acid residue selected from the group consisting of A and P at a position corresponding to position 475 in SEQ ID NO: 3 or 6,
  e. an amino acid residue selected from the group consisting of T and Y at a position corresponding to position 476 in SEQ ID NO: 3 or 6,
  f. an amino acid residue selected from the group consisting of P and G at a position corresponding to position 477 in SEQ ID NO: 3 or 6,
  g. an amino acid residue selected from the group consisting of A and G at a position corresponding to position 479 in SEQ ID NO: 3 or 6 and/or
  h. an amino acid residue selected from the group consisting of V and R at a position corresponding to position 480 in SEQ ID NO: 3 or 6.

Embodiment 8

The polypeptide according to any one of embodiments 1-7, wherein the amino acid sequence has at least 75%, 76%, 77%, 78%, 79%, 80%, 81%, 82%, 83%, 84%, 85%, 90%, 95%, 96%, 97%, 98%, 99%, or 100% sequence identity to the amino acid sequence of SEQ ID NO: 3 or 6.

Embodiment 9

The polypeptide according to any one of embodiments 1-8, comprising or consisting of the amino acid sequence of SEQ ID NO: 3 or 6, or a fragment thereof having glucoamylase activity.

Embodiment 10

The polypeptide according to any one of embodiments 1-9, comprising or consisting of the mature polypeptide of SEQ ID NO:3 or 6.

Embodiment 11

The polypeptide according to any one of embodiments 1-10, wherein the percentage of identity of one amino acid sequence with, or to, another amino acid sequence is determined by the use of the protein-protein Blast search (http://blastncbi.nlm.nih.gov) with default settings: score matrix: blosum62, non-redundant protein sequences database and the blast algorithm

| Settings | Expect threshold | 10 |
|---|---|---|
| | Max matches in a query range | 0 |
| | Gap opening penalty | 11 |
| | Gap extension penalty | 1 |
| | Compositional adjustment: Conditional compositional score matrix adjustment | |
| | Mask and filters | No |

Embodiment 12

The polypeptide according to any one of embodiments 1-11, which polypeptide is inactivated by pasteurisation such as using less than 50, 45, 40, 35, 30, 25, 24, 23, 22, 21 or 20 pasteurisation units (PU) in beer.

Embodiment 13

The polypeptide according to any one of embodiments 1-12, which polypeptide has a glucoamylase activity (GAU)

of 0.05-10 GAU/mg, such as 0.1-5 GAU/mg, such as 0.5-4 GAU/mg, such as 0.7-3 GAU/mg, or such as 1-3 GAU/mg.

Embodiment 14

The polypeptide according to any one of embodiments 1-13, wherein the polypeptide does not have a SBD.

Embodiment 15

The polypeptide according to any one of embodiments 1-14 having at the most 480, 481, 482, 483, 484, 485, 486, 487, 488, 489, 490, 495, 500, 505, 507, 515, 525, 535, 545, 555, 565 or 573 amino acid residues.

Embodiment 16

The polypeptide according to any one of embodiments 1-15, wherein the polypeptide is truncated compared to SEQ ID NO:3.

Embodiment 17

The polypeptide according to any one of the embodiments 1-16, which is obtained by recombinant expression in a host cell.

Embodiment 18

A nucleic acid capable of encoding a polypeptide according to any one of embodiments 1-17.

Embodiment 19

An expression vector comprising a nucleic acid according to embodiment 18, or capable of expressing a polypeptide according to any one of embodiments 1-17.

Embodiment 20

The expression vector or plasmid as defined in embodiment 19 comprising a promoter derived from *Trichoderma* such as a *T. reesei* cbhI-derived promoter.

Embodiment 21

The expression vector or plasmid as defined in embodiment 19 comprising a terminator derived from *Trichoderma* such as a *T. reesei* cbhI-derived terminator.

Embodiment 22

The expression vector or plasmid according to embodiment 19 comprising one or more selective markers such as *Aspergillus nidulans* amdS and pyrG.

Embodiment 23

The expression vector or plasmid according to embodiment 19 comprising one or more telomere regions allowing for a non-chromosomal plasmid maintenance in a host cell.

Embodiment 24

A host cell having heterologous expression of a polypeptide as defined in any one of embodiments 1-17.

Embodiment 25

The host cell as defined in any one of embodiments 17 and 24, wherein the host cell is a fungal cell.

Embodiment 26

The host cell according to embodiment 25, wherein the fungal cell is of the genus *Trichoderma*.

Embodiment 27

The host cell according to embodiment 26, wherein the fungal cell is of the species *Trichoderma* reesei.

Embodiment 28

The host cell according to embodiment 26, wherein the fungal cell is of the species *Hypocrea jecorina*.

Embodiment 29

A host cell comprising, preferably transformed with, a plasmid or an expression vector as defined in any one of embodiments 19-23.

Embodiment 30

A method of isolating a polypeptide as defined in any one of embodiments 1-17, the method comprising the steps of inducing synthesis of the polypeptide in a host cell as defined in any one of embodiments 25-29 having heterologous expression of said polypeptide and recovering extracellular protein secreted by said host cell, and optionally purifying the polypeptide.

Embodiment 31

A method for producing a polypeptide as defined in any one of embodiments 1-17, the method comprising the steps of inducing synthesis of the polypeptide in a host cell as defined in any one of embodiments 25-29 having heterologous expression of said polypeptide, and optionally purifying the polypeptide.

Embodiment 32

A method of expressing a polypeptide as defined in any one of embodiments 1-17, the method comprising obtaining a host cell as defined in any one of embodiments 25-29 and expressing the polypeptide from said host cell, and optionally purifying the polypeptide.

Embodiment 33

The method according to any one of embodiments 30-32, wherein the polypeptide as defined in any one of embodiments 1-17 is the dominant secreted protein.

Embodiment 34

A composition comprising one or more polypeptide(s) as defined in any one of embodiments 1-17.

Embodiment 35

The composition according to embodiment 34, wherein the composition is selected from among a starch hydrolyzing composition, a saccharifying composition, a detergent composition, an alcohol fermentation enzymatic composition, and an animal feed animal feed composition.

Embodiment 36

The composition according to any one of embodiments 34-35, comprising one or more further enzyme(s).

Embodiment 37

The composition according to embodiment 36, wherein the one or more further enzyme(s) is selected among alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof.

Embodiment 38

The composition according to any one of embodiments 34-37, which polypeptide(s) and/or one or more further enzyme(s) is inactivated by pasteurisation.

Embodiment 39

The composition according to embodiment 38, wherein the polypeptide and/or the one or more further enzyme(s) is inactivated by pasteurisation such as by using less than 50, 45, 40, 35, 30, 25, 24, 23, 22, 21 or 20 pasteurisation units (PU) in beer.

Embodiment 40

Use of a polypeptide as defined in any one of embodiments 1-17 or a composition as defined in any one of embodiments 34-39 in a fermentation, wherein said polypeptide or composition is added before or during a fermentation step.

Embodiment 41

The use according to embodiment 40, wherein said fermentation step, and optional beer filtration step, is followed by a pasteurisation step.

Embodiment 42

The use according to any one of embodiments 40-41, wherein said fermentation is comprised in a process for making a fermented beverage.

Embodiment 43

The use according to any one of embodiments 40-42, wherein said fermented beverage is selected from the group consisting of beer such as low alcohol beer or low calorie beer.

Embodiment 44

The use according to any one of embodiments 40-43, wherein said polypeptide or said composition is added in combination with one or more further enzyme(s).

Embodiment 45

The use according to embodiment 44, wherein said one or more further enzyme(s) is selected among alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof.

Embodiment 46

The use according to any one of embodiments 40-45, wherein the polypeptide and/or the one or more further enzyme(s) is inactivated in the pasteurisation step.

Embodiment 47

The use according to any one of embodiments 40-46, wherein the polypeptide is added in an amount of 1-1000 mg pr. kg grist, such as 20-500 mg pr. kg grist, such as 30-400 mg pr. kg grist such as 40-300 mg pr. kg grist, such as 50-200 mg pr. kg grist.

Embodiment 48

Use of a thermolabile polypeptide to enhance the production of fermentable sugars in the fermentation step of a brewing process, wherein the polypeptide is as defined in any one of embodiments 1-17.

Embodiment 49

A method which comprises adding a polypeptide as defined in any one of embodiments 1-17 or a composition as defined in any one of embodiments 34-39 before or during a fermentation step, such as a fermentation step with yeast.

Embodiment 50

The method according to embodiment 49 comprising a pasteurisation step after the fermentation step or optional beer filtration step.

Embodiment 51

The method according to any one of embodiments 49-50, wherein said fermentation is comprised in a process for making a fermented beverage.

Embodiment 52

The method according to any one of embodiments 49-51, wherein said fermented beverage is selected from the group consisting of beer such as low alcohol beer, low calorie beer.

Embodiment 53

The method according to any one of embodiments 49-51, wherein said polypeptide or said composition is added in combination with one or more further enzyme(s).

Embodiment 54

The method according to embodiment 53, wherein said one or more further enzyme(s) is selected among alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof.

Embodiment 55

The method according to any one of embodiments 49-54, wherein the polypeptide and/or the one or more further enzyme(s) is inactivated in the pasteurisation step.

Embodiment 56

The method according to any one of embodiments 49-55, wherein the polypeptide is added in an amount of amount of 1-1000 mg pr. kg grist, such as 20-500 mg pr. kg grist, such as 30-400 mg pr. kg grist such as 40-300 mg pr. kg grist, such as 50-200 mg pr. kg grist.

Embodiment 57

The method according to any one of embodiments 49-56 for production of a fermented beverage which comprises the following steps:
a) preparing a mash,
b) filtering the mash to obtain a wort, and
c) fermenting the wort to obtain a fermented beverage, wherein a polypeptide as defined in any one of embodiments 1-17 or a composition as defined in any one of embodiments 34-39 is added to:
i. the mash of step (a) and/or
ii. the wort of step (b) and/or
iii. the wort of step (c).

Embodiment 58

The method according to embodiment 57, wherein the fermented beverage is subjected to a pasteurisation step (d).

Embodiment 59

The method according to any one of embodiments 57-58, wherein the mash in step (a) is obtained from a grist.

Embodiment 60

The method according to embodiment 57, wherein the grist comprises one or more of malted and/or unmalted grain, or starch-based material from another crop.

Embodiment 61

The method according to any one of embodiments 57-60, further comprising contacting the mash of step (a) with one or more further enzyme(s).

Embodiment 62

The method according to embodiment 61, wherein the enzyme is selected among a starch debranching enzyme, R-enzyme, limit dextrinase, alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, including any combination(s) thereof.

Embodiment 63

The method according to any one of embodiments 57-62, further comprising contacting the wort of step (b) or (c) with one or more further enzyme(s), wherein the enzyme is selected among a starch debranching enzyme, isoamylase and limit dextrinase, including any combinations thereof.

Embodiment 64

A fermented beverage wherein the fermented beverage is produced by a method as defined in any one of embodiments 49-63.

Embodiment 65

The fermented beverage according to embodiment 64, which is beer such as low alcohol beer or low calorie beer.

Embodiment 66

A method for the production of a food, feed, or beverage product, such as an alcoholic or non-alcoholic beverage, such as a cereal- or malt-based beverage like beer or whiskey, such as wine, cider, vinegar, rice wine, soya sauce, or juice, said method comprising the step of treating a starch and/or sugar containing plant material with a polypeptide according to embodiments 1-17, or a composition as defined in any one of embodiments 34-39.

Embodiment 67

A kit comprising a polypeptide according to embodiments 1-17, or a composition as defined in any one of embodiments 34-39; and instructions for use of said polypeptide or composition.

The following examples are provided and it should be understood that the various modifications can be made without departing from the spirit of the embodiments discussed.

5. EXPERIMENTAL

Example 1

Analysis of Enzyme Activity in a Fermentation Broth of *Monascus kaoliang* and Comparision with Other Microorganisms CBS302.78 was fermented in 50 mL MD medium [Casamino acids (9 g/L), $MgSO_4.7H_2O$ (1 g/L), $(NH_4)_2SO_4$ (5 g/L), $KH_2PO_4$ (4.5 g/L), $CaCl_2.2H_2O$ (1 g/L), PIPSS (33 g/L), 2.5 ml/L *T. reesei* trace elements [Citric acid (175 g/L), $FeSO_4.7H_2O$ (200 g/L), $ZnSO_4.7H_2O$ (16 g/L), $CuSO_4.5H_2O$ (3.2 g/L), $MnSO_4.H_2O$ (1.4 g/L), $H_3BO_3$ (0.8 g/L)], 500 ml 30% maltose, pH 5.5] for 7 days at 28° C. As depicted in FIG. 1, the fermentation broth of *Monascus kaoliang*, along with other wild type fungal strains as listed in Table 1, were analyzed by sodium dodecyl sulfate polyacrylamide gel electrophoresis (SDS-PAGE). All SDS_PAGE gels were run with the Invitrogen NuPAGE® Novex 10% Bis-Tris Gel 1.0 mm, 12 well (Cat# NP0302box), See-Blue® prestained Standard (Cat# LC5625) and NuPAGE® MES SDS Running Buffer (Cat# NP0002) according to the manufacturer's protocol.

A Bradford assay was used for total protein quantification. The reagent solution was Bradford Quikstart work solution (BioRad cat#500-0205). 100 µl of supernatant was placed in a fresh 96-well flat bottom plate. To each well 200 UI reagent was added and incubated for 5 minutes at room temperature. The absorbance was measured at 595 nm in a MTP-reader (Molecular Devices Spectramax 384 plus). Protein concentrations were calculated according to a Bovine Serum Albumin (BSA) (0-50 Ug/ml) standard curve.

TABLE 1

| Strain | Organism | Total. protein. (mg/ml) | Units GA/L |
|---|---|---|---|
| DMGA079 | Embellisia | 0.11 | 6.6 |
| DMGA080 | Geomyces | 0.12 | 0.05 |
| DMGA083 | Thelebolus | 0.09 | 1.4 |
| DMGA084 | Emericella desertorum | 0.28 | 0.19 |
| DMGA086 | Chaetomium vitellium | 0.43 | 0.3 |
| DMGA088 | Monascus kaoliang | 0.13 | 6.8 |
| DMGA089 | Myceliophthora thermophila | 0.32 | 0.08 |
| DMGA091 | Talaromyces emersonii | 0.67 | 0.17 |
| DMGA093 | Chaetomium atrobruneum | 0.04 | 0.04 |

Figure 2:
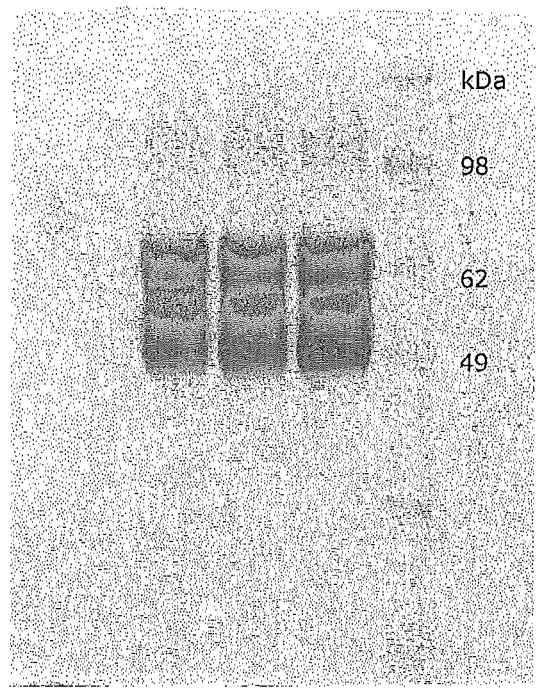
FIG. 2 depicts a SDS-PAGE analysis of the fermentation broth of *Monascus kaoliang*, showing two protein bands, one of a size similar to the size range as glucoamylases of other filamentous fungi (62 kDa), and a second of about 49 kDa.

Surprisingly, the fermentation broth of *Monascus kaoliang* showed an intense protein band at the size in the same range as glucoamylase of other filamentous fungi (62 kDa). The 50 mL fermentation of *Monascus kaoliang* was repeated, and as depicted in FIG. 2, the PAGE gel showed abundant protein bands of 62 and 49 kDA.

The two bands were isolated from the gel and analyzed by liquid chromatography-mass spectrometry (LC/MS). From the results it could be concluded that the 62 kDa band represented glucoamylase, and the 49 kDA band represented glucoamylase precursor protein.

Figure 3:
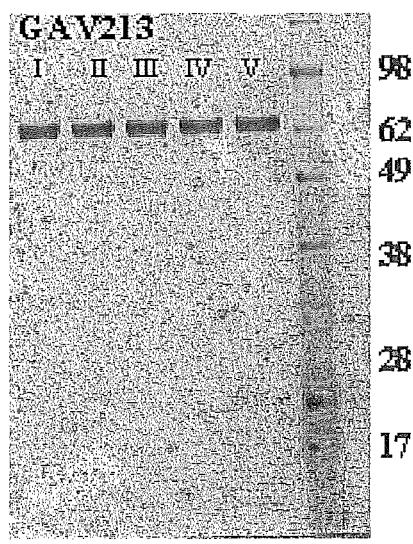
FIG. 3 depicts another SDS-PAGE analysis of fermentation broth samples of *Monascus kaoliang*, showing a protein band of about 62 kDa.

A sufficient enzyme sample was generated for small-scale application testing. Five 400 mL MD medium fermentations in 2 L shake flasks were carried out for 4 days at 28° C. The SDS-PAGE analysis of the fermentation broth is depicted in FIG. 3. The cultures were centrifuged for 30 min at 8.500 rpm in a Sorvall GS-3 Rotor, and the centrifugate was sterilized by filtration over a 0.22 µm filter (Millipore). The filtrate was concentrated using a VivaSpin 200 ultra filtration device with a 10 kDa MW cut off.

pNPG Glucoamylase Activity Assay:

Reagent solutions: NaAc buffer (200 mM sodium acetate buffer pH 4.5); Substrate (50 mM p-nitrophenyl-α-D-glucopyranoside (Sigma N-1377) in NaAc buffer (0.3 g/20 ml)) and stop solution (800 mM glycine-NaOH buffer pH 10). 30 µl filtered supernatant was placed in a fresh 96-well flat bottom MTP. To each well 50 µl NaAc buffer and 120 µl substrate was added and incubated for 30 minutes at 50° C. (Thermolab systems iEMS Incubator/shaker HT). The reaction was terminated by adding 100 µl stop solution. The absorbance was measured at 405 nm in a MTP-reader (Molecular Devices Spectramax 384 plus) and the activity was calculated using a molar extinction coefficient of 0.011 µM/cm.

The GA activity was determined as shown in Table 2 below.

TABLE 2

| Strain | Gene from: | Total protein (mg/ml) | U GA/L | Spec. act. |
|---|---|---|---|---|
| GAV213 | Monascus kaoliang | 1.66 | 145 | 87 |

Figure 4:
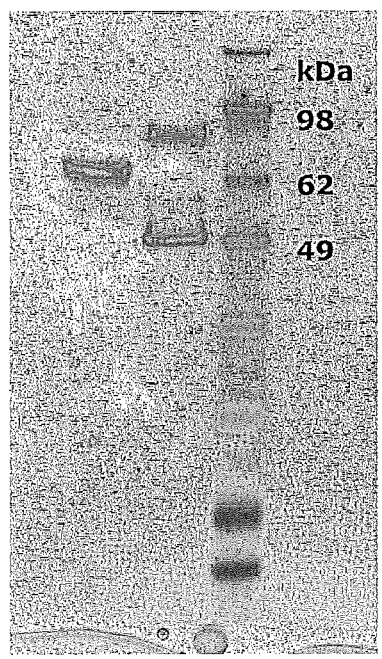
FIG. 4 depicts a SDS-PAGE analysis of the fermentation broth of *Monascus kaoliang* (left sample) as compared to that of *Aspergillus niger* (right sample). The fermentation broth of *Aspergillus niger* (right sample) contains a secreted alpha amylase, whereas the fermentation broth of *Monascus kaoliang* (left sample) shows only the glucoamylase.

The fermentation broth of *Monascus kaoliang* was compared to that of *Aspergillus niger* by SDS-PAGE analysis. As can be seen in FIG. 4, the production of glucoamylase of wild type *Monascus kaoliang* is remarkably high, and the yield of the fermentation is in the same order as *Aspergillus niger* strain dgr246.

Surprisingly, as depicted in FIG. 4, the fermentation broth of *Aspergillus niger* contains a secreted alpha amylase, whereas the fermentation broth of *Monascus kaoliang* shows only the glucoamylase. Thus, it appears that glucoamylase is the only dominant enzyme secreted by *Monascus kaoliang*.

Example 2

Elucidation of the *Monascus kaoliang* Glucoamylase Genes

To further characterize glucoamylase from *Monascus kaoliang*, *Monascus kaoliang* strain (CBS302.78) culture pre-grown overnight in MD-medium with 2% maltose was induced for 8 hours in fresh MD-medium with 15% maltose to initiate glucoamylase synthesis. Total RNA was isolated from *M. kaoliang* using the Qiagen RNeasy® plant Mini kit (Cat#74904). The Invitrogen RNase AWAY (Cat#10328-011) was used to clear all materials and work surfaces of RNase.

Total RNA was used in construction of a cDNA library using a Cloneminer™ Library Construction Kit (Invitrogen, cat#18249-029). Approximately 2920 colonies from the library were plated on 2TY-medium [Bacto Tryptone (16 g/L), Bacto Yeast Extract (10 g/L), NaCL (5 g/L), Agar (15 g/L)] supplemented with kanamycin (50 µg/ml). Colonies were transferred onto a Hybond-N membrane (Cat# RPN2222N). Membranes were screened for the glucoamylase cDNA inserts by Southern hybridization using the labeling and detection system of Roche Applied Science, Indianapolis, Ind. 46250-0414 USA. A homologous probe that was used was isolated in a 2 step process. First an internal fragment of the *Monascus kaoliang* GA gene was isolated by PCR from the cDNA library template using degenerated primers designed from amino acid fragments resulted from the MS/LC: Deg.FW: 5'-GAYTAYTTYTAY-ACNTGG-3' (SEQ ID NO:7) and Deg.RV: 5'-YTGRTANA-CRTCDTCNGG-3' (SEQ ID NO:8). In the next step a homologous probe was isolated by PCR using the homologous primers derived from the fragments mentioned above: MkGA probe FW: 5'-CTGGTCAATGGTGACGTGAATC-3' (SEQ ID NO:9) and MkGA probe RV: 5'-GCAATAC-CCGAGTTGAGAGAGTAG-3' (SEQ ID NO:10). Twenty-three (23) out of the 2920 of these colonies gave a positive hybridization signal and were confirmed to contain glucoamylase cDNA fragments by sequence analysis. Results of the sequence analysis of these glucoamylase cDNA fragments demonstrated that there were two different variants of glucoamylase. A first, longer variant, referred to herein as glucoamylase II, codes for glucoamylase with a Starch Binding Domain (SBD), and a second, shorter variant, referred to herein as glucoamylase I, codes for a glucoamylase without a SBD (SEQ ID NO 2 and SEQ ID NO 5, respectively). The difference between the two variants is a gap of 162 base pairs at the end of the linker region that separates the catalytic core and the SBD (SEQ ID NO 3 and SEQ ID NO 6). This gap in the sequence results in a shift of the reading frame of +1 to +3, and as a consequence, a preliminary termination of translation appears to account for the two glucoamylase forms. Additionally, it was discovered that an extra mutation in glucoamylase II cDNA results in an amino acid substitution of Alanine for Proline at position 507 (A507P).

To gain more information about the intron positions and the origin of the 2 cDNA species, a PCR was performed on genomic DNA using specific primers starting from the first start codon to the stop codon of the SBD: MkGA FW: 5'-ATGATTGACACAAAACCGACTGATATCGTCTC-3'

(SEQ ID NO:11) and MkGA RV: 5'-CTACTTCCAGCT-GTCGTTGACGGTCAC-3' (SEQ ID NO:12). The reaction was performed on a MJ Research PTC-200 Peltier thermal cycler using Platinum® Taq DNA Polymerase High Fidelity from Invitrogen (Cat#11304-011) according protocols of the supplier. All PCR product were purified using the Qiagen QIAquick® PCR purification kit (Cat#28106) according to manufactures protocol. The PCR showed two bands on a gel, the bands being approximately 2.1 kb and 2.3 kb in length (not shown). Sequence analysis showed that both genomic fragments code for the glucoamylase I and II forms (SEQ ID NO 4 and SEQ ID NO 1, respectively). Within the exon sequences, these fragments showed 100% identity to the corresponding cDNA clones described above. Sequence alignment allowed for the identification of 4 introns within the longer glucoamylase II gene. The shorter glucoamylase I gene lacks exactly the same 162 base pair stretch at the end of the linker, and bears the mutation at the position 507 as the shorter cDNA clone. Based on these results it can be concluded that the *Monascus kaoliang* genome contains two closely related glucoamylase genes coding for a protein with and without the SBD. It was also found that both genes within the overlapping region are virtually identical, save for a single nucleotide change.

Example 3

Use of *Monascus kaoliang* Glucoamylase from Fermentation Broth in Conventional Ethanol Fermentation The use of *M. kaoliang* glucoamylase to saccharify liquefied starch and support ethanol fermentation was compared to a glucoamylase from *Aspergillus niger*.

An ethanol fermentation assay was preformed as follows: Frozen liquefact (liquefied starch having 32% dry solids (DS) content) was thawed at 75° C., and then brought to room temperature, with a measured pH of 5.6. Ethanol yeast was provided by the Red Star Yeast Company. Liquefact was then dispensed in 150 gram quantities into 250 ml Erlenmeyer flasks. 500 µl of a 20% yeast/water solution and 600 µl of 10% urea/water solution (400 ppm) was added to each flask. Enzymes were dosed according to the experimental design in Table 3. As the activity of the MkGA was relatively low, a large volume was required to achieve the desired dose. Water was added to the flasks to keep the volumes constant. The flasks were incubated at 32° C. in a forced air shaker at 150 rpm.

TABLE 3

| Flask | Description | µL GA | µL water | µL total | glucoamylase units (GAU) |
|---|---|---|---|---|---|
| 1 and 2 | AnGA | 32.0 | 2101.0 | 2133.0 | 15.6 |
| 3 and 4 | MkGA @ 0.325 | 1733.0 | 400.0 | 2131.0 | 15.6 |
| 5 and 6 | MkGA @ 0.40 | 2133.0 | 0 | 2131.0 | 19.2 |

AnGA: *Aspergillus niger* glucoamylase (487 glucoamylase units/g)
MkGA: *Monascus kaoliang* glucoamylase I and II preparation (9 glucoamylase units/g)

Samples were taken from each flask at scheduled intervals for HPLC analysis and at the end of fermentation for starch analysis.

For HPLC analysis, samples were first centrifuged, diluted 1:10 in 0.1 N $H_2SO_4$, heated to 75° C. for 15 minutes and filtered through a 0.45 micron filter. A 10 microliter sample was injected into an HPLC Phenomenex Rezex Organic Acid column coupled to a Refractive Index Detector, where the 23 minute HPLC run conditions were: 65° C. with 0.01 N $H_2SO_4$ as the mobile phase.

For Insoluble Residual Starch (IRS) analysis, a 100 g aliquot of fermentation broth was placed in a 250 ml Erlenmeyer and while stirring with a stir bar, the sample was heated to boiling point, and boiled for 10 minutes, and then centrifuged (HOT). The supernatant was decanted, allowed to cool on ice for 10 minutes, and then warmed to room temperature. A 1.0 ml sample of the supernatant was then added to 14 ml of Distilled $H_2O$ in a 15 ml volumetric test tube, and the insoluble starch residue was allowed to settle overnight. The volume of sedimented starch was assessed visually.

TABLE 4

Average HPLC Data

| Flask | Description | hrs | % W/V DP > 3 | % W/V DP-3 | % W/V DP-2 | % W/V DP-1 | % W/V Lactic | % W/V Glycerol | % W/V Acetic | % V/V Ethanol |
|---|---|---|---|---|---|---|---|---|---|---|
| 1, 2 | AnGA | 17 | 7.68 | 0.10 | 4.08 | 2.98 | 0.12 | 1.22 | 0.04 | 7.91 |
|  |  | 24 | 6.19 | 0.15 | 1.48 | 2.89 | 0.12 | 1.35 | 0.05 | 10.21 |
|  |  | 40 | 1.21 | 0.16 | 0.26 | 2.07 | 0.08 | 1.45 | 0.08 | 13.70 |
|  |  | 48 | 0.78 | 0.13 | 0.35 | 1.05 | 0.06 | 1.48 | 0.09 | 14.41 |
| 3, 4 | MGA @ 0.325 | 17 | 8.55 | 0.09 | 4.21 | 0.46 | 0.15 | 1.20 | 0.04 | 8.88 |
|  |  | 24 | 7.50 | 0.11 | 1.77 | 0.19 | 0.14 | 1.26 | 0.05 | 10.85 |
|  |  | 40 | 3.51 | 0.17 | 0.12 | 0.05 | 0.09 | 1.30 | 0.08 | 14.00 |
|  |  | 48 | 2.74 | 0.16 | 0.11 | 0.03 | 0.07 | 1.31 | 0.09 | 14.29 |
| 5, 6 | MGA @ 0.40 | 17 | 8.18 | 0.08 | 3.16 | 1.09 | 0.13 | 1.23 | 0.05 | 9.48 |
|  |  | 24 | 6.68 | 0.15 | 0.58 | 0.25 | 0.12 | 1.29 | 0.07 | 11.99 |
|  |  | 40 | 2.48 | 0.15 | 0.12 | 0.04 | 0.06 | 1.32 | 0.09 | 14.46 |
|  |  | 48 | 2.07 | 0.14 | 0.11 | 0.03 | 0.05 | 1.31 | 0.09 | 14.36 |

Figure 5:
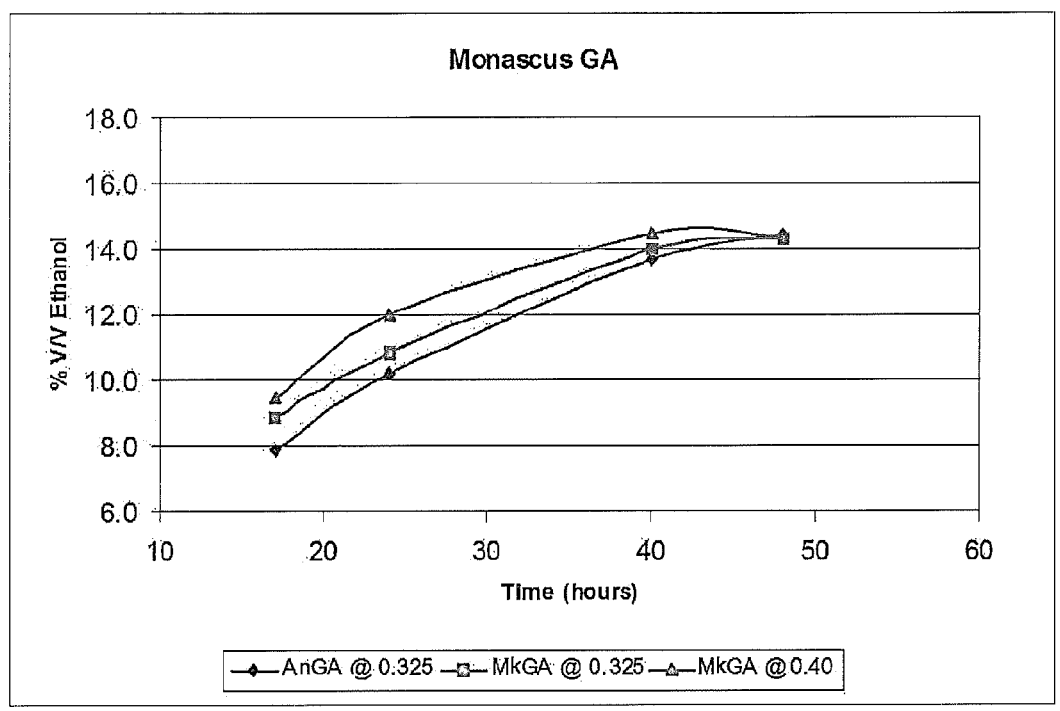
FIG. 5 depicts the rate and yield of ethanol production in the presence of glucoamylase from *Monascus kaoliang* (MkGA) compared to glucoamylase from *Aspergillus niger* (AnGA). The rate of ethanol production is faster with MkGA than with AnGA when dosed equally at 0.325 glucoamylase units/g dry solids (DS) of liquefied starch. When dosed at 0.4 glucoamylase units/g DS, the rate of ethanol production with MkGA was even faster. The final alcohol yield was comparable regardless of dose or enzyme.

As seen in Table 1 and FIG. 5, a faster rate of ethanol fermentation was obtained using *M. kaoliang* glucoamylase (MkGA) than *A. niger* glucoamylase, when compared on the basis of an equal number of units of glucoamylase (GAU)/g dry solids (DS) of liquefied starch dose, indicating a better carbon conversion efficiency. Final yields of alcohol produced using the two glucoamylases were comparable, at approximately 14.3%.

Figure 6:
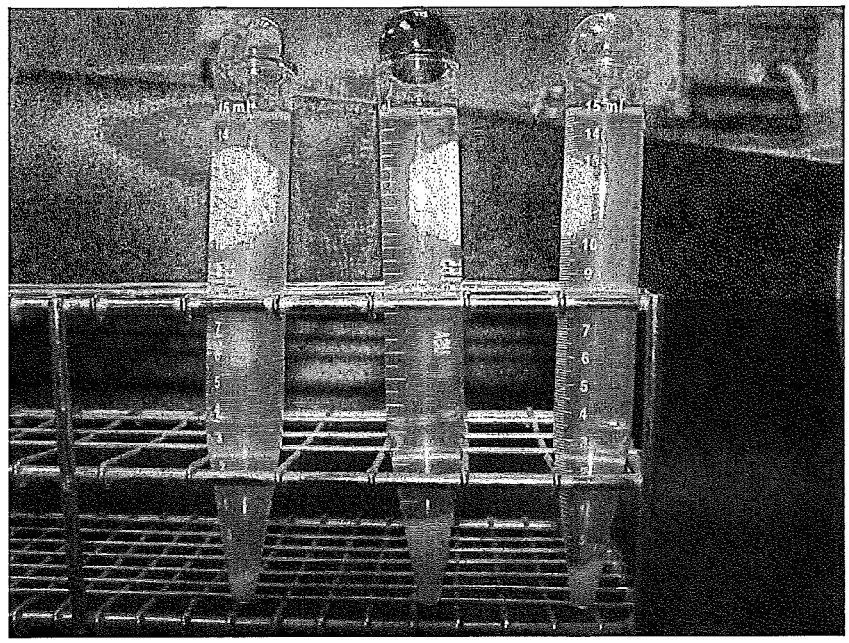
FIG. 6 depicts the amount of insoluble residual starch remaining after yeast fermentation of liquefied starch in the presence of glucoamylase from *Aspergillus niger* (AnGA) or *Monascus kaoliang* (MkGA). Dosing of glycoamylase: 325 units of AnGA per gram dry solids of liquefied starch in the left-hand tube; 325 units and 400 units MkGA per gram dry solids of liquefied starch in the central and right-hand tube, respectively.

The amount of insoluble residual starch (IRS) remaining after ethanol fermentation of the liquefied starch in the presence of glucoamylase was greater for *M. kaoliang* glucoamylase (MkGA) than *A. niger* glucoamylase when compared on the basis of 0.325 GAU/g DS. However, a 25% increase in the MkGA dose (0.4 GAU/g DS) left similar levels of IRS as 0.325 GAU/g DS of AnGA (FIG. 6).

Example 4

Use of *Monascus kaoliang* Glucoamylase from Fermentation Broth in the Fermentation Step of Brewing The use of *M. kaoliang* glucoamylase to saccharify wort carbohydrates and support ethanol fermentation was compared to DIAZYME® X4 which comprises a glucoamylase from *Aspergillus niger* (AnGA). Fermentation trials were performed using hopped wort prepared from Munton's Bitter Home Brew Kit having an initial Specific Gravity of 1056.7 (i.e. 13.92° Plato). 200 ml of the wort were added to each 500 ml flask (Fermenting Vessel; FV), which was then autoclaved at 99° C. for 10 minutes and then cooled. The following additions were made to the flasks:

Negative control flasks received 1 ml sterile water;

Positive control flasks received 1 ml of a 100 fold dilution of DIAZYME® X4 (concentrated glucoamylase derived from a strain of *Aspergillus niger*) supplied by Genencor International, equivalent to an addition rate of 5 g DIAZYME® X4 per hl pitching wort;

Test flasks received 1 ml of a 2.9 g→5 ml dilution of the *Monascus kaoliang* glucoamylase, equivalent to the same addition rate, in terms of units of glucoamylase activity added per hl pitching wort, as that used for DIAZYME® X4 in the Positive control.

Each flask was dosed with W34/70 (Weihenstephan) yeast at a dose rate of 10.106 per ml per ° Plato, the fermentation was allowed to proceed under standardised laboratory test conditions (an elevated temperature of 22.5° C., with gentle agitation of 100 rpm, in an orbital incubator for up to 165 hours). Each flask was analysed at scheduled intervals with respect to weight loss and specific gravity, while Real Degree of Fermentation (RDF, which is the Real Attenuation expressed in percentage form) was calculated for the final fermented wort (beer) and a sample was subjected to HPLC analysis of the carbohydrate composition and the products of fermentation, employing methods set out in Example 3. Specific gravity of the wort before, during and after fermentation was measured using a specific gravity hydrometer or Anton-Paar density meter (e.g. DMA 4100 M) and Real Attenuation was calculated and expressed in percentage form as RDF according to the formulae listed by Ensminger (see http://hbd.org/ensmingr/ "Beer data: Alcohol, Calorie, and Attenuation Levels of Beer"). Monitoring weight loss during fermentation provides an indirect measure of $CO_2$ evolution and hence ethanol formation.

TABLE 5

Fermentation trial: Addition of MkGA or DIAZYME ® X4 to the FV

| Enzyme(s) added | Dose rate (g/hl) | | Initial S.G. | Solids (% Plato) | RDF (%) | Final S.G. | Real Extract (%) | Final glycerol (% w/v) | Final ethanol (% v/v) |
|---|---|---|---|---|---|---|---|---|---|
| Control | | | 1.057 | 13.923 | 63.280 | 1.012 | 5.112 | 0.243 | 5.452 |
| (no enzyme) | | | 1.057 | 13.923 | 63.132 | 1.013 | 5.133 | 0.247 | 5.326 |
| | | | 1.057 | 13.923 | 63.429 | 1.012 | 5.092 | 0.239 | 5.349 |
| | | | 1.057 | 13.923 | 63.280 | 1.012 | 5.112 | 0.242 | 5.380 |
| | | mean | 1.057 | 13.923 | 63.280 | 1.012 | 5.112 | 0.243 | 5.377 |
| | | stdev | 0.000 | 0.000 | 0.122 | 0.000 | 0.017 | 0.003 | 0.055 |
| | | UL | 1.057 | 13.923 | 63.474 | 1.013 | 5.139 | 0.248 | 5.464 |
| | | LL | 1.057 | 13.923 | 63.087 | 1.012 | 5.085 | 0.237 | 5.290 |
| DIAZYME ® X4 | 5 | | 1.057 | 13.923 | 79.948 | 1.001 | 2.792 | 0.256 | 6.612 |
| (Lot # | | | 1.057 | 13.923 | 80.403 | 1.001 | 2.728 | 0.267 | 6.742 |
| 1681046910) | | | 1.057 | 13.923 | 79.797 | 1.001 | 2.813 | 0.283 | 6.783 |
| 409.9 GAU/g | | | 1.057 | 13.923 | 79.645 | 1.002 | 2.834 | 0.272 | 6.806 |
| | | mean | 1.057 | 13.923 | 79.948 | 1.001 | 2.792 | 0.270 | 6.736 |
| | | stdev | 0.000 | 0.000 | 0.327 | 0.000 | 0.046 | 0.011 | 0.087 |
| | | UL | 1.057 | 13.923 | 80.469 | 1.002 | 2.864 | 0.287 | 6.874 |
| | | LL | 1.057 | 13.923 | 79.428 | 1.001 | 2.719 | 0.252 | 6.598 |
| MkGA | 5 | | 1.057 | 13.923 | 77.376 | 1.003 | 3.150 | 0.278 | 6.250 |
| 409.9 GAU | | | 1.057 | 13.923 | 77.679 | 1.003 | 3.108 | 0.260 | 6.207 |
| equiv. | | | 1.057 | 13.923 | 77.830 | 1.003 | 3.087 | 0.271 | 6.616 |
| | | | 1.057 | 13.923 | 78.435 | 1.002 | 3.002 | 0.258 | 6.673 |
| | | mean | 1.057 | 13.923 | 77.830 | 1.003 | 3.087 | 0.267 | 6.437 |
| | | stdev | 0.000 | 0.000 | 0.445 | 0.000 | 0.062 | 0.009 | 0.242 |
| | | UL | 1.057 | 13.923 | 78.538 | 1.003 | 3.185 | 0.282 | 6.821 |
| | | LL | 1.057 | 13.923 | 77.122 | 1.002 | 2.988 | 0.251 | 6.052 |

Figure 7:
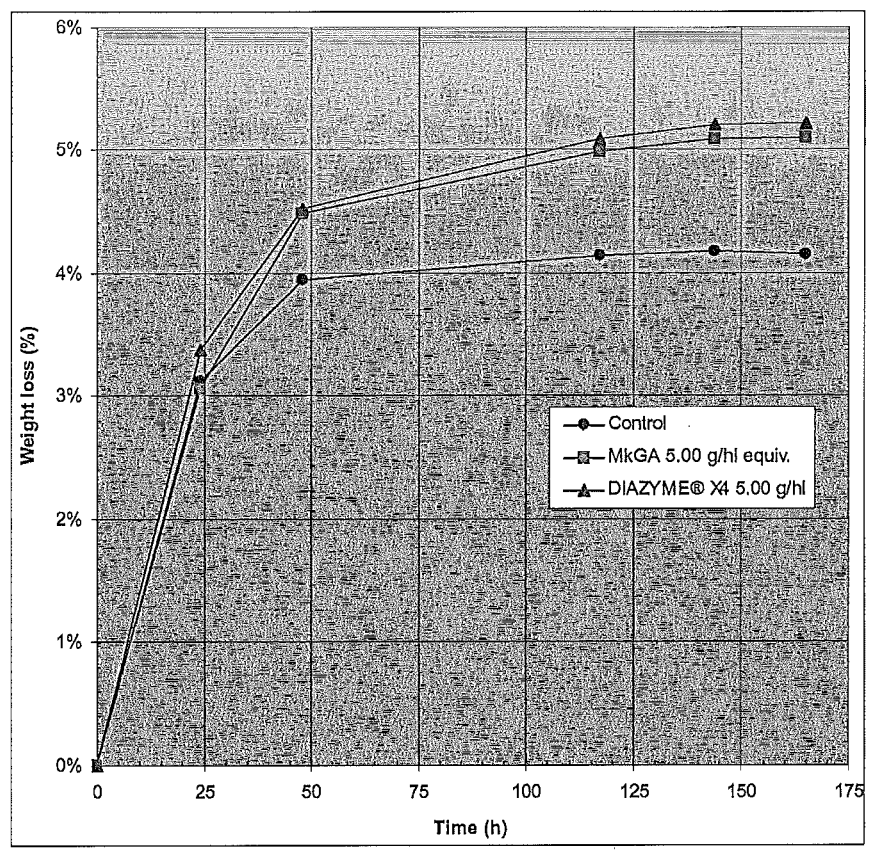
FIG. 7 depicts the weight loss during yeast fermentation of a wort in the presence or absence of DIAZYME® X4 or an equal number of units of *Monascus kaoliang* glucoamylase (MkGA) over a period of 175 h. The control is without enzyme.

Analysis of the final beer, produced by fermentation in the presence of an equivalent number of units of glucoamylase from MkGA compared with DIAZYME® X4, revealed that MkGA glucoamylase gave a slightly lower yield with respect to ethanol production, weight loss ($CO_2$ production) and RDF (see Tables 5-7 and FIG. 7). Correspondingly the content of oligosaccharides having a polymerization of DP4 and above was elevated in the final beer produced with MkGA glucoamylase. These results clearly show that DIAZYME® X4 can be substituted with MkGA glucoamylase to generate fermentable carbohydrates in the wort to support ethanol fermentation. An increased dosage of MkGA glucoamylase in the fermenting vessel is likely to support rates of ethanol production similar to or greater than that of DIAZYME® X4, based on the enhanced ethanol production seen with higher MkGA dosage rates shown in Example 3.

TABLE 6

HPLC carbohydrate analyses of the fermented worts

| Enzyme(s) added | Dose rate (g/hl) | DP1 Fructose (% w/v) | DP1 Glucose (% w/v) | DP2 (% w/v) | DP3 (% w/v) | DP4+ (% w/v) | Total (% w/v) |
|---|---|---|---|---|---|---|---|
| Control | | 0.055 | 0.044 | 0.191 | 0.360 | 2.783 | 3.432 |
| (no enzyme) | | 0.066 | 0.042 | 0.189 | 0.366 | 2.830 | 3.493 |
| | | 0.070 | 0.045 | 0.169 | 0.360 | 2.750 | 3.394 |
| | | 0.065 | 0.041 | 0.173 | 0.347 | 2.761 | 3.387 |

TABLE 6-continued

HPLC carbohydrate analyses of the fermented worts

| Enzyme(s) added | Dose rate (g/hl) | | DP1 Fructose (% w/v) | DP1 Glucose (% w/v) | DP2 (% w/v) | DP3 (% w/v) | DP4+ (% w/v) | Total (% w/v) |
|---|---|---|---|---|---|---|---|---|
| | | Mean | 0.064 | 0.043 | 0.180 | 0.358 | 2.781 | 3.426 |
| | | Stdev | 0.006 | 0.002 | 0.011 | 0.008 | 0.035 | 0.049 |
| | | UL | 0.074 | 0.046 | 0.198 | 0.371 | 2.837 | 3.504 |
| | | LL | 0.054 | 0.040 | 0.162 | 0.346 | 2.725 | 3.349 |
| DIAZYME ® X4 (Lot # 1681046910) 409.9 GAU/g | 5 | | 0.048 | 0.033 | 0.200 | 0.289 | 0.637 | 1.208 |
| | | | 0.047 | 0.032 | 0.183 | 0.284 | 0.633 | 1.179 |
| | | | 0.049 | 0.031 | 0.186 | 0.291 | 0.655 | 1.212 |
| | | | 0.050 | 0.031 | 0.202 | 0.302 | 0.652 | 1.237 |
| | | Mean | 0.048 | 0.032 | 0.193 | 0.291 | 0.644 | 1.209 |
| | | Stdev | 0.001 | 0.001 | 0.010 | 0.008 | 0.011 | 0.024 |
| | | UL | 0.050 | 0.034 | 0.208 | 0.304 | 0.662 | 1.246 |
| | | LL | 0.047 | 0.030 | 0.177 | 0.279 | 0.627 | 1.171 |
| MkGA 409.9 GAU equiv. | 5 | | 0.058 | 0.037 | 0.220 | 0.318 | 0.835 | 1.467 |
| | | | 0.058 | 0.037 | 0.224 | 0.323 | 0.830 | 1.472 |
| | | | 0.059 | 0.037 | 0.217 | 0.338 | 0.885 | 1.535 |
| | | | 0.057 | 0.035 | 0.159 | 0.287 | 0.808 | 1.346 |
| | | Mean | 0.058 | 0.036 | 0.205 | 0.316 | 0.840 | 1.455 |
| | | Stdev | 0.001 | 0.001 | 0.031 | 0.021 | 0.032 | 0.079 |
| | | UL | 0.059 | 0.038 | 0.254 | 0.350 | 0.891 | 1.581 |
| | | LL | 0.056 | 0.034 | 0.156 | 0.282 | 0.788 | 1.329 |

TABLE 7A

Weight loss data

| | | Flask weight (g) | | | | | | |
|---|---|---|---|---|---|---|---|---|
| Flask | Enzyme | Empty | Start | 24 h | 48 h | 117 h | 144 h | 165 h |
| 1 | Control | 178.06 | 389.1 | 383.7 | 380.9 | 380.4 | 380.3 | 380.37 |
| 2 | (no enzyme) | 171.82 | 383.1 | 376.7 | 374.8 | 374.4 | 374.3 | 374.38 |
| 3 | | 171.88 | 385.2 | 377 | 376.6 | 376.2 | 376.2 | 376.27 |
| 4 | | 172.92 | 384.5 | 378 | 376.2 | 375.8 | 375.7 | 375.74 |
| 5 | DIAZYME ® X4 | 171.3 | 383.4 | 376.2 | 373.8 | 372.6 | 372.3 | 372.32 |
| 6 | (Lot # | 179.29 | 391.4 | 383.3 | 381.6 | 380.4 | 380.2 | 380.22 |
| 7 | 1681046910) | 160.74 | 372.4 | 365.4 | 362.9 | 361.7 | 361.5 | 361.45 |
| 8 | 409.9 GAU/g | 178.86 | 390.2 | 383.9 | 380.8 | 379.6 | 379.3 | 379.26 |
| 9 | MkGA | 162.03 | 374 | 368.5 | 364.6 | 363.5 | 363.3 | 363.26 |
| 10 | 409.9 GAU | 173.02 | 384.5 | 378.5 | 375.1 | 374 | 373.8 | 373.76 |
| 11 | equiv. | 177.48 | 388.8 | 382.5 | 379.4 | 378.3 | 378.1 | 378.05 |
| 12 | | 175.28 | 387.7 | 379.5 | 377.9 | 377 | 376.7 | 376.74 |

TABLE 7B

Weight loss data (% of the start weight)

| Enzyme(s) added | Dose rate (g/hl) | | Weight loss (%) at: | | | | | |
|---|---|---|---|---|---|---|---|---|
| | | | 0 | 24 | 48 | 117 | 144 | 165 |
| Control (no enzyme) | | | 0.00% | 2.56% | 3.89% | 4.12% | 4.17% | 4.14% |
| | | | 0.00% | 3.03% | 3.93% | 4.12% | 4.17% | 4.13% |
| | | | 0.00% | 3.84% | 4.03% | 4.22% | 4.22% | 4.19% |
| | | | 0.00% | 3.07% | 3.92% | 4.11% | 4.16% | 4.14% |
| | | Mean | 0.00% | 3.13% | 3.94% | 4.14% | 4.18% | 4.15% |
| | | Stdev | 0.00000 | 0.00532 | 0.00063 | 0.00051 | 0.00028 | 0.00026 |
| | | UL | 0.00% | 3.97% | 4.04% | 4.22% | 4.22% | 4.19% |
| | | LL | 0.00% | 2.28% | 3.84% | 4.06% | 4.13% | 4.11% |
| DIAZYME ® X4 (Lot # 1681046910) 409.9 GAU/g | 5 | | 0.00% | 3.39% | 4.53% | 5.09% | 5.23% | 5.22% |
| | | | 0.00% | 3.82% | 4.62% | 5.19% | 5.28% | 5.27% |
| | | | 0.00% | 3.31% | 4.49% | 5.06% | 5.15% | 5.17% |
| | | | 0.00% | 2.98% | 4.45% | 5.02% | 5.16% | 5.18% |
| | | Mean | 0.00% | 3.38% | 4.52% | 5.09% | 5.21% | 5.21% |
| | | Stdev | 0.00000 | 0.00345 | 0.00074 | 0.00073 | 0.00063 | 0.00046 |
| | | UL | 0.00% | 3.92% | 4.64% | 5.20% | 5.30% | 5.28% |
| | | LL | 0.00% | 2.83% | 4.40% | 4.97% | 5.11% | 5.14% |
| MkGA 409.9 GAU equiv. | 5 | | 0.00% | 2.59% | 4.43% | 4.95% | 5.05% | 5.07% |
| | | | 0.00% | 2.84% | 4.44% | 4.97% | 5.06% | 5.08% |
| | | | 0.00% | 2.98% | 4.45% | 4.97% | 5.06% | 5.09% |
| | | | 0.00% | 3.86% | 4.61% | 5.04% | 5.18% | 5.16% |
| | | Mean | 0.00% | 3.07% | 4.49% | 4.98% | 5.09% | 5.10% |
| | | Stdev | 0.00000 | 0.00552 | 0.00086 | 0.00038 | 0.00061 | 0.00042 |
| | | UL | 0.00% | 3.95% | 4.62% | 5.04% | 5.18% | 5.16% |
| | | LL | 0.00% | 2.19% | 4.35% | 4.92% | 4.99% | 5.03% |

Example 5

Purification of MkGA I and MkGA II and their Use in the Fermentation Step of Brewing Purification

*Monascus kaoliang* CBS302.78 was grown on PDA agar plates. To initiate the pre-culture fermentation use a piece (~1 cm$^2$) of a fresh PDA plate with *M. kaoliang* CBS302.78 to inoculate 50 ml LD-maltose medium in a 250 ml sterile baffled shake flask. The culture was grown for 2 days at 28° C. and harvested. 50 mL of this culture was transferred to 1000 ml LD-maltose medium in a 2.8 L baffled Fernbac and incubated 4 days at 28° C. with pH fixed at 5.0 or 5.5. The cell culture is harvested and media clarified by centrifugation (4000 rpm at 15 min.) and filtration (VacuCap 90, 0.2 µm). Following, the ferment was concentrated and stored at −20° C.

MkGA I and MkGA II were purified as follows: Clarified fermentation broth was treated with active charcoal to remove the excess of *Monascus kaoliang* secreted pigments such as: Monascin, ankaflavin and monascorubrin. Thus, ferment broth was added 2% (w/v) Norit SA Plus and left with stirring at RT for 20 min. This slurry was centrifuged at 4000 rpm for 20 min. and filtered (0.2 µm) before diluting it 1:4 with Buffer A (25 mM Na-Acetat pH 4.3) used for the first column. Chromatography was carried out manually on a BioRAD FPLC system. A 15 ml β-cyclodextrin column was made by immobilizing β-cyclodextrin (Sigma-Aldrich; CAS nr:68168-23-0) on Epoxy-activated Sepharose™ 6B (GE Healthcare; Lot: 10021987). This (β-CD-column was equilibrated with Buffer A at a flow rate of 2 ml/min. This flow rate was maintained throughout the purification. The sample containing 500 M-GAU was loaded onto the column through the inlet tubing and fractions of 10 ml were collected throughout purification. MkGA I could be collected in the flowthrough and the buffer was switched to 100% Buffer B (10 mM α-cyclodextrin in 25 mM Na-acetat pH 4.3) after stabilisation of the baseline by extensive washing with Buffer A. Bound MkGA II was eluted from the column and the buffer was finally switched back to A after all protein was eluted. Protein in the flowthrough and elution was analyzed for glucoamylase activity and by SDS-page.

All SDS-page gels were run with the Invitrogen NuPage® Novex 10% Bis-Tris gel 1.0 mm, 10 well (Cat#NP0321box), See-Blue® Plus2 prestained Standard (Cat# LC5925) and NuPAGE® MES SDS Running Buffer (Cat# NP0002) according to the manufacturer's protocol. Stained with Coomasie Brilliant-Blue.

MkGA I- and MkGA II-containing fractions were pooled separately and α-cyclodextrin was removed by passing the sample through a PD10 columns. GA containing fractions were concentrated in Vivaspin™ ultrafiltration centrifuge tubes to approximately 20 mg/ml (25 ml, 10K MWCO, Sartorius).

The flowthrough from β-cyclodextrin column with MkGA I contained small amounts of MkGA II (<10%) and was purified further. The sample of MkGA I was changed to Buffer C (20 mM Citrate buffer pH3.5) by extensive dialysis. 4 ml sample (corresponding to 100 GAU) was loaded onto a 1 ml SPFF HiTrap column equipped on an Akta Pharmacia FPLC system (GE Healthcare) pre-equilibrated with Buffer C and running with a flow of 1 ml/min. The bound proteins were separated with a 20 CV gradient into 50% Buffer D (20 mM Citrate buffer pH3.5, 1 M NaCl). Peak fractions were collected and analyzed for glucoamylase activity and by SDS-page. Completely pure MkGA I and MkGA II were obtained in this way.

The amino acid sequence of the purified MkGA I and MkGA II was obtained by MS analysis (SEQ ID NO. 6 and SEQ ID NO. 3) and agreed with the translated cDNA sequences.

Glucoamylase activity was assayed by a Megazyme R-AMGR3 assay (M-GAU) according to manufactures description (see example 6). Dilution and mixing were performed in 96 well ELISA plates on a Biomek 3000 (Beckman Coulter).

Brew Analysis:

MkGA I, MkGA II, AnGA (DIAZYME® X4) and TrGA were all tested in brewing experiments. In this setup a wort was made using Munton's malt extract. 340 g Munton's malt extract was dissolved in 1500 ml hot water. This slurry was added 5 pellets of hops, pH adjusted to 5.2 by $H_2SO_4$ and boiled for 1 hour before being autoclaved at 121° C. for 15 minutes. Afterwards, 0.6 g freshly produced W34/70 (Weihenstephan) yeast was added 100 g cooled wort together with the different enzymes. The enzymes were dosed on similar amount of protein (0.066 mg GA/mL wort) or similar β-D-maltoside activity (0.16 M-GAU/mL wort).

The worts were fermented at 18° C. and gentle agitation of 150 rpm, in 500 ml conical flasks. Residual activity was measured before and after fermentation. Production of ethanol was indirectly measured by weight loss of ferments. Alcohol was measured on an Anton-Paar density meter (e.g. DMA 4100 M) and Real Attenuation was calculated and expressed in percentage form as RDF according to the formulae listed by Ensminger (see http://hbd.org/ensmingr/ "Beer data: Alcohol, Calorie, and Attenuation Levels of Beer").

Carbohydrate Analysis of Fermented Wort:

Samples withdrawn from fermentation were analysed on a Gilson HPLC system with Gilson 234 autosampler. HPLC parameters were as follows: Mobile phase: Milli-Q water, Flow: Isochratic, 1 ml/min, Column: Phenomenex RSO—Oligosaccharide, Column temperature: 75° C., Injection volume: 20 µL, Detector: Refractive index (Laserchrom Schambeck RI detector), Integration: Manual, Sample preparation: 2 times dilution in Milli-Q water (2.5 ml sample+2.5 ml water) and filtration through 0.45 µm syringe filters, Quantification: Peak areas in percent of peak area of the standard. The following specimens were quantified: Ethanol, glycerol, glucose, DP2, DP3, DP4, DP4+(all above and including DP4) and DP1-4+.

As seen in table 8 the effect of MkGA I was superior to MkGA II in both dosage experiments and showed comparable within the experimental error to the effect obtained using either AnGA or TrGA.

TABLE 8

|  |  | Brew analysis - dosed on protein 0.066 mg GA/mL wort | | Brew analysis - dosed on activity 0.16 M-GAU/mL wort | |
|---|---|---|---|---|---|
|  |  | RDF (%) | Std | RDF (%) | Std |
| MkGA I | M. kaoliang | 77.81 | 0.130 | 77.73 | 0.255 |
| MkGA II | M. kaoliang | 77.03 | 0.141 | 77.28 | 0.156 |
| AnGA (DIAZYME ® X4) | A. niger | 77.42 | 0.203 | 78.19 | 0.184 |
| TrGA | T. reesei | 77.71 | 0.205 | 77.85 | 0.141 |

RDF values determined for listed GA's applied to the FV at the indicated doses, using a malt extract wort. Results are an average of 3 determinations.

Figure 8:
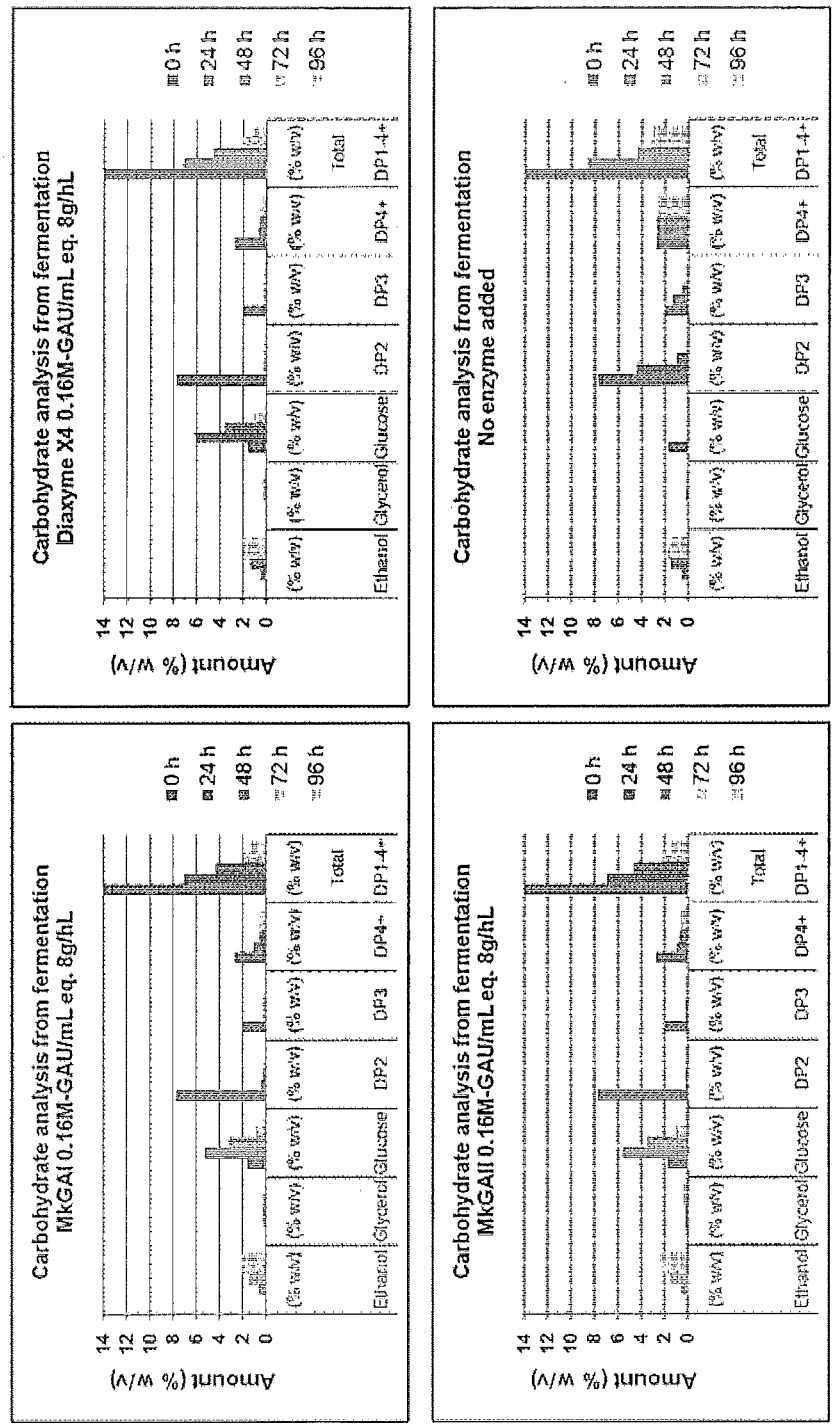
FIG. 8 depicts HPLC carbohydrate analysis of fermented worts with addition of: MkGA I, MkGA II, DIAZYME® X4 and no enzyme. The listed components were quantified (% w/v) by HPLC (Phenomenex RSO Oligosaccharide column, RI detector) from external standards of ethanol, glycerol and glucose at different time points during fermentation.

In accordance with the obtained RDF-values, MkGA I, MkGA II and DIAZYME® showed a very similar turnover of oligosaccharides in the wort during the fermentation period (96 h) (FIG. 8). The only notable difference is that DIAZYME® X4 shows slightly faster initial consumption of DP3 and DP4+ oligosaccharides compared to MkGA I and MkGA II. This however does not affect the end result of residual oligosaccharide composition and the obtained RDF values.

Example 6

Thermostability of MkGA I and MkGA II in Buffer and Beer

Glucoamylase activity of MkGA I, MkGA II, DIAZYME® X4 (AnGA) and TrGA was determined in beer pH(4.3-4.6) and in Na-Acetate pH(4.7) buffer using a lab-scale pasteurisation assay (ranging from 0 to 42 PU).

Determination of M-GAU Activity:

The assay is a ELISA scaled version of the Megazyme R-AMGR3 assay.

Substrate: p-Nitrophenyl-β-maltoside (4 mM), plus thermostable β-glucosidase (5 U/ml): Dissolve the contents of one vial in 10 mL of milli-q water, divide into aliquots of 1 mL and store frozen.

Buffer: 200 mM Sodium acetate buffer (pH 4.5). Add 5.9 mL of glacial acetic acid (1.05 g/mL) to 900 mL of milli-q water. Adjust the pH to pH 4.4 by addition of 1 M (4 g/100 mL) NaOH solution (approx. 30 mL is required). Adjust the volume to 1 L and store in a well sealed bottle at 4° C.

Dilute enzyme samples by a factor 10 in sodium acetate buffer (dilute further with the same buffer if necessary but remember that the first dilution is always needed in order to bring the pH to 4.5). In a 96 well plate: Mix 20 μL substrate with 20 μL enzyme solution and incubate at 40° C. with agitation for 10 minutes. Add 300 μL 2% Trizma base to terminate reaction and develop the color.

Measure absorbance at 400 nm against a reagent blank. Blanks are prepared by adding 300 μL of Trizma base solution (2%) to 20 μL of substrate with vigorous stirring, followed by the enzyme solution (20 μL). Activity is calculated as follows:

$$\text{Activity}(GAU/\text{ml}) = \frac{\Delta A_{400}}{10} \cdot \frac{340}{20} \cdot \frac{1}{18.1} \cdot \frac{1}{1,88} \cdot \text{Dilution}$$

Where: GAU=units of glucoamylase activity. One Unit is the amount of GA which release one μmole of p-nitrophenol from the substrate per minute at the defined pH and temperature. ΔA400=absorbance (reaction)—Absorbance (blank). 10=incubation time (min). 340=final reaction volume (μL). 20=volume of enzyme assayed (μL) 18.1=E mM p-nitrophenol in 2% trizma base (pH~8.5) at 400 nm (unit: μM-1*cm-1). 0.88=Light path (cm)

Pasteurisation Assay:

The relative loss of glucoamylase activity was determined in degassed beer or acetate buffer in a lab-scale pasteurisation assay. The sample was diluted 1:10 in beer or buffer and transferred to thin glass cuvette and placed in water bath at 72° C. where time and temperature were measured. Samples were withdrawn over time (0 to 100 sec) and hold on ice before determining the residual activity. Dilution and mixing were performed in 96 well ELISA plates on a Biomek 3000 (Beckman Coulter). To measure enzyme thermostability under the conditions used in the present experiments, the GAU activity was determined before and after incubation of enzymes. Beer or buffer without glucoamylase was used as blank. The accumulated energy input was converted into pasteurisation units PU, an energy equivalent index, by the equation stated above. Data is presented as relative activity lost.

Thermostability was determined in regular degassed Pilsner (Royal Export Pilsner) pH (4.5) for MkGA I, MkGA II, MkGA I+MkGA II, DIAZYME® X4 (AnGA) and TrGA. From the results in table 9, it is seen that MkGA I is significantly more thermolabile compared to the other tested glucoamylases in the Pilsner beer. MkGA I is completely inactivated with less than 26 pasteurisation units (PU) using a pasteurisation temperature of 72° C. In comparison MkGA II requires 100 PU and AnGA and TrGA need more than 200 PU to be inactivated. Notably, MkGA I is truncated and lacks the SBD compared to MkGA II, AnGA and TrGA that all have same domain structure with a catalytic domain and a SBD.

TABLE 9

Table 9. Residual glucoamylase activity after increasing pasteurisation at 72° C. in beer of MkGA I, MkGA II, MkGA I + MkGA II (MkGA), AnGA ((DIAZYME ® X4) and TrGA. Residual activity is calculated as the actual activity divided with the initial activity (0 PU) and results are an average of 3 determinations.

| | | Residual glucoamylase activity in beer after pasteurisation at 72° C. | | | | |
|---|---|---|---|---|---|---|
| Pasteurisation Units [PU] | Sample ID | MkGA I M. kaoliang (purified) | MkGA II M. kaoliang (purified) | MkGA I + MkGA II M. kaoliang (ferment) | AnGA (DIAZYME ®X4) A. niger (product) | TrGA T. reesei (ferment) |
| 0.000 | 1 | 1.000 | 1.000 | 1.000 | 1.000 | 1.000 |
| 0.020 | 2 | 0.840 | 0.895 | 0.910 | 0.974 | 0.956 |

TABLE 9-continued

Table 9. Residual glucoamylase activity after increasing pasteurisation at 72° C. in beer of MkGA I, MkGA II, MkGA I + MkGA II (MkGA), AnGA ((DIAZYME ® X4) and TrGA. Residual activity is calculated as the actual activity divided with the initial activity (0 PU) and results are an average of 3 determinations.

| Pasteurisation Units [PU] | Sample ID | MkGA I *M. kaoliang* (purified) | MkGA II *M. kaoliang* (purified) | MkGA I + MkGA II *M. kaoliang* (ferment) | AnGA (DIAZYME ®X4) *A. niger* (product) | TrGA *T. reesei* (ferment) |
|---|---|---|---|---|---|---|
| | | Residual glucoamylase activity in beer after pasteurisation at 72° C. | | | | |
| 0.180 | 3 | 0.122 | 0.700 | 0.375 | 0.857 | 0.945 |
| 2.190 | 4 | 0.036 | 0.547 | 0.144 | 0.774 | 0.898 |
| 6.770 | 5 | 0.021 | 0.230 | 0.074 | 0.561 | 0.612 |
| 13.16 | 6 | 0.004 | 0.110 | 0.020 | 0.474 | 0.471 |
| 26.81 | 7 | 0.000 | 0.031 | 0.002 | 0.349 | 0.271 |
| 48.69 | 8 | 0.000 | 0.015 | 0.002 | 0.225 | 0.202 |
| 75.20 | 9 | 0.000 | 0.002 | 0.000 | 0.164 | 0.153 |
| 102.2 | 10 | 0.000 | 0.000 | 0.000 | 0.125 | 0.114 |

Figure 9:
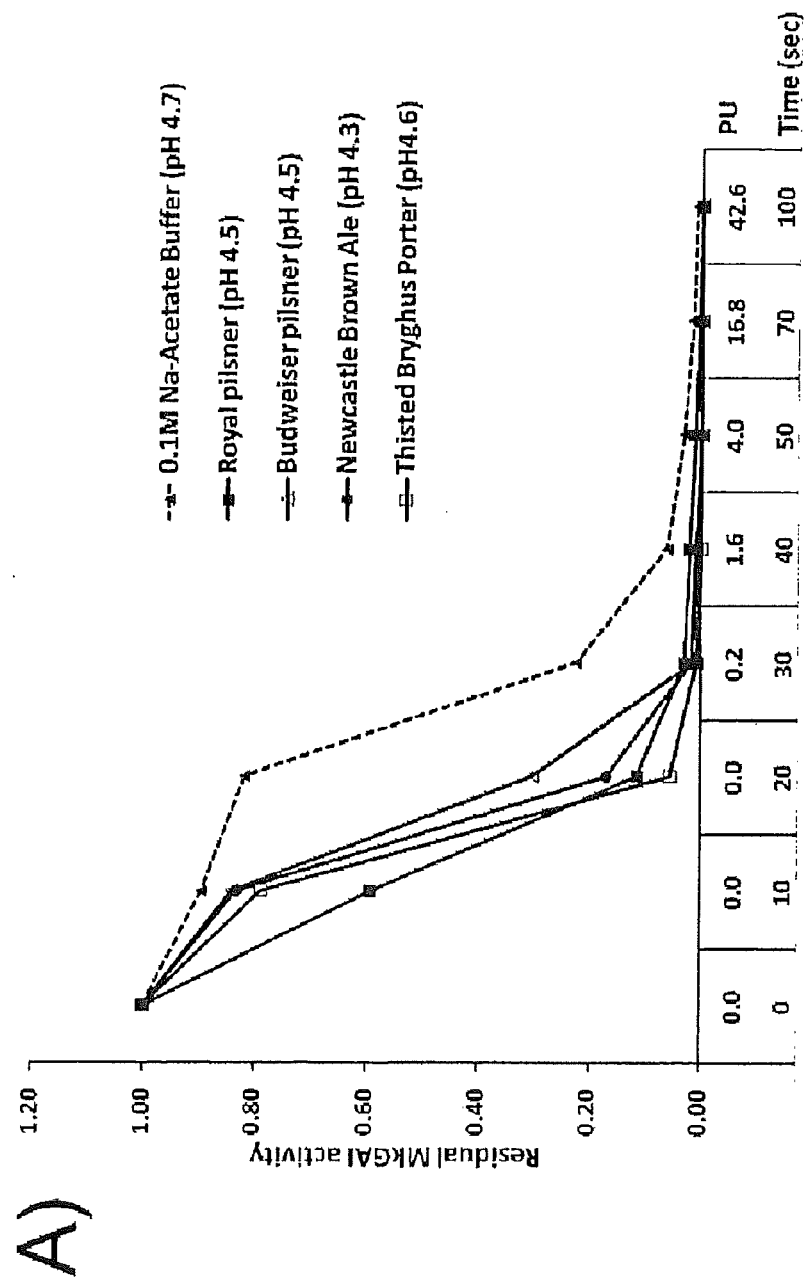
FIG. 9 depicts residual glucoamylase activity of A) MkGA I, B) MkGA II and C) DIAZYME® X4 (using a β-D-maltoside substrate) as function of pasteurisation time and pasteurisation units (PU) at 72° C. Residual glucoamylase activity was measured in Royal Pilsner (filled square), Budweiser Pilsner (triangle), Newcastle Brown ale (filled circle), Thisted bryghus Porter (square) beer and 0.1 M Na-Acetate pH (4.7) (dotted line). Results are shown as an average of 2 determinations.
Figure 9:
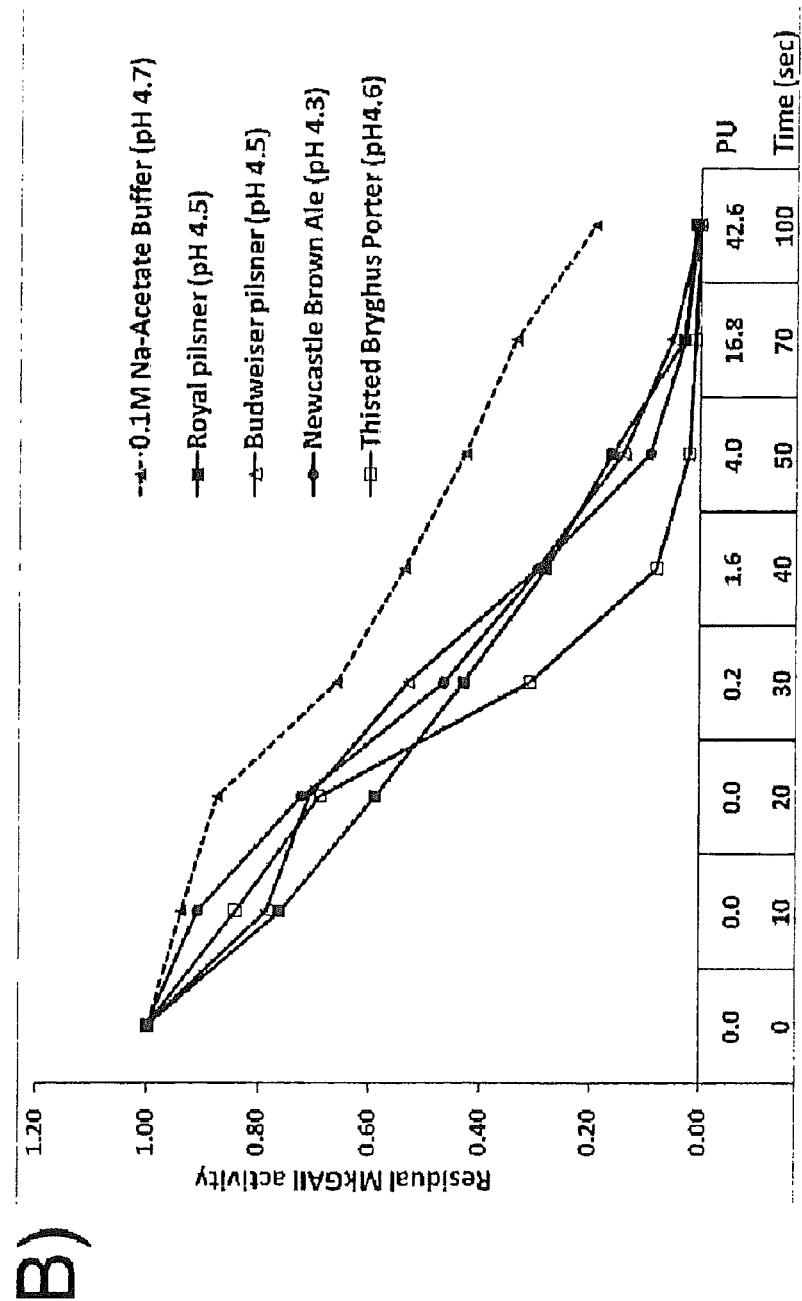
Figure 9:
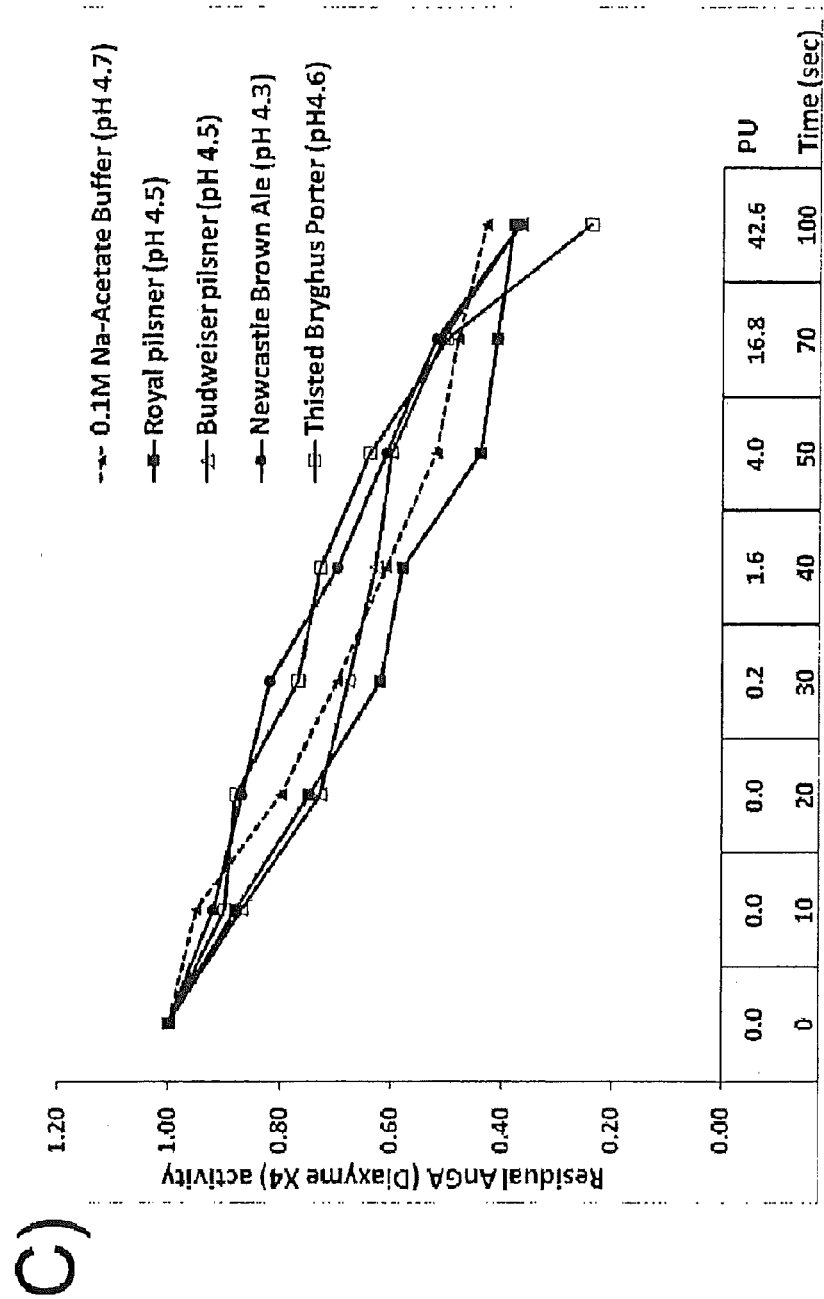

In addition, pasteurisations at 72° C. were performed in beers with widely different Specific Gravity (i.e. ° Plato): Budweiser Pilsner pH (4.5), Newcastle Brown Ale pH(4.3), Thisted bryghus Porter pH(4.6) and 0.1M Na-Acetate pH (4.7) used in previous studies of MkGA I and MkGA II thermostability (1). It is clear from the results shown in FIG. 9 that MkGA I and MkGA II are more thermolabile in beer compared to Na-Acetate buffer, whereas the thermostability of DIAZYME® X4 (AnGA) does not change significantly between buffer and beer. Surprisingly, the residual activity of MkGA I that has lowest themostability decreases faster in beer and the glucoamylase may get completely inactive in all beers with less than 25 PU compared to buffer, which hold small but significant (2%) residual activity after pasteurisation with 42 PU. Thisted bryghus porter is the beer in which MkGA I and MkGA II show the lowest thermostability.

Example 7

To express both forms of *M. kaoliang* glucoamylase, MkGA I and MkGA II, in the heterologous host *Hypocrea jecorina* (anamorph *Trichoderma reesei*), both genomic and cDNA sequences of the two corresponding genes were amplified by PCR from either the *M. kaoliang* genomic DNA or a pooled cDNA library prepared as described in previous examples with the upstream and downstream primers as indicated below (SEQ ID NOs: 13-15)

```
forward-
                                          (SEQ ID NO: 13)
5' GGGACAAGTTTGTACAAAAAAGCAGGCTCACCATGGTGAAGA
TCAGCATAAATCCCATC 3', reverse I (for MkGA II)-
                                          (SEQ ID NO: 14)
5'ACCACTTTGTACAAGAAAGCTGGGTCTACTTCCAGCTGTCGTT
GACGGTC 3'
and reverse II (for MkGA I)-
                                          (SEQ ID NO: 15)
5'ACCACTTTGTACAAGAAAGCTGGGTTCACCGTCCCGTGCCATA
GGGGCGTG 3'.
```

In addition, one extra fragment encoding MkGA I glucoamylase but starting from another ATG codon found in frame upstream of the putative start of translation (SEQ ID NO:17) was amplified using an upstream primer:

```
                                          (SEQ ID NO: 16)
5'GGGACAAGTTTGTACAAAAAAGCAGGCTATGATTGACACAAAA
CCGACTGATATCGTCTC 3'
```

Figure 10:
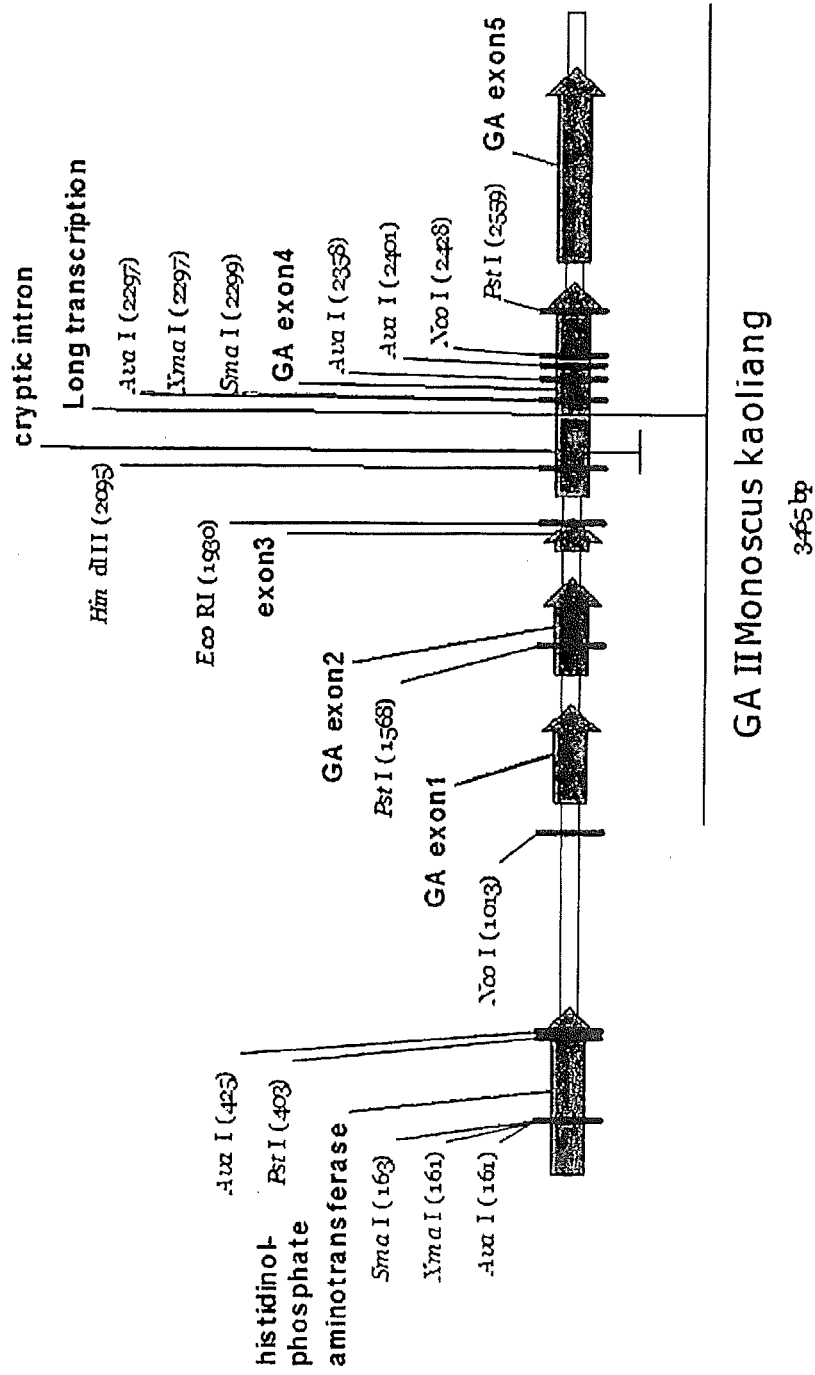
FIG. 10 is a schematic map of MkGA I/II genomic and CDS sequences.
Figure 10:
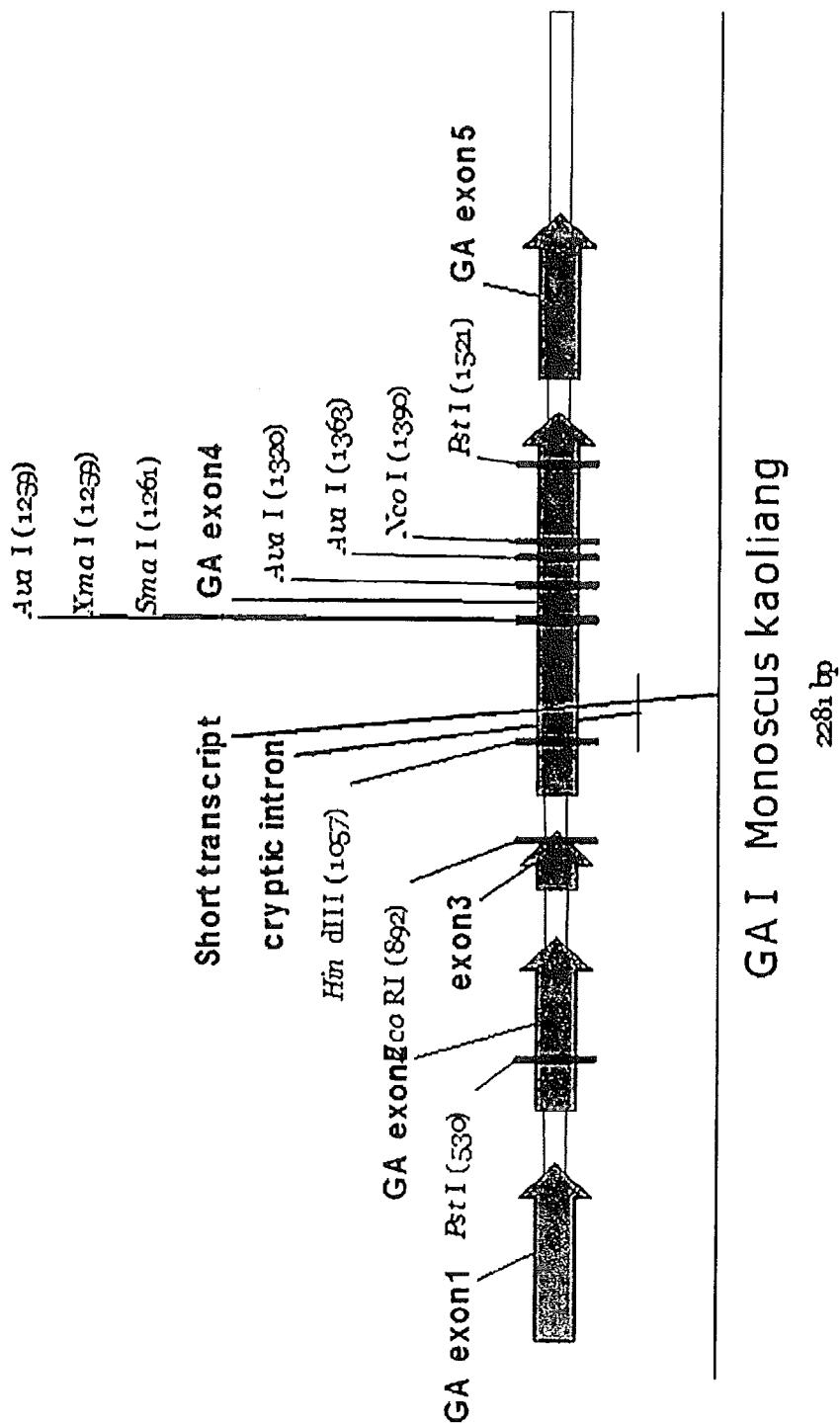
Figure 10:
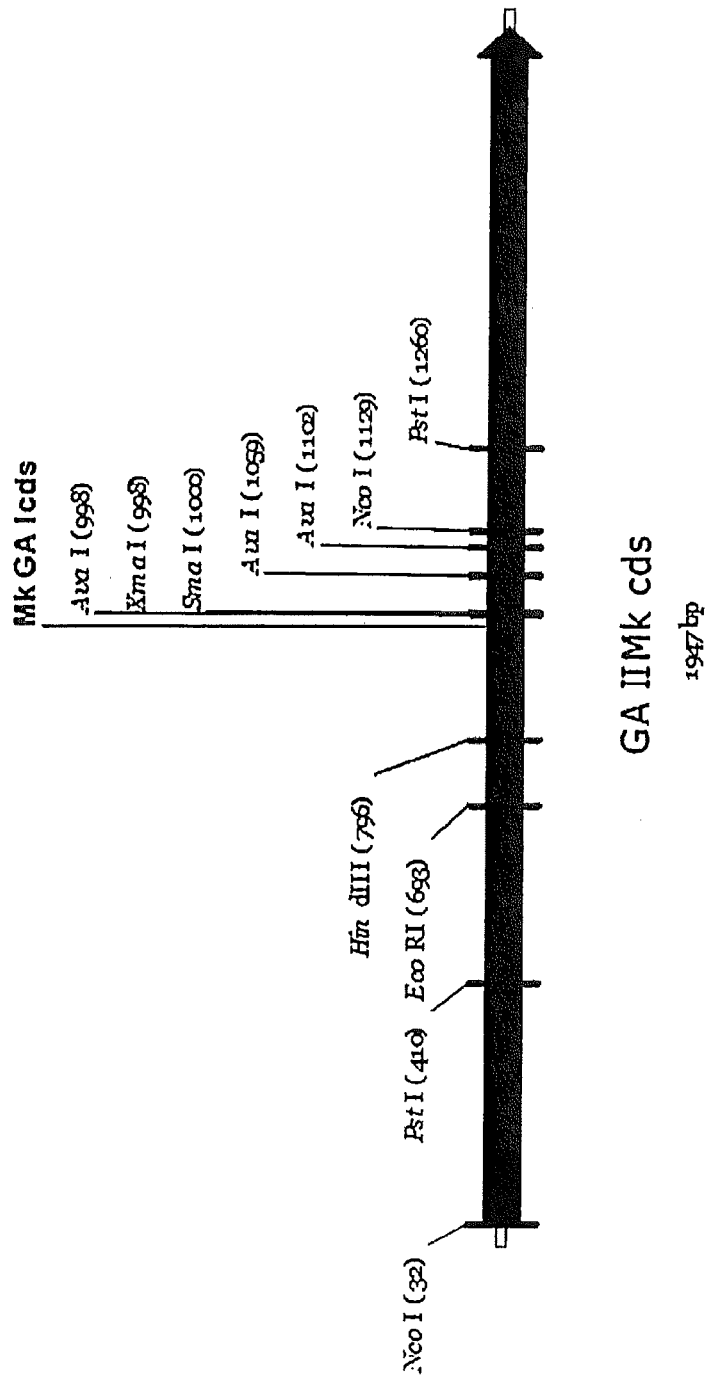
Figure 10:
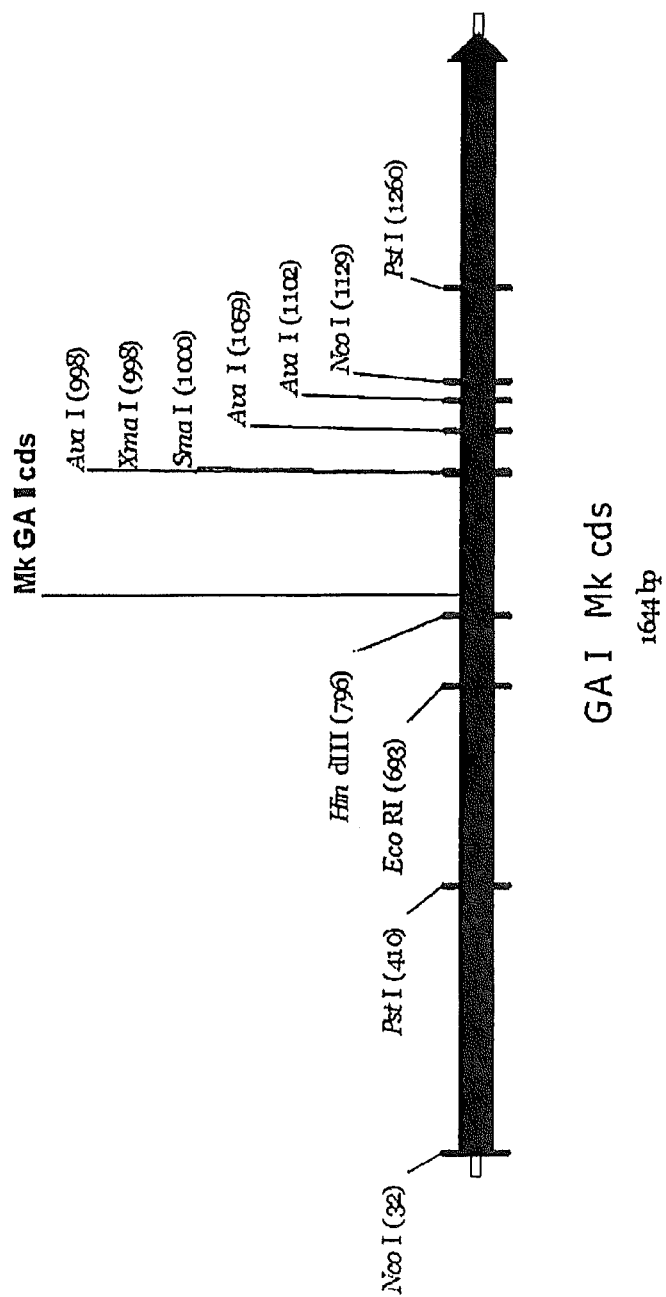
Figure 11:
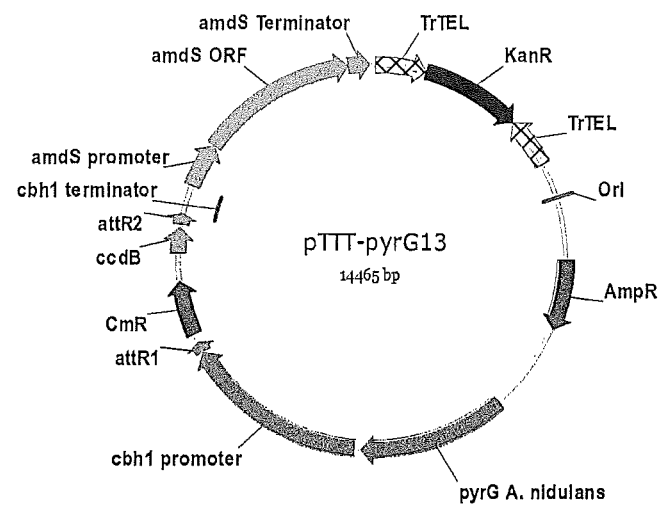
FIG. 11 is schematic maps of 5 expression plasmids for different *M. kaoliang* glucoamylase sequences and a schematic map of the destination vector pTTT-pyrG13.
Figure 11:
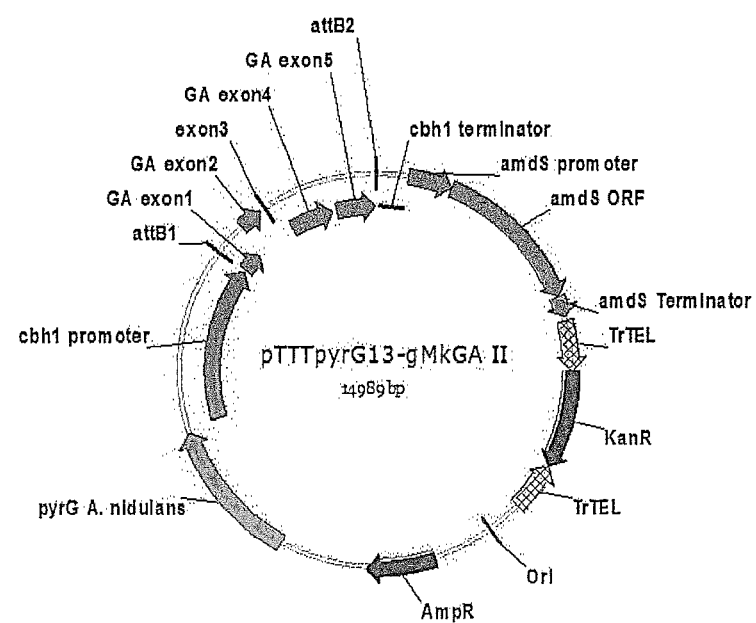
Figure 11:
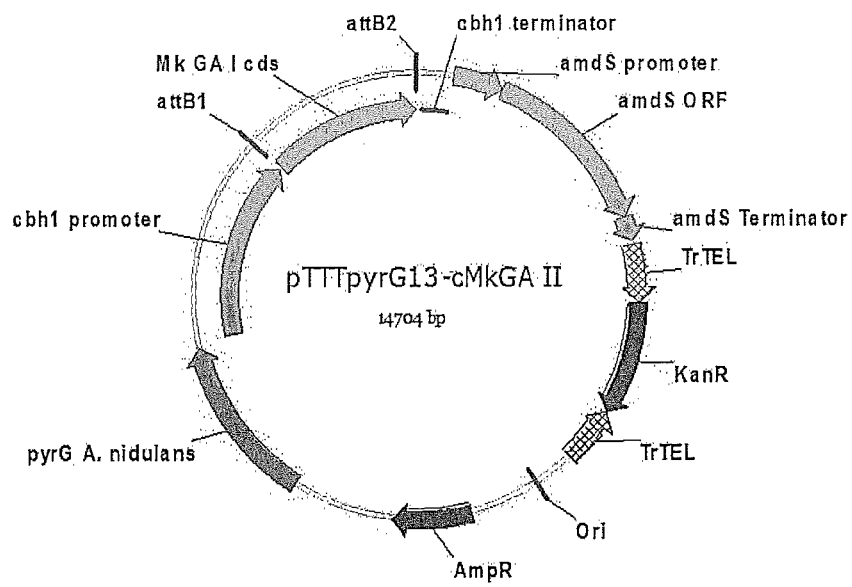
Figure 11:
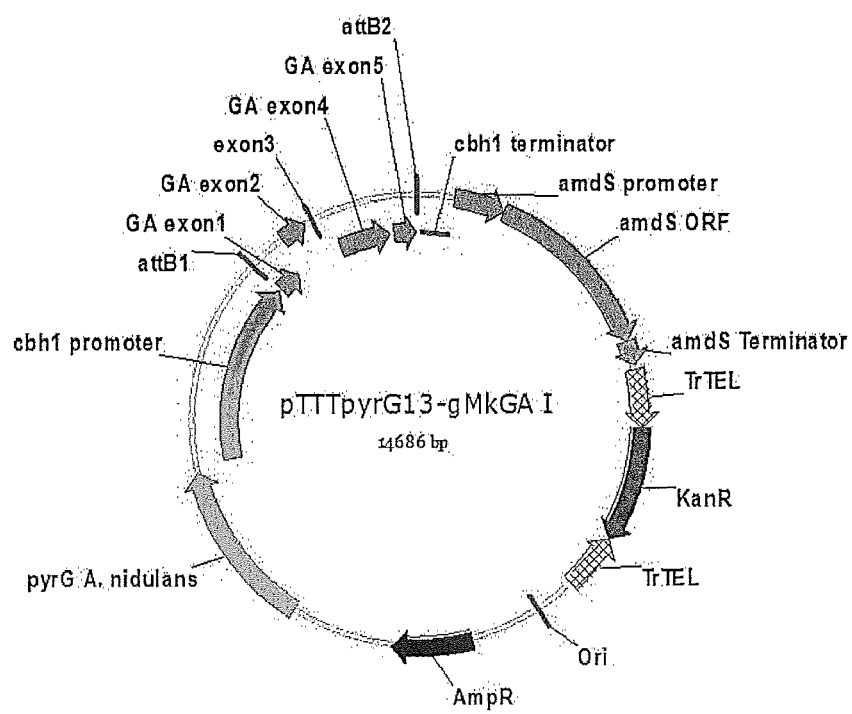
Figure 11:
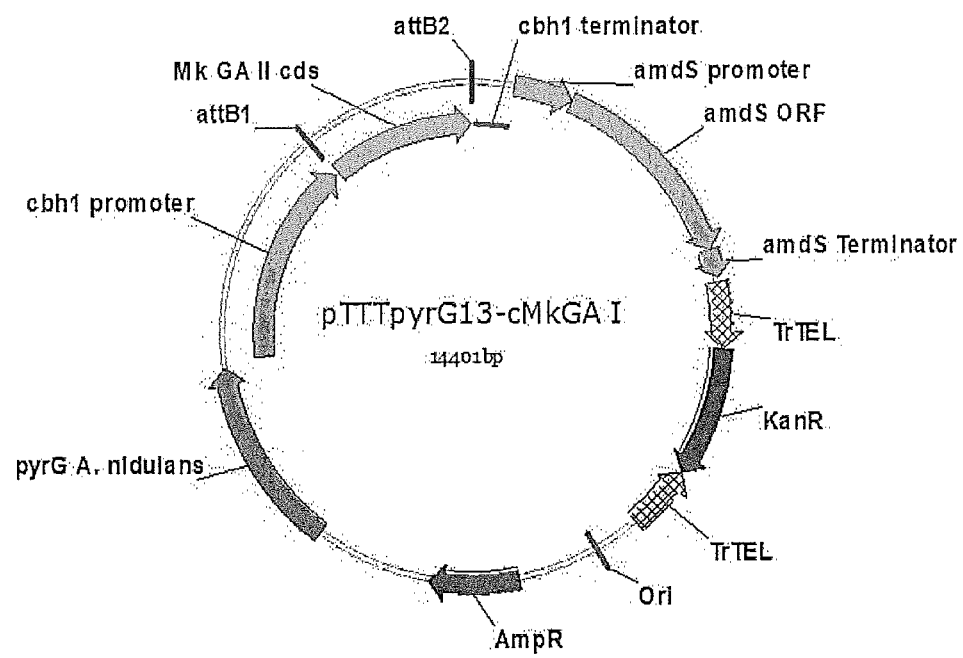
Figure 11:
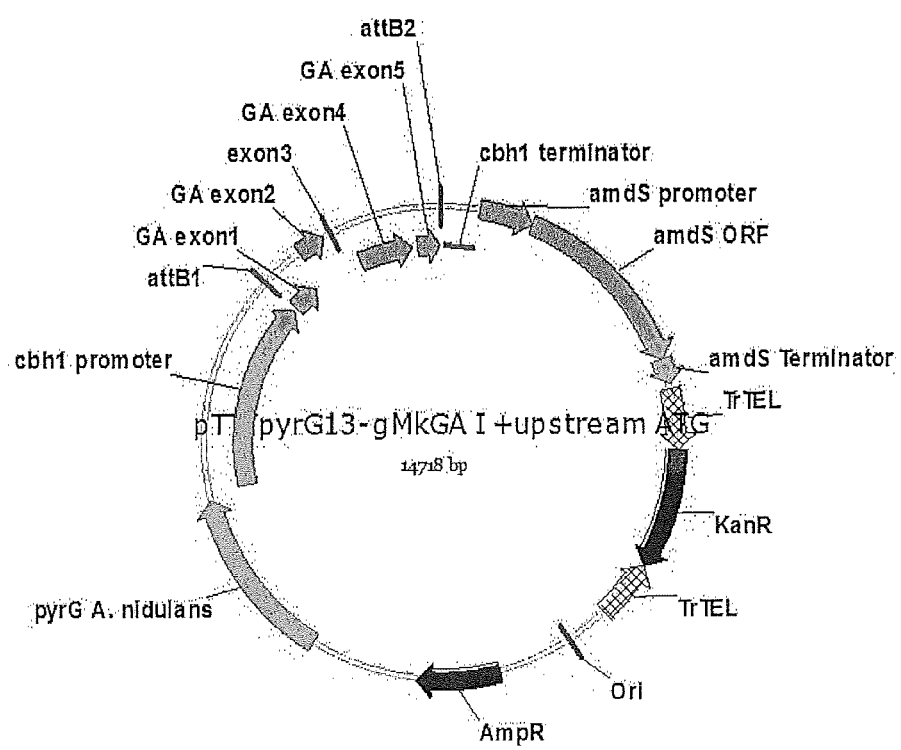

All primers included the specific recombination attB1 and attB2 sites compatible with a Gateway cloning technology (Invitrogen, Carlsbad, Calif., USA), to facilitate cloning of the amplified fragments in either pDONR™ 221 or pDONR™/Zeo vector followed by a second recombination reaction with the pTTTpyrG13 destination vector (FIG. 10). This vector allowed for expression of the MkGA I and MkGA II genes in *H. jecorina* cells and was described in WO2010141779A1. It contains the *T. reesei* cbhI-derived promoter and terminator regions driving a strong inducible expression of a gene of interest, the *Aspergillus nidulans* amdS and pyrG selective marker conferring growth of transformants on acetamide as a sole nitrogen source in the absence of uridine, and the *T. reesei* telomere regions allowing for a non-chromosomal plasmid maintenance in a fungal cell. The cbhI promoter and terminator regions are separated by the chloramphenicol resistance gene, $Cm^R$, and the ccdB gene lethal to *E. coli*, flanked by the bacteriophage lambda specific recombination sites attR1, attR2. Such configuration allows for direct selection of recombinants containing the *M. kaoliang* GA sequences under the control of the cbhI regulatory elements in the right orientation via the Gateway® LR recombination reaction. The final expression plasmids are shown in FIG. 11 and the identity of the specific genomic and cDNA sequences cloned was confirmed by a sequence analysis. All cloning steps were performed according to recommendations of the supplier (Invitrogen, Carlsbad, Calif., USA).

Isolated plasmids were transformed in the *H. jecorina* Quad strain deleted for four major cellulases (Δcbh1, Δcbh2, Δegl1, Δegl2, pyr4-) using a PEG-protoplast method as described elsewhere (US20110020899). Transformants selected for growth on minimal medium with acetamide as a nitrogen source were harvested and a spore mixture was used to inoculate Glycine production medium (4.7 g/L $(NH_4)_2SO_4$, 33 g/L 1,4-Piperazinebis(propanesulfonic acid), pH 5.5, 6.0 g/L glycine, 5.0 g/L $KH_2PO_4$, 1.0 g/L $CaCl_2 \times 2H_2O$, 1.0 g/L $MgSO_4 \times 7H_2O$, 2.5 ml/L of 400x *T. reesei* trace elements {5 g/L $FeSO_4 \times 7H_2O$, 1.4 g/L $ZnSO_4 \times 7H_2O$, 1.6 g/L $MnSO_4 \times H_2O$, 3.7 g/L $CoCl_2 \times 6H_2O$}, 20 g/L Glucose, 0.6 g/L Sophorose). After growth for 5 days at 28 C in shake flasks on a rotary shake at 200 rpm, cultures samples were harvested and analysed for production of *M. kaoliang* glucoamylases by both SDS-PAGE and activity assay using para-nitrophenyl-α-D-glucopyranoside as a substrate. SDS-PAGE analysis and glucoamylase activity assay were performed as described in example 1.

Figure 12:
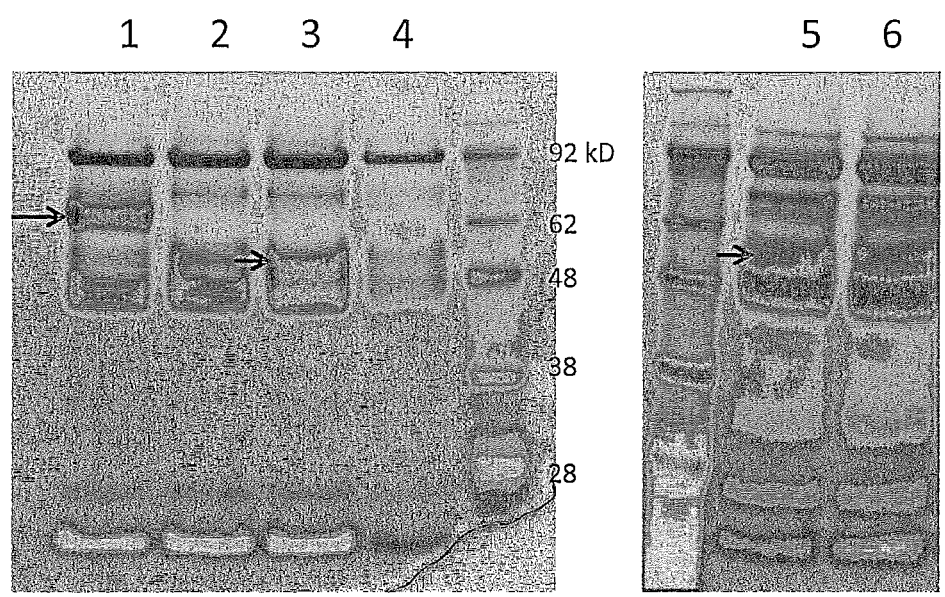
FIG. 12 depicts SDS-PAGE of *Hypocrea jecorina* fermentation samples expressing different *M. kaoliang* GA encoding sequences: 1, MkGA II genomic clone; 2, MkGA II cDNA clone; 3, MkGA I genomic clone; 4, MkGA I cDNA clone; 5, MkGA I genomic clone starting from the upstream ATG; 6, Recipient strain. 20 ul of filtered culture samples were loaded per lane on 10% SDS-PAGE. GA specific bands are indicated with arrows.

As seen in FIG. 12 and below table 10, both forms of MkGA I and II were successfully expressed in their active form in the heterologous host *H. jecorina*. For both genes, only genomic sequences resulted in detectable expression of the corresponding glucoamylase molecules. More pronounced expression was observed when the downstream ATG codon was used as a start of translation indicating that it might be the true start of the signal peptide.

TABLE 10

Activity of heterologously expressed *M. kaoliang* glucoamylases. Fermentation samples were diluted equally and activity was measured against para-nitrophenyl-α-D-glucopyranoside

| Sample | Activity, O.D. 405 nm |
|---|---|
| Mk GAII genomic | 0.68 |
| Mk GAII cDNA | 0.1 |
| Mk GAI genomic | 0.7 |
| Mk GAI cDNA | 0.084 |
| Mk GAI genomic + ATG | 0.42 |
| Recipient | 0.08 |

Figure 13:
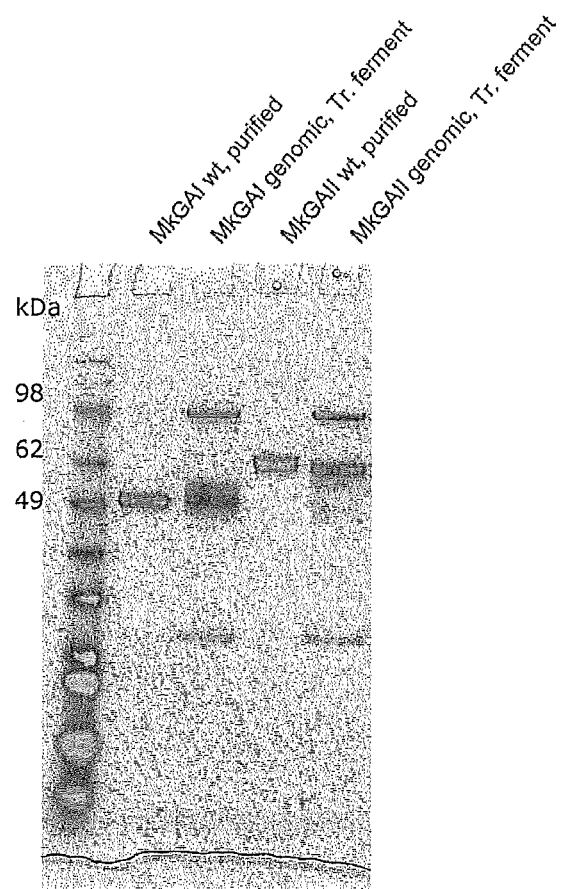
FIG. 13 depicts SDS-PAGE of *H. jecorina* fermentation samples expressing two different *M. kaoliang* GA encoding sequences (MkGAI and MkGAII) and the purified two GA's from *M. kaoliang*.

The *T. reesei* expressed MkGA-I/-II were analysed by MS. A partial sequence analysis (covering 70% of the full sequence) was performed on the mature proteins from both *M. kaoliang* and *T. reesei* (purified from SDS-page, see FIG. 13) and showed the respective variants to be 100% identical (not shown). Thermostability of MkGA-I/-II from *T. reesei* (the crude ferment) were examined and were very similar to the purified wild-type enzymes from *M. kaoliang* (Table 11). Notably, it was possible to inactivate gMkGA I produced in *T. reesei* with less than 42 PU.

TABLE 11

Residual glucoamylase activity as a function of the applied pasteurisation units at 72° C. in beer of MkGA I and MkGA II from *M. kaoliang* and *T. reesei*. Residual activity is meassured on a β-D-maltoside substrate and calculated as the actual activity divided with the initial activity (0 PU) and results are an average of 3 determinations.

| | | Residual glucoamylase activity after pasteurisation at 72° C. | | | |
|---|---|---|---|---|---|
| Pasteurisation Units [PU] | Sample ID | MkGA I *M. Kaoliang* (purified) | MkGA II *M. Kaoliang* (purified) | gMkGA I *T. Reesei* (ferment) | gMkGA II *T. Reesei* (ferment) |
| 0.000 | 1 | 1.000 | 1.000 | 1.000 | 1.000 |
| 0.001 | 2 | 0.830 | 0.954 | 0.810 | 0.990 |
| 0.005 | 3 | 0.470 | 0.892 | 0.530 | 0.920 |
| 0.167 | 4 | 0.063 | 0.849 | 0.155 | 0.840 |
| 1.557 | 5 | 0.040 | 0.407 | 0.042 | 0.610 |
| 3.990 | 6 | 0.024 | 0.225 | 0.031 | 0.330 |
| 16.70 | 7 | 0.001 | 0.101 | 0.020 | 0.150 |
| 42.60 | 8 | 0.000 | 0.058 | 0.000 | 0.070 |
| 66.58 | 9 | 0.000 | 0.010 | 0.000 | 0.040 |
| 99.98 | 10 | 0.000 | 0.000 | 0.000 | 0.010 |
| 239.6 | 11 | 0.000 | 0.000 | 0.000 | 0.000 |
| 563.7 | 12 | 0.000 | 0.000 | 0.000 | 0.000 |

MkGA I and MkGA II expressed in both *H. jecorina* and *M. kaoliang* were tested in brewing experiments. A wort was made using Munton's malt extract. 340 g Munton's malt extract was dissolved in 1500 ml hot water. This slurry was added 5 pellets of hops, pH adjusted to 5.2 by H2SO4. and boiled for 1 hour before being autoclaved at 121° C. for 15 minutes. Afterwards, 0.6 g freshly produced Weihenstephan yeast was added 100 g cooled wort together with the different enzymes (as described in example 5).

The worts (normally 100 ml) were fermented at 18° C. and 150 rpm in 500 ml conical flasks. Residual activity was measured before and after fermentation. Production of ethanol was indirectly measured by weight loss of ferments. Alcohol was measured on an Anton Paar Alcoanalyzer and calculation of RDF was done on basis of specific gravity of the beer and alcohol concentration from the Alcoanalyzer.

Figure 14:
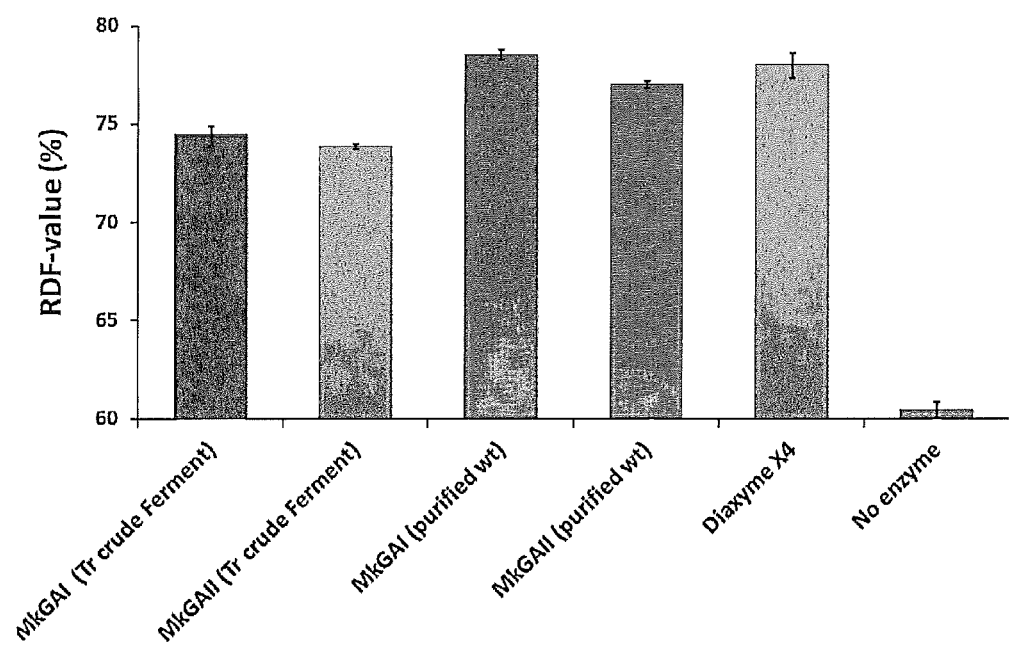
FIG. 14 depicts RDF values determined for listed GA (ferments, purified proteins and products) applied to the FV with similar activity (10M-GAU), using a malt extract wort. Results are an average of 2 determinations. Error bars are ±std.

The performance in the beer FV application of gMkGA I and gMkGA II from *T. reesei* showed to be high but decreased (in terms of RDF-values) compared to the purified proteins from *M. kaoliang* (see FIG. 14). The enzymes were dosed on activity (GAU/mL) and the decreased performance may be due to side-activities in the crude ferment from *T. reesei* rather an actual performance difference in the FV as they have similar amino acid sequences.

gDNA MkGA II (SEQ ID NO: 1)

```
   1 atggtgaaga tcagcataaa tcccatcttg aaacggacat tccctctatc
  51 agtgctgctg gcgccgctcc tcgcagcctg tcttggggct tcaaacctag
 101 ctcagatcgc tgttgccgct gcaacatcgg cggagtcaag tgctgcgtct
 151 gattccttag attcatggct ggccagagag actccatatg cccttgatgg
 201 aatttttaaat aacatcggcc cagacggcgc gaaggctgtg ggtgcagtct
 251 ctggcgtggt ggttgcgagt ccgagcaaga gtaatccgga ttgtgagtat
 301 tctcgtattt ccagccccca acgtcaagtg catctatagc aaagaaagaa
 351 aaagctcatg ctaatggatg tatctgtata tatttctaca cttggactcg
 401 tgacgctgct ctgactgtta aatgtctgac cgacctcttc ctggtcaatg
 451 gtgacgtgaa tctgcagtcg cagatccaga actacatcag ccgccaggca
 501 tatttgcaga ccgtatccaa tccatctggt gacctgtcga ctggggact
 551 tggtgagccc aaattcgagg ttgatggcgc tgcatttacc ggttcctggg
 601 gccgtcctca acgagatggg cctgcgttga gggctacggc tctgattgct
 651 tatgccaatt ggctcattgt aggtgtttgc atgttggatt ttcttttctt
 701 tctaatataa tcttctcttg ttgttacttg ctaacttcca tctacagagc
 751 aatggacaga cctcgacggc ggagtccatt gtttggccag ttgtccagaa
 801 tgaccttca tatgtgatgc agtattggaa ttcatctacc tttggtttgt
 851 cgaggcctct aaaatgggac aagcattctc agctaacgta tggaaacttc
 901 atgcagacct ctgggaggaa gtctacggct catcgttttt taccacggcc
 951 gtgcagcatc gtgccctagt cgaaggtgcg gctttcgcca aaaagcttgg
1001 ccactcttgt cccgactgtc tctcccaggc atcgcagatc tctgctttt
1051 tgcagtcgta ctggaccggt gcttacgtgc tctctaactt tggtggtggc
1101 cgctcaggga aggacgccaa ctcgatcctc ggagttctgc atactttcga
1151 ccccgatgca gactgcgatg ataccacttt ccagccttgt tctgcccggg
1201 cgcttgcgaa ccataaagta gttacggact ctttccggtc catctactct
1251 ctcaactcgg gtattgccca gggtcaagcc gtggctgtgg gacggtatcc
1301 cgaggacgtc taccagggag gcaatccatg gtatctctgt actttggctg
1351 cggcggagca gctctacgac gcgctgtatc aatgggatcg aatcgggtcc
1401 ttgtctataa cggacgtcag tctgggattc ttccaggacc tgtacccgtc
1451 cgctgcagta ggtgactatg cgtcttccac ggagacatac agagatatca
1501 tggcagctgt gaaggcctat gcgaatggat atatggatat tgctgtaagg
1551 agagctcctt tccatctttt ccttgtccca tgctgaaata gtgctacaga
1601 gaaagtacac acctgccaac ggcgctctag cagagcagtt ttctagagac
1651 gatggttccc cagtctcagc ggtcgatctg acctggtcgt atgcctctct
1701 tctcacggca gcagccgac gaggctccca gatgccgcca tcgtggaacg
1751 aatcttcttc caacaagcct ccatcgactt gctcagcatc tctgcgacg
1801 ggggcctatg cctcggctac caacaccgtc tggcccacag cgtcgtgtgc
1851 ggcgacgccg acagccgtgc ctgtgcgttt caacgaactg gtcacgactt
1901 cagtcgggga taaggtagcc ctcgtggggt ccaccctgc tctggggtca
1951 tggaatgtct ctgcggccgt cgcactgagt gcagacgaat acagcagcgt
```

```
2001  cacgccccta tggcacggga cggtgagtct cccgaccaaa acgagcttcg
2051  agtataagta tgtggtgcag aaggagtctg gggaagtgga ctgggagggc
2101  ggagagaatc ggtcgtacac agtgccagag ggatgcgagg gctcttcagt
2151  gaccgtcaac gacagctgga agtag
``` cDNA Sequence of MkGA II
(SEQ ID NO: 2)

```
   1  atggtgaaga tcagcataaa tcccatcttg aaacggacat tccctctatc
  51  agtgctgctg gcgccgctcc tcgcagcctg tcttggggct tcaaacctag
 101  ctcagatcgc tgttgccgct gcaacatcgg cggagtcaag tgctgcgtct
 151  gattccttag attcatggct ggcagagag actccatatg cccttgatgg
 201  aattttaaat aacatcggcc cagacggcgc gaaggctgtg ggtgcagtct
 251  ctggcgtggt ggttgcgagt ccgagcaaga gtaatccgga ttatttctac
 301  acttggactc gtgacgctgc tctgactgtt aaatgtctga ccgacctctt
 351  cctggtcaat ggtgacgtga atctgcagtc gcagatccag aactacatca
 401  gccgccaggc atatttgcag accgtatcca atccatctgg tgacctgtcg
 451  actggggggac ttggtgagcc caaattcgag gttgatggcg ctgcatttac
 501  cggttcctgg ggccgtcctc aacgagatgg gcctgcgttg agggctacgg
 551  ctctgattgc ttatgccaat ggctcatta gcaatggaca gacctcgacg
 601  gcggagtcca ttgtttggcc agttgtccag aatgaccttt catatgtgat
 651  gcagtattgg aattcatcta cctttgacct ctgggaggaa gtctacggct
 701  catcgttttt taccacggcc gtgcagcatc gtgccctagt cgaaggtgcg
 751  gctttcgcca aaaagcttgg ccactcttgt cccgactgtc tctcccaggc
 801  atcgcagatc ctctgctttt tgcagtcgta ctggaccggt gcttacgtgc
 851  tctctaactt tggtggtggc cgctcaggga aggacgccaa ctcgatcctc
 901  ggagttctgc atactttcga ccccgatgca gactgcgatg ataccacttt
 951  ccagccttgt tctgcccggg cgcttgcgaa ccataaagta gttacggact
1001  ctttccggtc catctactct ctcaactcgg gtattgccca gggtcaagcc
1051  gtggctgtgg acggtatcc cgaggacgtc taccagggag gcaatccatg
1101  gtatctctgt actttggctg cggcggagca gctctacgac gcgctgtatc
1151  aatgggatcg aatcgggtcc ttgtctataa cggacgtcag tctgggattc
1201  ttccaggacc tgtacccgtc cgctgcagta ggtgactatg cgtcttccac
1251  ggagacatac agagatatca tggcagctgt gaaggcctat gcgaatggat
1301  atatggatat tgctagaaag tacacacctg ccaacggcgc tctagcagag
1351  cagttttcta gagacgatgg ttccccagtc tcagcggtcg atctgacctg
1401  gtcgtatgcc tctcttctca cggcagcagc cagacgaggc tcccagatgc
1451  cgccatcgtg gaacgaatct tcttccaaca agcctccatc gacttgctca
1501  gcatcctctg cgacggggc ctatgcctcg ctaccaaca ccgtctggcc
1551  cacagcgtcg tgtgcggcga cgccgacagc cgtgcctgtg cgtttcaacg
1601  aactggtcac gacttcagtc ggggataagg tagccctcgt ggggtccacc
1651  cctgctctgg ggtcatggaa tgtctttgcg gccgtcgcac tgagtgcaga
1701  cgaatacagc agcgtcacgc ccctatggca cgggacggtg agtctcccga
```

-continued

```
1751  ccaaaacgag cttcgagtat aagtatgtgg tgcagaagga gtctggggaa 1801  gtggactggg agggcggaga gaatcggtcg tacacagtgc cagagggatg 1851  cgagggcttt tcagtgaccg tcaacgacag ctggaagtag
```

Amino Acid Sequence of MkGA II (the mature protein)
(SEQ ID NO: 3)

```
  1  ASDSLDSWLA RETPYALDGI LNNIGPDGAK AVGAVSGVVV ASPSKSNPDY

51  FYTWTRDAAL TVKCLTDLFL VNGDVNLQSQ IQNYISRQAY LQTVSNPSGD

101  LSTGGLGEPK FEVDGAAFTG SWGRPQRDGP ALRATALIAY ANWLISNGQT

151  STAESIVWPV VQNDLSYVMQ YWNSSTFDLW EEVYGSSFFT TAVQHRALVE

201  GAAFAKKLGH SCPDCLSQAS QILCFLQSYW TGAYVLSNFG GGRSGKDANS

251  ILGVLHTFDP DADCDDTTFQ PCSARALANH KVVTDSFRSI YSLNSGIAQG

301  QAVAVGRYPE DVYQGGNPWY LCTLAAAEQL YDALYQWDRI GSLSITDVSL

351  GFFQDLYPSA AVGDYASSTE TYRDIMAAVK AYANGYMDIA RKYTPANGAL

401  AEQFSRDDGS PVSAVDLTWS YASLLTAAAR RGSQMPPSWN ESSSNKPPST

451  CSASSATGAY ASATNTVWPT ASCAATPTAV PVRFNELVTT SVGDKVALVG

501  STPALGSWNV SAAVALSADE YSSVTPLWHG TVSLPTKTSF EYKYVVQKES

551  GEVDWEGGEN RSYTVPEGCE GSSVTVNDSW K
``` gDNA MkGA I
(SEQ ID NO: 4)

```
  1  atggtgaaga tcagcataaa tccctctttg aaacggacat tccctctatc 51  agtgctgctg gcgccgctcc tcgcagcctg tcttggggct tcaaacctag 101  ctcagatcgc tgttgccgct gcaacatcgg cggagtcaag tgctgcgtct 151  gattccttag attcatgggc tggccagagag actccatatg cccttgatgg 201  aattttaaat aacatcggcc cagacggcgc gaaggctgtg ggtgcagtct 251  ctggcgtggt ggttgcgagt ccgagcaaga gtaatccgga ttgtgagtat 301  tctcgtattt ccagccccca acgtcaagtg catctatagc aaagaaagaa 351  aaagctcatg ctaatggatg tatctgtata tatttctaca cttggactcg 401  tgacgctgct ctgactgtta aatgtctgac cgacctcttc ctggtcaatg 451  gtgacgtgaa tctgcagtcg cagatccaga actacatcag ccgccaggca 501  tatttgcaga ccgtatccaa tccatctggt gacctgtcga ctggggact 551  tggtgagccc aaattcgagg ttgatggcgc tgcatttacc ggttcctggg 601  gccgtcctca acgagatggg cctgcgttga gggctacggc tctgattgct 651  tatgccaatt ggctcattgt aggtgtttgc atgttggatt tcttttcctt 701  tctaatataa tcttctcttg ttgttacttg ctaacttcca tctacagagc 751  aatggacaga cctcgacggc ggagtccatt gtttggccag ttgtccagaa 801  tgacctttca tatgtgatgc agtattggaa ttcatctacc tttggtttgt 851  cgaggcctct aaaatgggac aagcattctc agctaacgta tggaaacttc 901  atgcagacct ctggaggaa gtctacggct catcgttttt taccacggcc 951  gtgcagcatc gtgccctagt cgaaggtgcg gctttcgcca aaagcttgg 1001 ccactcttgt cccgactgtc tctcccaggc atcgcagatc tctgctttt 1051 tgcagtcgta ctggaccggt gcttacgtgc tctctaactt tggtggtggc 1101 cgctcaggga aggacgccaa ctcgatcctc ggagttctgc atactttcga 1151 ccccgatgca gactgcgatg ataccacttt ccagccttgt tctgcccggg
```

-continued

```
1201  cgcttgcgaa ccataaagta gttacggact ctttccggtc catctactct
1251  ctcaactcgg gtattgccca gggtcaagcc gtggctgtgg acggtatcc
1301  cgaggacgtc taccagggag gcaatccatg gtatctctgt actttggctg
1351  cggcggagca gctctacgac gcgctgtatc aatgggatcg aatcgggtcc
1401  ttgtctataa cggacgtcag tctgggattc ttccaggacc tgtacccgtc
1451  cgctgcagta ggtgactatg cgtcttccac ggagacatac agagatatca
1501  tggcagctgt gaaggcctat gcgaatggat atatggatat tgctgtaagg
1551  agagctcctt tccatctttt ccttgtccca tgctgaaata gtgctacaga
1601  gaaagtacac acctgccaac ggcgctctag cagagcagtt ttctagagac
1651  gatggttccc cagtctcagc ggtcgatctg acctggtcgt atgcctctct
1701  tctcacggca gcagccagac gaggctccca gatgccgcca tcgtggaacg
1751  aatcttcttc caacaagcct ccatcgactt gctcagcatc ctctgcgacg
1801  gggccctatg cctcggctac caacaccgtc tggcccacag cgtcgtcacg
1851  cccctatggc acgggacggt gagtctcccg accaaaacga gcttcgagta
1901  taagtatgtg gtgcagaagg agtctgggga agtggactgg gagggcggag
1951  agaatcggtc gtacacagtg ccagagggat gcgagggctc ttcagtgacc
2001  gtcaacgaca gctggaagta g
``` cDNA Sequence of MkGA I (SEQ ID NO: 5)

```
  1  atggtgaaga tcagcataaa tccccatcttg aaacggacat tccctctatc
 51  agtgctgctg gcgccgctcc tcgcagcctg tcttggggct tcaaacctag
101  ctcagatcgc tgttgccgct gcaacatcgg cggagtcaag tgctgcgtct
151  gattccttag attcatggct ggccagagag actccatatg cccttgatgg
201  aattttaaat aacatcggcc cagacggcgc gaaggctgtg ggtgcagtct
251  ctggcgtggt ggttgcgagt ccgagcaaga gtaatccgga ttatttctac
301  acttggactc gtgacgctgc tctgactgtt aaatgtctga ccgacctctt
351  cctggtcaat ggtgacgtga atctgcagtc gcagatccag aactacatca
401  gccgccaggc atatttgcag accgtatcca atccatctgg tgacctgtcg
451  actggggac ttggtgagcc caaattcgag gttgatggcg ctgcatttac
501  cggttcctgg ggccgtcctc aacgagatgg gcctgcgttg agggctacgg
551  ctctgattgc ttatgccaat tggctcatta gcaatggaca gacctcgacg
601  gcggagtcca ttgtttggcc agttgtccag aatgaccttt catatgtgat
651  gcagtattgg aattcatcta cctttgacct ctgggaggaa gtctacggct
701  catcgttttt taccacggcc gtgcagcatc gtgccctagt cgaaggtgcg
751  gctttcgcca aaaagcttgg ccactcttgt cccgactgtc tctcccaggc
801  atcgcagatc ctctgctttt tgcagtcgta ctggaccggt gcttacgtgc
851  tctctaactt tggtggtggc cgctcaggga aggacgccaa ctcgatcctc
901  ggagttctgc atactttcga ccccgatgca gactgcgatg ataccacttt
951  ccagccttgt tctgcccggg cgcttgcgaa ccataaagta gttacggact
1001  ctttccggtc catctactct ctcaactcgg gtattgccca gggtcaagcc
1051  gtggctgtgg acggtatcc cgaggacgtc taccagggag gcaatccatg
```

```
1101  gtatctctgt actttggctg cggcggagca gctctacgac gcgctgtatc 1151  aatgggatcg aatcgggtcc ttgtctataa cggacgtcag tctgggattc 1201  ttccaggacc tgtacccgtc cgctgcagta ggtgactatg cgtcttccac 1251  ggagacatac agagatatca tggcagctgt gaaggcctat gcgaatggat 1301  atatggatat tgctagaaag tacacacctg ccaacggcgc tctagcagag 1351  cagttttcta gagacgatgg ttccccagtc tcagcggtcg atctgacctg 1401  gtcgtatgcc tctcttctca cggcagcagc cagacgaggc tcccagatgc 1451  cgccatcgtg gaacgaatct tcttccaaca agcctccatc gacttgctca 1501  gcatcctctg cgacggggcc ctatgcctcg gctaccaaca ccgtctggcc 1551  cacagcgtcg tcacgcccct atggcacggg acggtga
```

Amino Acid Sequence of MkGA I (the mature protein)
(SEQ ID NO: 6)

```
  1  ASDSLDSWLA RETPYALDGI LNNIGPDGAK AVGAVSGVVV ASPSKSNPDY
 51  FYTWTRDAAL TVKCLTDLFL VNGDVNLQSQ IQNYISRQAY LQTVSNPSGD
101  LSTGGLGEPK FEVDGAAFTG SWGRPQRDGP ALRATALIAY ANWLISNGQT
151  STAESIVWPV VQNDLSYVMQ YWNSSTFDLW EEVYGSSFFT TAVQHRALVE
201  GAAFAKKLGH SCPDCLSQAS QILCFLQSYW TGAYVLSNFG GGRSGKDANS
251  ILGVLHTFDP DADCDDTTFQ PCSARALANH KVVTDSFRSI YSLNSGIAQG
301  QAVAVGRYPE DVYQGGNPWY LCTLAAAEQL YDALYQWDRI GSLSITDVSL
351  GFFQDLYPSA AVGDYASSTE TYRDIMAAVK AYANGYMDIA RKYTPANGAL
401  AEQFSRDDGS PVSAVDLTWS YASLLTAAAR RGSQMPPSWN ESSSNKPPST
451  CSASSATGPY ASATNTVWPT ASSRPYGTGR
```

Primer Deg.FW
(SEQ ID NO: 7)
GAYTAYTTYTAYACNTGG

Primer Deg.RV
(SEQ ID NO: 8)
YTGRTANACRTCDTCNGG

MkGA probe FW
(SEQ ID NO: 9)
CTGGTCAATGGTGACGTGAATC

MkGA probe RV
(SEQ ID NO: 10)
GCAATACCCGAGTTGAGAGAGTAG

Primer MkGA FW
(SEQ ID NO: 11)
ATGATTGACACAAAACCGACTGATATCGTCTC

Primer MkGA RV
(SEQ ID NO: 12)
CTACTTCCAGCTGTCGTTGACGGTCAC

Primer MkGA FW - Tr expression
(SEQ ID NO: 13)
5' GGGACAAGTTTGTACAAAAAAGCAGGCTCACCATGGTGAAGATCAGCATAAATCCCATC 3', Primer MkGA II RV - Tr expression
(SEQ ID NO: 14)
5' ACCACTTTGTACAAGAAAGCTGGGTCTACTTCCAGCTGTCGTTGACGGTC 3'

Primer MkGA I RV - Tr expression
(SEQ ID NO: 15)
5' ACCACTTTGTACAAGAAAGCTGGGTTCACCGTCCCGTGCCATAGGGGCGTG 3'

Primer MkGA I + ATG FW - Tr expression
(SEQ ID NO: 16)
5' GGGACAAGTTTGTACAAAAAAGCAGGCTATGATTGACACAAAACCGACTGATATCGTCTC 3'

-continued gDNA MkGA I + ATG
(SEQ ID NO: 17)

```
   1  atgattgaca caaaaccgac tgatatcgtc tcgaaaatgg tgaagatcag
  51  cataaatccc atcttgaaac ggacattccc tctatcagtg ctgctggcgc
 101  cgctcctcgc agcctgtctt ggggcttcaa acctagctca gatcgctgtt
 151  gccgctgcaa catcggcgga gtcaagtgct cgtctgatt ccttagattc
 201  atggctggcc agagagactc catatgccct tgatggaatt ttaaataaca
 251  tcggcccaga cggcgcgaag ctgtgggtg cagtctctgg cgtggtggtt
 301  gcgagtccga gcaagagtaa tccggattgt gagtattctc gtatttccag
 351  cccccaacgt caagtgcatc tatagcaaag aaagaaaaag ctcatgctaa
 401  tggatgtatc tgtatatatt tctacacttg gactcgtgac gctgctctga
 451  ctgttaaatg tctgaccgac ctcttcctgg tcaatggtga cgtgaatctg
 501  cagtcgcaga tccagaacta catcagccgc caggcatatt tgcagaccgt
 551  atccaatcca tctggtgacc tgtcgactgg gggacttggt gagcccaaat
 601  tcgaggttga tggcgctgca tttaccggtt cctggggccg tcctcaacga
 651  gatgggcctg cgttgagggc tacggctctg attgcttatg ccaattggct
 701  cattgtaggt gtttgcatgt tggattttct tttctttcta atataatctt
 751  ctcttgttgt tacttgctaa cttccatcta cagagcaatg gacagacctc
 801  gacggcggag tccattgttt ggccagttgt ccagaatgac ctttcatatg
 851  tgatgcagta ttggaattca tctacctttg gtttgtcgag gcctctaaaa
 901  tgggacaagc attctcagct aacgtatgga aacttcatgc agacctctgg
 951  gaggaagtct acggctcatc gttttttacc acggccgtgc agcatcgtgc
1001  cctagtcgaa ggtgcggctt cgccaaaaaa gcttggccac tcttgtcccg
1051  actgtctctc ccaggcatcg cagatcctct gcttttgca gtcgtactgg
1101  accggtgctt acgtgctctc taactttggt ggtggccgct cagggaagga
1151  cgccaactcg atcctcggag ttctgcatac tttcgacccc gatgcagact
1201  gcgatgatac cactttccag ccttgttctg cccgggcgct tgcgaaccat
1251  aaagtagtta cggactcttt ccgtccatc tactctctca actcgggtat
1301  tgcccagggt caagccgtgg ctgtgggacg gtatcccgag gacgtctacc
1351  agggaggcaa tccatggtat ctctgtactt tggctgcggc ggagcagctc
1401  tacgacgcgc tgtatcaatg ggatcgaatc gggtccttgt ctataacgga
1451  cgtcagtctg ggattcttcc aggacctgta cccgtccgct gcagtaggtg
1501  actatgcgtc ttccacggag acatacagag atatcatggc agctgtgaag
1551  gcctatgcga atggatatat ggatattgct gtaaggagag ctccttttcca
1601  tcttttcctt gtcccatgct gaaatagtgc tacagagaaa gtacacacct
1651  gccaacggcg ctctagcaga gcagttttct agagacgatg gttccccagt
1701  ctcagcggtc gatctgacct ggtcgtatgc ctctcttctc acggcagcag
1751  ccagacgagg ctcccagatg ccgccatcgt ggaacgaatc ttcttccaac
1801  aagcctccat cgacttgctc agcatcctct cgacggggc cctatgcctc
1851  ggctaccaac accgtctggc ccacagcgtc gtcacgcccc tatggcacgg
1901  gacggtgagt ctcccgacca aaacgagctt cgagtataag tatgtggtgc
```

```
1951  agaaggagtc tggggaagtg gactgggagg gcggagagaa tcggtcgtac 2001  acagtgccag agggatgcga gggctcttca gtgaccgtca acgacagctg 2051  gaagtag
```

Various modifications and variations of the described embodiments will be apparent to those skilled in the art without departing from the scope and spirit of those embodiments. It should be understood that the subject matters as claimed should not be unduly limited to such specific embodiments. Indeed, various modifications of the described modes for carrying out the embodiments that are obvious to those skilled in the art are intended to be within the scope of the following claims.

All references discussed herein are incorporated herein by reference for all purposes.

What is claimed is:

1. An isolated polypeptide having glucoamylase activity comprising an amino acid sequence having at least 90% sequence identity to an amino acid sequence selected from the group consisting of the mature polypeptide of SEQ ID NO: 3 and 6.

2. The polypeptide according to claim 1, wherein the amino acid sequence comprises at least one or more amino acid residue(s) selected from the following groups:
   a) an amino acid residue selected from the group consisting of A and P at a position corresponding to position 459 in SEQ ID NO: 3 or 6,
   b) an amino acid residue selected from the group consisting of C and S at a position corresponding to position 473 in SEQ ID NO: 3 or 6,
   c) an amino acid residue selected from the group consisting of A and R at a position corresponding to position 474 in SEQ ID NO: 3 or 6,
   d) an amino acid residue selected from the group consisting of A and P at a position corresponding to position 475 in SEQ ID NO: 3 or 6,
   e) an amino acid residue selected from the group consisting of T and Y at a position corresponding to position 476 in SEQ ID NO: 3 or 6,
   f) an amino acid residue selected from the group consisting of P and G at a position corresponding to position 477 in SEQ ID NO: 3 or 6,
   g) an amino acid residue selected from the group consisting of A and G at a position corresponding to position 479 in SEQ ID NO: 3 or 6 and/or
   h) an amino acid residue selected from the group consisting of V and R at a position corresponding to position 480 in SEQ ID NO: 3 or 6.

3. The polypeptide according to claim 1, comprising the mature polypeptide of SEQ ID NO:3 or 6.

4. The polypeptide according to claim 1, wherein the polypeptide is inactivated by pasteurisation.

5. The polypeptide according to claim 1, wherein the polypeptide is obtained by recombinant expression in a host cell.

6. A composition comprising the polypeptide of claim 1.

7. The composition according to claim 6, wherein the composition is selected from the group consisting of a starch hydrolyzing composition, a saccharifying composition, a detergent composition, an alcohol fermentation enzymatic composition, and an animal feed composition.

8. The composition according to claim 6 further comprising an additional enzyme.

9. The composition according to claim 8, wherein the additional enzyme is selected from the group consisting of alpha-amylase, beta-amylase, peptidase (protease, proteinase, endopeptidase, exopeptidase), pullulanase, isoamylase, cellulase, endo-glucanase and related beta-glucan hydrolytic accessory enzymes, xylanase and xylanase accessory enzymes (for example, arabinofuranosidase, ferulic acid esterase, xylan acetyl esterase), acetolactate decarboxylase and glucoamylase, and combinations thereof.

10. The polypeptide according to claim 2, wherein the polypeptide is inactivated by pasteurisation.

11. The polypeptide according to claim 3, wherein the polypeptide is inactivated by pasteurisation.

* * * * *